US011046721B2

(12) United States Patent
Dmochowski et al.

(10) Patent No.: US 11,046,721 B2
(45) Date of Patent: *Jun. 29, 2021

(54) RUTHENIUM-BASED PHOTOLINKERS AND METHODS OF USE

(71) Applicant: The Trustees of the University of Pennsylvania, Philadelphia, PA (US)

(72) Inventors: Ivan J. Dmochowski, Philadelphia, PA (US); Julianne C. Griepenburg, Philadelphia, PA (US); Teresa L. Rapp, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/501,070

(22) PCT Filed: Aug. 4, 2015

(86) PCT No.: PCT/US2015/043548
§ 371 (c)(1),
(2) Date: Feb. 1, 2017

(87) PCT Pub. No.: WO2016/022526
PCT Pub. Date: Feb. 11, 2016

(65) Prior Publication Data
US 2017/0260221 A1 Sep. 14, 2017

Related U.S. Application Data

(60) Provisional application No. 62/033,007, filed on Aug. 4, 2014, provisional application No. 62/035,410, filed on Aug. 9, 2014.

(51) Int. Cl.
C07F 15/00 (2006.01)
C12N 15/113 (2010.01)
(Continued)

(52) U.S. Cl.
CPC ......... *C07F 15/0053* (2013.01); *B01J 35/004* (2013.01); *C07H 23/00* (2013.01);
(Continued)

(58) Field of Classification Search
CPC ... C07F 15/0053; C12N 15/113; C12N 13/00; C12Q 1/6823; C12Q 1/6825; B01J 2531/821
(Continued)

(56) References Cited

U.S. PATENT DOCUMENTS 5,034,506 A 7/1991 Summerton
5,296,566 A 3/1994 Brown-Wensley
(Continued)

FOREIGN PATENT DOCUMENTS

WO WO-2012103309 A2 * 8/2012 .......... B01J 31/1658

OTHER PUBLICATIONS

Griepenberg., "Regulating Gene Expression with Light-Activated Oligonucleotides.", 2014.
(Continued)

*Primary Examiner* — Jezia Riley
(74) *Attorney, Agent, or Firm* — Riverside Law LLP

(57) ABSTRACT

The present invention provides ruthenium-based photolinker compounds, caged molecules comprising the ruthenium-based photolinker compounds, and methods of use. In certain aspects, the compositions disclosed herein comprise an active domain conjugated to a ruthenium-based photolinker, such that irradiation of the photolinker exposes the active domain.

24 Claims, 35 Drawing Sheets

Specification includes a Sequence Listing.

(51) Int. Cl.
    C07H 23/00    (2006.01)
    C12N 13/00    (2006.01)
    C12Q 1/6823   (2018.01)
    C12Q 1/6825   (2018.01)
    B01J 35/00    (2006.01)
    C12Q 1/6818   (2018.01)
(52) U.S. Cl.
    CPC ............ *C12N 13/00* (2013.01); *C12N 15/113* (2013.01); *C12Q 1/6818* (2013.01); *C12Q 1/6823* (2013.01); *C12Q 1/6825* (2013.01); B01J 2531/821 (2013.01); C12N 2310/11 (2013.01); C12N 2310/32 (2013.01); C12N 2310/3233 (2013.01); C12N 2310/351 (2013.01); C12N 2310/3517 (2013.01); C12N 2310/531 (2013.01)
(58) Field of Classification Search
    USPC .......................................................... 435/6.1
    See application file for complete search history.

(56) References Cited

U.S. PATENT DOCUMENTS

| | | | |
|---|---|---|---|
| 5,874,046 | A | 2/1999 | Megerle |
| 9,540,634 | B2 | 1/2017 | Eberwine |
| 9,540,680 | B2 | 1/2017 | Eberwine |
| 2002/0102586 | A1 | 8/2002 | Ju |
| 2003/0201161 | A1 | 10/2003 | Nocera |
| 2012/0028814 | A1 | 2/2012 | Toloue |
| 2013/0066059 | A1 | 3/2013 | Chen |
| 2013/0273537 | A1 | 10/2013 | Eberwine |
| 2014/0073611 | A1 | 3/2014 | Wang |

OTHER PUBLICATIONS

O'Dell et al., "Amplification of mRNAs from Single, Fixed, TUNEL-Positive Cells", BioTechniques, (1998), vol. 25, no. 4, pp. 566-568, 570, XP001042378.

O'Connor et al., "A covalently linked phenanthridine-ruthenium(II) complex as a RNA probe", Chemical Communications, (2009), vol. 19, pp. 2640-2642.

Klan et al., "Photoremovable Protecting Groups in Chemistry and Biology : Reaction Mechanisms and Efficacy", Chemical Reviews, (2013), vol. 113, doi:doi:10.1021/cr300177k, pp. 119-191, XP055049223.

Griepenburg et al. Bioorganic & Medicinal Chemistry. 2013. 21:6198-6204. (Year: 2013).

Office Action (Response to Communication filed Feb. 1, 2017) dated Jul. 11, 2018 for U.S. Appl. No. 15/501,073 (pp. 1-12).

Boyden et al., "Millisecond-timescale, genetically targeted optical control of neural activity" 2005, Nat. Neurosci. 8:1263-1268.

Young and Deiters, "Photochemical control of biological processes" 2007, Org. Biomol. Chem. 5:999-1005.

Salierno et al., "Caged Amino Acids for Visible-Light Photodelivery" 2008, Eur. J. Inorg. Chem. 2008:1125-1128.

Gatterdam et al., "Three-Dimensional Protein Networks Assembled by Two-PhotonActivation" 2014, Angew. Chem. Int. Ed. Engl. 53:5680-5684.

Ellis-Davies, "A chemist and biologist talk to each other about caged neurotransmitters" 2013, Beilstein J. Org. Chem. 9:64-73.

Ellis-Davies, "Neurobiology with Caged Calcium" 2008, Chem. Rev. 108:1603-1613.

Tang and Dmochowski, "Controlling RNA Digestion by RNase H with aLight-Activated DNA Hairpin" 2006, Angew. Chem., Int. Ed. 45:3523-3526.

Tang and Dmochowski, "Regulating gene expression with lightactivated oligonucleotides" 2007, Mol. BioSyst. 3:100-110.

Tang et al., "Regulating Gene Expression in Zebrafish Embryos Using Light-Activated, Negatively Charged Peptide Nucleic Acids" 2007, J. Am. Chem. Soc. 129:11000-11001.

Ouyang et al., "Versatile Synthesis and Rational Design of Caged Morpholinos" 2009, J. Am. Chem. Soc. 131:13255-13269.

Shestopalov and Chen, "Spatiotemporal Control of Embryonic Gene Expression Using Caged Morpholinos" 2011, Methods Cell Biol. 104:151-172.

Shestopalov et al., "Light-controlled gene silencing in zebrafish embryos" 2007, Nat. Chem. Biol. 3:650-651.

Tomasini et al., "PhotoMorphsTM: A Novel Light-Activated Reagent forControlling Gene Expression in Zebrafish" 2009, Genesis 47:736-743.

Deiters et al., "Photocaged Morpholino Oligomers for the Light-Regulation of Gene Function in Zebrafish and Xenopus Embryos" 2010, J. Am. Chem. Soc. 132:15644-15650.

Yamazoe et al., "Cyclic Caged Morpholinos: Conformationally Gated Probes of Embryonic Gene Function" 2012, Angew. Chem., Int. Ed. 51:6908-6911.

Wang et al., "Manipulation of gene expression in zebrafish using caged circular morpholino oligomers" 2012, Nucleic Acids Res. 40:11155-11162.

Wu et al., "Caged circular antisense oligonucleotides for photomodulation of RNA digestion and gene expression in cells" 2013, Nucleic Acids Res. 41:677-686.

Ando et al., "Photo-mediated gene activation using caged RNA/DNA in zebrafish embryos" 2001, Nat. Genet. 28:317-325.

Jayakumar et al., "Remote activation of biomolecules in deep tissues using near-infrared-to-UV upconversion nanotransducers" 2012, Proc. Natl. Acad. Sci. U.S.A. 8483-8488.

Stoien and Wang, "Effect of Near-Ultraviolet and Visible Light on Mammalian Cells in Culture II. Formation of Toxic Photoproducts in Tissue Culture Medium by Blacklight" 1974, Proc. Natl. Acad. Sci. U.S.A. 71:3961-3965.

Yamazoe et al., "Sequential Gene Silencing Using Wavelength-Selective CagedMorpholino Oligonucleotides" 2014, Angew. Chem., Int. Ed. 53:10114-10118.

Zayat et al., "Ruthenium(II) Bipyridyl Complexes as Photolabile Caging Groups for Amines" 2006, Inorg. Chem. 45:1728-1731.

Garner et al., "[Ru(bpy)2(5-cyanouracil)2]2+ as a Potential Light-Activated Dual-Action Therapeutic Agent" 2011, Inorg. Chem. 50:9213-9215.

Zayat et al., "A New Strategy for Neurochemical Photodelivery: Metal-Ligand Heterolytic Cleavage" 2003, J. Am. Chem. Soc. 125:882-883.

Garner et al., "Effect of Electronic Structure on the Photoinduced Ligand Exchange of Ru(II) Polypyridine Complexes" 2011, Inorg. Chem. 50:4384-4391.

Araya et al., "Two-Photon Optical Interrogation of Individual Dendritic Spines with Caged Dopamine" 2013, ACS Chem. Neurosci. 4:1163-1167.

Zayat et al., "Ruthenium polypyridyl phototriggers: from beginnings to perspectives" 2013, Philos. Trans. R. Soc., A 371:20120330.

Fino et al., "RuBi-Glutamate: two-photon and visible-light photoactivation of neurons and dendritic spines" 2009, Front. Neural Circuits 3:1-9.

Filevich and Etchenique, "RuBiGABA-2: a hydrophilic caged GABA with long wavelength sensitivity" 2013, Photochem. Photobiol. Sci. 12:1565-1570.

Albani et al., "Selective Photoinduced Ligand Exchange in a New Tris-Heteroleptic Ru(II) Complex" 2013, J. Phys. Chem. A 117:13885-13892.

Albani et al., "New cyclometallated Ru(II) complex for potential application in photochemotherapy?" 2014, Photochem. Photobiol. Sci. 13:272-280.

Andaloussi et al., "Design of a peptide-based vector, PepFect6, for efficient delivery of siRNA in cell culture and systemically in vivo" 2011, Nucleic Acids Res, 39(9): 3972-3987.

Tornoe et al., "Peptidotriazoles on Solid Phase: [1,2,3]-Triazoles by Regiospecific Copper(I)-Catalyzed 1,3-Dipolar Cycloadditions of Terminal Alkynes to Azides" 2002, J. Org. Chem. 67:3057-3064.

(56) References Cited

OTHER PUBLICATIONS

Rostovtsev et al., "A Stepwise Huisgen Cycloaddition Process: Copper(I)-Catalyzed Regioselective 'Ligation' of Azides and Terminal Alkynes" 2002, Angew. Chem., Int. Ed. Engl. 41:2596-2599.
Bryant and Mayer, "Oxidation of C—H Bonds by [(bpy)2(py)RuIVO]2+ Occurs by Hydrogen Atom Abstraction" 2003, J. Am. Chem. Soc. 125:10351-10361.
Sears et al., "Photoinduced ligand exchange and DNA binding of cis-[Ru(phpy)(phen)(CH3CN)2] + with long wavelength visible light" 2013, J. Inorg. Biochem. 121:77-87.
Furuta et al., "Brominated 7-hydroxycoumarin-4-ylmethyls: Photolabile protecting groups with biologically useful cross-sections for two photon photolysis" 1999, Proc. Natl. Acad. Sci. U.S.A. 96:1193-1200.
Tallafuss et al., "Turning gene function On and Off using sense and antisense photo-morpholinos in zebrafish" 2012, Development (Cambridge, England) 139:1691-1699.
Guttman et al., "Chromatin signature reveals over a thousand highly conserved large non-coding RNAs in mammals" 2009, Nature, 458: 223-227.
Dmochowski et al., "Taking control of gene expression with light-activated oligonucleotides" 2007, J Biotechniques, 43: 161-171.
Richards et al., "RNA Bandages for Photoregulating In Vitro Protein Synthesis" 2008, J Bioorg Med Chem Lett, 18: 6255-6258.
Tang et al., "Phototriggering of Caged Fluorescent Oligodeoxynucleotides" 2005, Org Lett, 7: 279-282.
Tang et al, "Photoregulation of DNA polymerase I (Klenow) with caged fluorescent oligodeoxynucleotides" 2005, Bioorg Med Chem Lett, 15: 5303-5306.
Tang et al., "Regulating gene expression in human leukemia cells using light-activated oligodeoxynucleotides" 2008, Nucl Acids Res, 36: 559-569.
Richards et al., "Turning the 10-23 DNAzyme On and Off with Light" 2010 ChemBioChem, 11: 320-324.
Ruble et al., "Mismatch discrimination and efficient photomodulation with split 10-23 DNAzymes" 2012, Inorg Chim Acta, 380: 386-391.
Griepenburg et al., "Caged oligonucleotides for bidirectional photomodulation of let-7 miRNA in zebrafish embryos" 2013, Bioorg Med Chem Lett, 21(20): 6198-6204.
Zielinski et al., "In vivo identification of ribonucleoprotein—RNA interactions" 2006, J. Proc. Natl. Acad. Sci., U.S.A., 103, 1557-1562.
Zeng et al., "A protocol for PAIR: PNA-assisted identification of RNA binding proteins in living cell" 2006, J. Nat. Protoc., 1, 920-927.
Lovatt et al., "Transcriptome In Vivo Analysis (TIVA) of spatially defined single cells in intact live mouse and human brain tissue" 2014, Nat Methods, 11(2): 190-196.
McCray et al., "A New Approach to Time-Resolved Studies of ATP-Requiring Biological Systems: Laser Flash Photolysis of Caged ATP" 1980, Proc Natl Acad Sci USA, 77: 7237-7241.
Il'ichv et al., "Photochemical Reaction Mechanisms of 2-Nitrobenzyl Compounds: Methyl Ethers and Caged ATP" 2004, J Am Chem Soc, 126: 4581-4595.
Walker et al, "Photolabile 1-(2-Nitrophenyl)ethyl Phosphate Esters of Adenine Nucleotide Analogues. Synthesis and Mechanism of Photolysis" 1988; J am Chem Soc, 110: 7170-7177.
Corrie et al., "Photolytic Cleavage of 1-(2-Nitrophenyl)ethyl Ethers Involves Two Parallel Pathways and Product Release Is Rate-Limited by Decomposition of a Common Hemiacetal Intermediate" 2003, J Am Chem Soc, 125: 8546-8554.
Derossi et al., "The Third Helix of the Antennapedia Homeodornain Translocates through Biological Membrane" 1994, J Biol Chem, 269, 10444-10450.
Juliano et al., "Mechanisms and strategies for effective delivery of antisense and siRNA oligonucleotides" Nucl. Acids. Res. 2008, 36, 4158-4171.
Kumar et al., "Transvascular delivery of small interfering RNA to the central nervous system" Nature 2007, 448, 39-43.
Li et al., "Folate-Mediated Targeting of Antisense Oligodeoxynucleotides to Ovarian Cancer Cells" Pharm Res. 1998, 10, 1540-1545.
Sudimack et al., "Targeted drug delivery via the folate receptor" Adv. Drug Deliv. Rev. 2000, 41, 147-162.
Thierry et al., "Overcoming Multidrug Resistance in Human Tumor Cells Using Free and Liposomally Encapsulated Antisense Oligodeoxynucleotides" Biochem Biophys Res Commun 1993, 190, 952-960.
Wahlestedt et al., "Potent and nontoxic antisense oligonucleotides containing locked nucleic acids" Proc. Natl. Acad. Sci. USA 2000, 97, 5633-5638.
Eberwine et al., "Analysis of gene expression in single live neurons" Proc Natl Acad Sci U S A 1992, 89, 3010-3014.
Morris et al., "Transcriptome Analysis of Single Cells" J. Vis. Exp. 2011, 50, e2634.
Grzybowski et al., "Synthesis and antibody-mediated detection of oligonucleotides containing multiple 2,4-dinitrophenyl reporter groups" Nucl. Acids Res. 1993, 21, 1705-1712.
Aujard et al., "o-Nitrobenzyl Photolabile Protecting Groups with Red-Shifted Absorption:Syntheses and Uncaging Cross-Sections for One- and Two-Photon Excitation" 2006, Chemistry—Eur. J., 12: 6865-6879.
Badaeva et al., "Effect of deprotonation on absorption and emission spectra of Ru(II)-bpy complexes functionalized with carboxyl groups" 2010, Phys. Chem. Chem. Phys. 12: 8902-8913.
Balzani et al., "Photochemistry and photophysics of Ru(II)polypyridine complexes in the Bologna group. From early studies to recent developments" 2001, Coord. Chem. Rev. 211: 97-115.
Del Mármol et al., "A Ruthenium-Rhodamine Complex as an Activatable Fluorescent Probe" 2010, Anal. Chem. 82: 6259-6264.
Kanemoto et al., "Spatial Distributions of GABA Receptors and Local Inhibition of Ca2+ Transients Studied with GABA Uncaging in the Dendrites of CA1 Pyramidal Neurons" 2011, PLoS ONE, 6: e22652.
Nikolenko et al, "Two-Photon Mapping of Neural Circuits" 2011, Cold Spring Harbor Protocols, 2011: 496-498.
Nikolenko et al., "Two-photon uncaging of neurochemicals using inorganic metal complexes" 2005, Chem. Commun. 2005: 1752-1754.
Ramírez et al., "Role of Ruthenium Oxidation States in Ligand-to-Ligand Charge Transfer Processes" 2012, Inorg.Chem. 51: 1261-1268.
Rial Verde et al., "Photorelease of GABA with visible light using an inorganic caging group" 2008, Front. Neur. Circ. 2" 1-8.
Salassa et al., "Mechanism of Ligand Photodissociation in Photoactivable [Ru(bpy)2L2]2+ Complexes: A Density Functional Theory Study" 2008, J. Am. Chem. Soc. 130: 9590-9597.
Salassa et al., "Ligand-Selective Photodissociation from [Ru(bpy)(4AP)4]2+: a Spectroscopic and Computational Study", 2009, Inorg. Chem.48: 1469-1481.
Salierno et al., "Caged Amino Acids for Visible☐Light Photodelivery" 2008, Eur. J. Inorg. Chem. 2008: 1125.
Singh et al., "Photoinitiated DNA Binding by cis-[Ru(bpy)2(NH3)2]2+" 2004, Inorg. Chem. 43: 7260-7262.
Wilker et al., "Substrates for Rapid Delivery of Electrons and Holes to Buried Active Sites in Proteins" 1999, Angew. Chem. Int. Ed. 38: 89-92.
Matsuzaki et al., "Two-photon uncaging of γ-aminobutyric acid in intact brain tissue" 2010, Nat Chem Biol, 6: 255-257.
Kolb et al., "Click Chemistry: Diverse Chemical Function from a Few Good Reactions" 2001, Angew Chem Int Ed., 40: 2004-2021.
Chambers et al., "Cryptophane Xenon-129 Nuclear Magnetic Resonance Biosensors Targeting Human Carbonic Anhydrase" 2009, J. Am. Chem. Soc., 131: 563-569.
Hill et al., "Thermodynamics of Xenon Binding to Cryptophane in Water and Human Plasma" 2007, J. Am. Chem. Soc. 129: 9262-9263.
Hill et al., "Substituent Effects on Xenon Binding Affinity and Solution Behavior of Water-Soluble Cryptophanes" 2009, J. Am. Chem. Soc., 131, 3069-3077.
Seward et al., "Cell-compatible, integrin-targeted cryptophane-129XeNMR biosensors" 2011, Chem. Sci., 2: 1103-1110.

(56) References Cited

OTHER PUBLICATIONS

Baron et al., "Click Chemistry on a Ruthenium Polypyridine Complex. An Efficient and Versatile Synthetic Route for the Synthesis of Photoactive Modular Assemblies" 2012, Inorg. Chem., 51: 5985-5987.

Seward et al., "Peptide-Mediated Cellular Uptake of Cryptophane" 2008, Bioconjug. Chem., 19: 2129-2135.

Blidner et al., 2008, "Photoinduced RNA interference using DMNPE-caged 2'-deoxy-2'-fluoro substituted nucleic acids in vitro and in vivo." Mol Biosyst. 4: 431-440.

\* cited by examiner

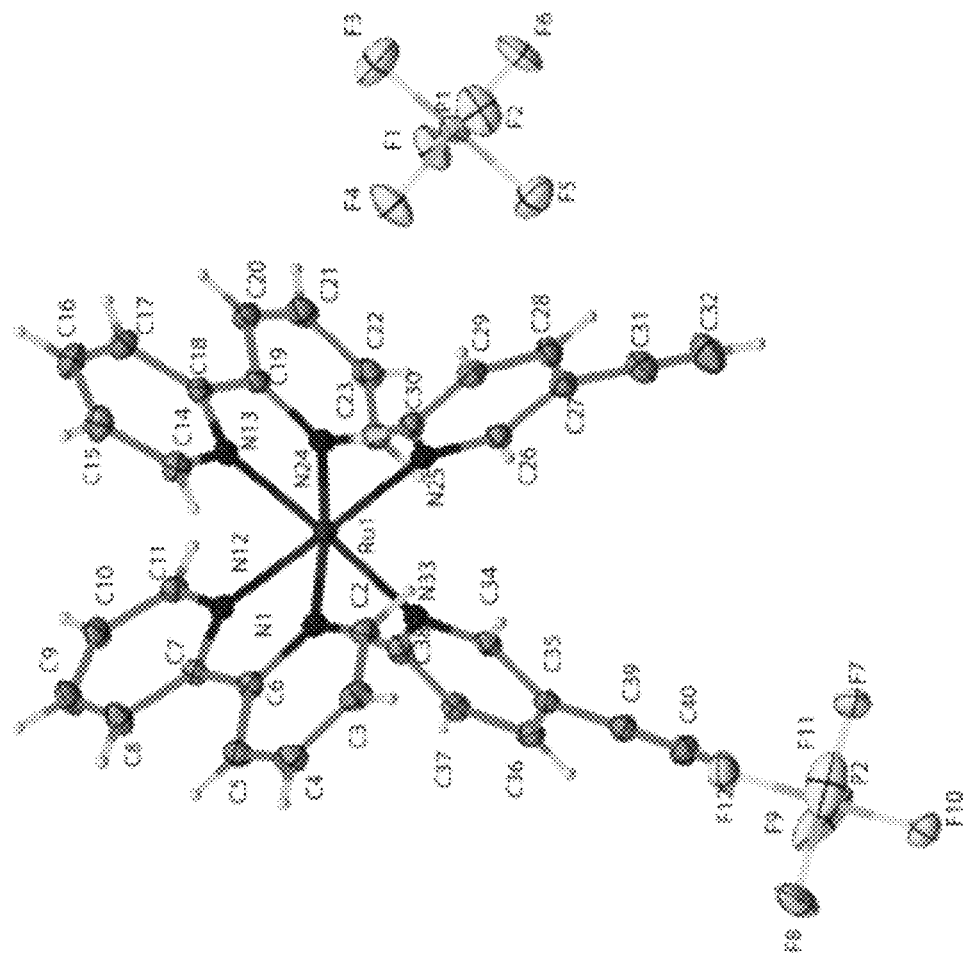
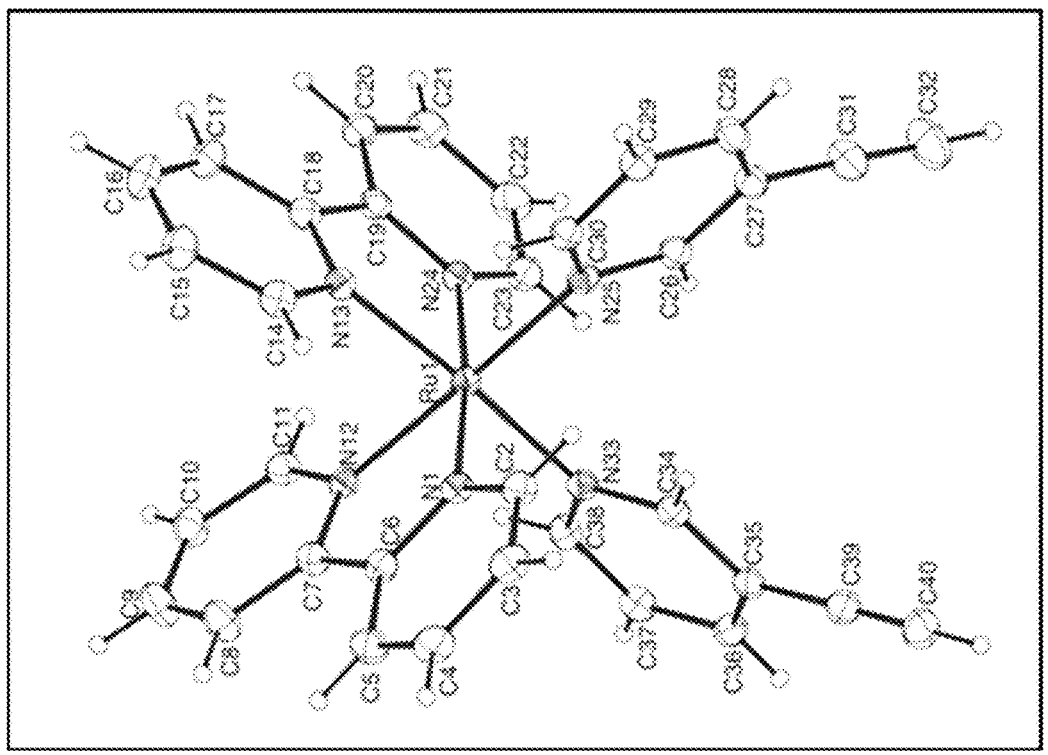
Figure 3

A

B
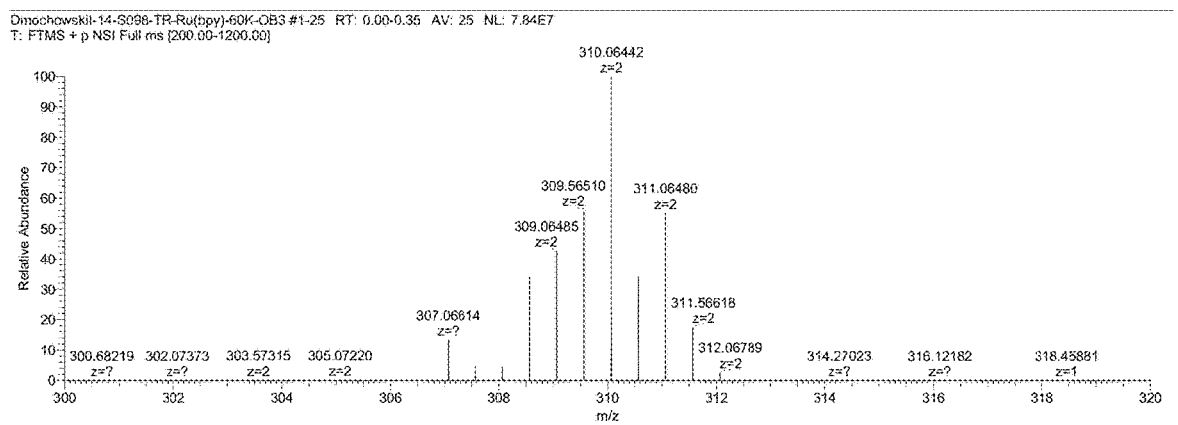
C
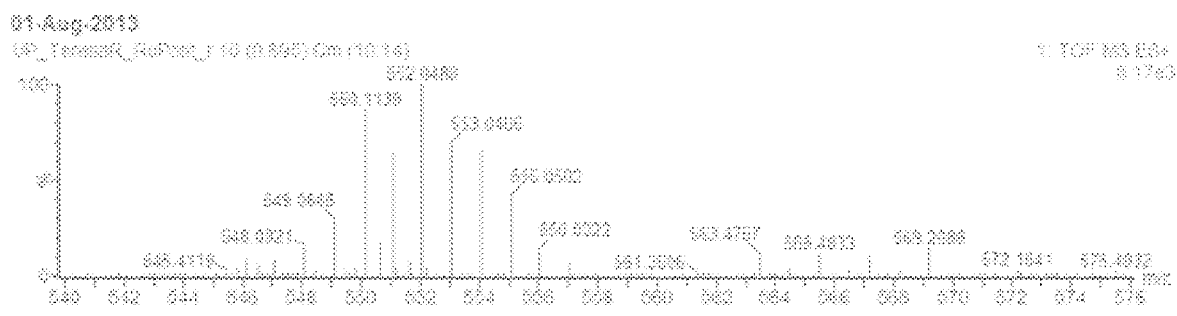
Figure 4

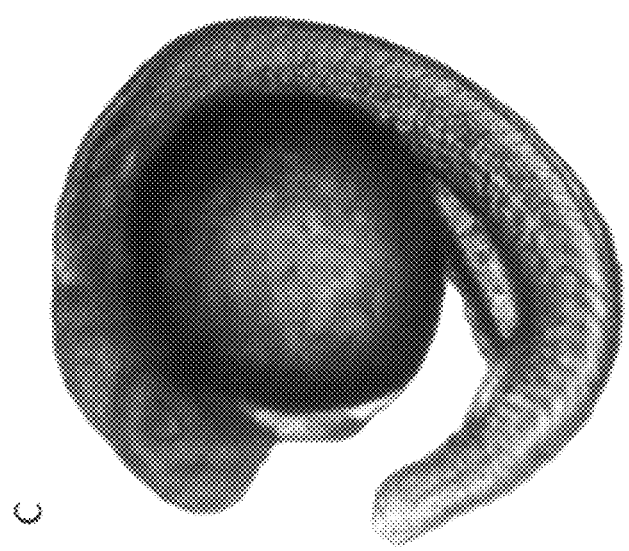
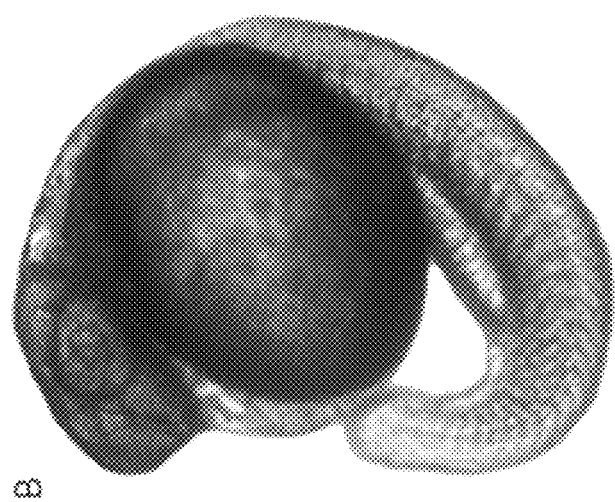
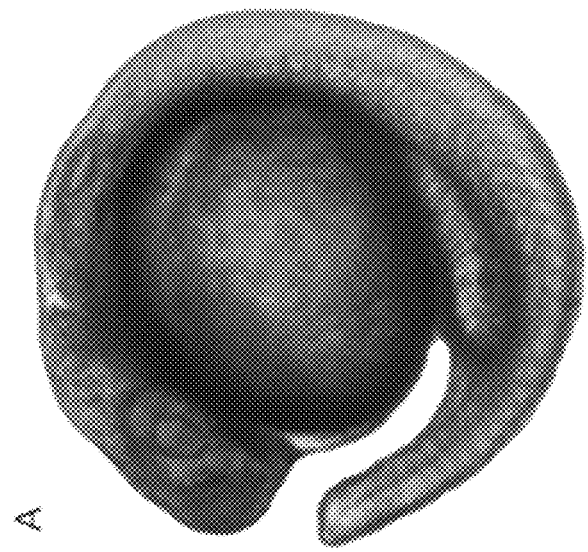
Figure 31

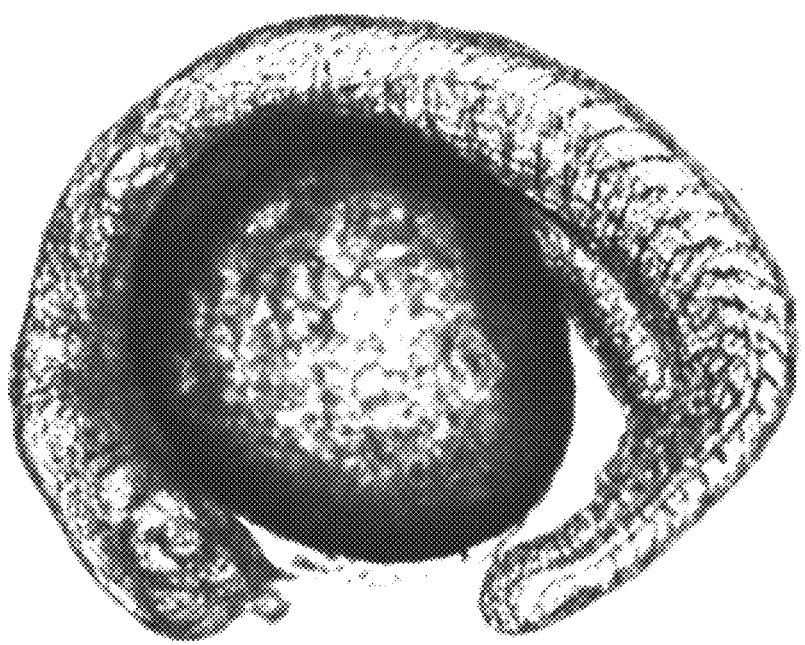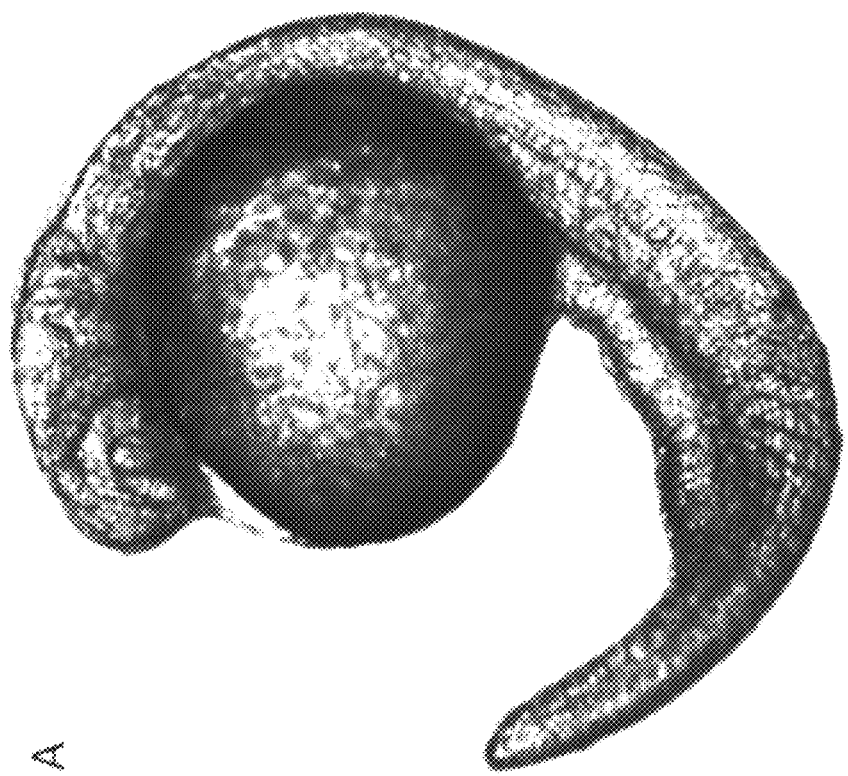
Figure 32

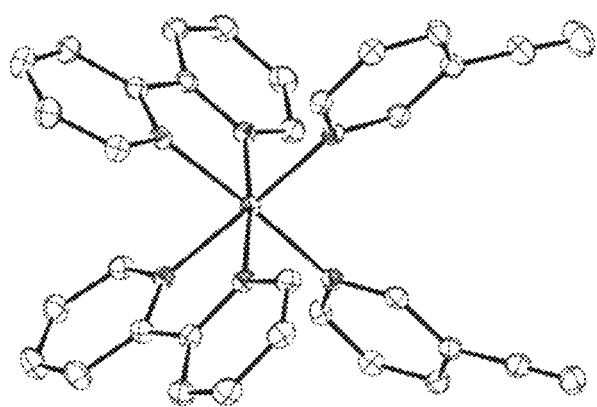
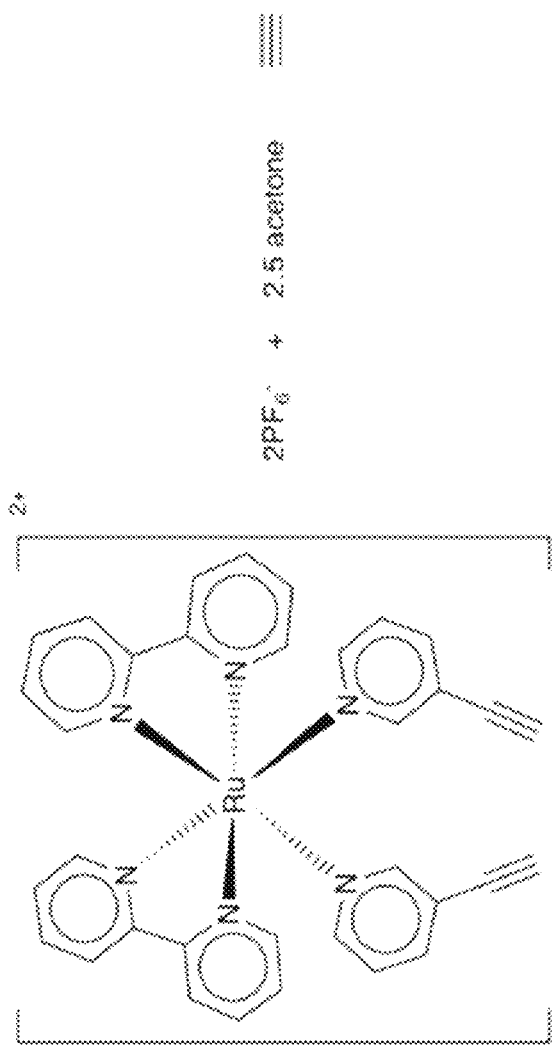
Figure 33

SEQUENCE LISTING

```
<160> NUMBER OF SEQ ID NOS: 10

<210> SEQ ID NO 1
<211> LENGTH: 25
<212> TYPE: DNA
<213> ORGANISM: Artificial sequence
<220> FEATURE:
<223> OTHER INFORMATION: chemically synthesized

<400> SEQUENCE: 1
gacttgaggc aggcatattt ccgat                                        25

<210> SEQ ID NO 2
<211> LENGTH: 25
<212> TYPE: DNA
<213> ORGANISM: Artificial sequence
<220> FEATURE:
<223> OTHER INFORMATION: chemically synthesized

<400> SEQUENCE: 2
```
atcggaaata tgcctgcctc aagtc                                                25

<210> SEQ ID NO 3
<211> LENGTH: 37
<212> TYPE: DNA
<213> ORGANISM: Artificial sequence
<220> FEATURE:
<223> OTHER INFORMATION: chemically synthesized
<220> FEATURE:
<221> NAME/KEY: misc_binding
<222> LOCATION: (1)..(1)
<223> OTHER INFORMATION: 6-FAM
<220> FEATURE:
<221> NAME/KEY: misc_binding
<222> LOCATION: (37)..(37)
<223> OTHER INFORMATION: BHQ1

<400> SEQUENCE: 3
ccacccatcg gaaatatgcc tgcctcaagt cgggtgg                                    37

<210> SEQ ID NO 4
<211> LENGTH: 25
<212> TYPE: DNA
<213> ORGANISM: Artificial sequence
<220> FEATURE:
<223> OTHER INFORMATION: chemically synthesized

<400> SEQUENCE: 4
atccacagca gccctccat catcc                                                  25

<210> SEQ ID NO 5
<211> LENGTH: 25
<212> TYPE: DNA
<213> ORGANISM: Artificial sequence
<220> FEATURE:
<223> OTHER INFORMATION: chemically synthesized

<400> SEQUENCE: 5
ggatgatgga ggggctgctg tggat                                                 25

<210> SEQ ID NO 6
<211> LENGTH: 37
<212> TYPE: DNA
<213> ORGANISM: Artificial sequence
<220> FEATURE:
<223> OTHER INFORMATION: chemically synthesized
<220> FEATURE:
<221> NAME/KEY: misc_binding
<222> LOCATION: (1)..(1)
<223> OTHER INFORMATION: 6FAM
<220> FEATURE:
<221> NAME/KEY: misc_binding
<222> LOCATION: (37)..(37)
<223> OTHER INFORMATION: BHQ1

<400> SEQUENCE: 6
cgggcgggat gatggagggg ctgctgtgga tcgcccg                                    37

<210> SEQ ID NO 7
<211> LENGTH: 25
<212> TYPE: DNA
<213> ORGANISM: Artificial sequence
<220> FEATURE:
<223> OTHER INFORMATION: chemically synthesized

<400> SEQUENCE: 7
agcttgagat aagtccgacg atcct                                                 25

```
<210> SEQ ID NO 8
<211> LENGTH: 25
<212> TYPE: DNA
<213> ORGANISM: Artificial sequence
<220> FEATURE:
<223> OTHER INFORMATION: chemically synthesized

<400> SEQUENCE: 8
aggatcgtcg gacttatctc aagct                                         25

<210> SEQ ID NO 9
<211> LENGTH: 25
<212> TYPE: DNA
<213> ORGANISM: Artificial sequence
<220> FEATURE:
<223> OTHER INFORMATION: chemically synthesized

<400> SEQUENCE: 9
cctcttacct cagttacaat ttata                                         25

<210> SEQ ID NO 10
<211> LENGTH: 25
<212> TYPE: DNA
<213> ORGANISM: Artificial sequence
<220> FEATURE:
<223> OTHER INFORMATION: chemically synthesized

<400> SEQUENCE: 10
acgcaggcta tggtgagcaa gggcg                                         25
```

RUTHENIUM-BASED PHOTOLINKERS AND METHODS OF USE

CROSS-REFERENCE TO RELATED APPLICATIONS

This application is the U.S. national phase application filed under 35 U.S.C. § 371 claiming benefit to International Patent Application No. PCT/US15/43548, filed Aug. 4, 2015, which is entitled to priority under 35 U.S.C. § 119(e) to U.S. provisional application Nos. 62/033,007, filed Aug. 4, 2014 and 62/035,410, filed Aug. 9, 2014, the disclosures of which are incorporated herein by reference in their entirety.

STATEMENT REGARDING FEDERALLY SPONSORED RESEARCH OR DEVELOPMENT

This invention was made with government support under RO1 GM083030 awarded by the National Institute of Health. The government has certain rights in the invention.

BACKGROUND OF THE INVENTION

Photochemical methods for regulating the structure, function, and/or localization of molecular species enable the manipulation of advanced materials (e.g., silicon computer chips) as well as complex biological systems. For example, channelrhodopsin—a single component, light-activated cation channel protein from algae—was co-opted in the development of pioneering optogenetic approaches for manipulating the activity of specific neurons and controlling animal behavior (Boyden et al., 2005, Nat. Neurosci. 8:1263-1268). More generally, "caged" molecules (Young and Dieters, 2007, Org. Biomol. Chem. 5:999-1005), whose latent biological activity can be revealed with light, have been widely adopted, particularly for the study of amino acids (Saliemo et al., 2008, Eur. J. Inorg. Chem. 2008:1125-1128), peptides (Gatterdam et al., 2014, Angew. Chem. Int. Ed. Engl. 53:5680-5684), neurotransmitters (Ellis-Davies, 2013, Beilstein J. Org. Chem. 9:64-73), and metal ions (Ellis-Davies, 2008, Chem. Rev. 108:1603-1613). In each case, photoactivation with high spatiotemporal control can be achieved using a focused laser beam of suitable wavelength. Less investigated are caged oligonucleotides, despite the central roles played by DNA and RNA in biology, and the tantalizing potential for being able to turn genes "on" or "off" with light. Synthetic challenges of site-specifically incorporating one or more photolabile moieties within a large oligonucleotide, and limitations arising from the available near-UV-activatible caging moieties, have slowed such development.

A particular focus for caged oligo development has been antisense morpholinos (MOs), which are commonly used to block mRNA translation and modify pre-mRNA splicing in a variety of model organisms, including mouse, zebrafish, frog, sea urchin, and chick (Eisen and Smith, 2008, Development 135:1735-1743). Initial caged antisense oligos (Tang and Dmochowski, 2006, Angew. Chem., Int. Ed. 45:3523-3526; Tang and Dmochowski, 2007, Mol. BioSyst. 3:100-110; Tang et al., 2007, J. Am. Chem. Soc. 129:11000-11001; Ouyang et al., 2009, J. Am. Chem. Soc. 131:13255-13269; Shestopalov and Chen, 2011, Methods Cell Biol. 104:151-172; Shestopalov et al., 2007, Nat. Chem. Biol. 3:650-651; Tomasini et al., 2009, Genesis 47:736-743) employed a complementary sense strand and photocleavable linker. Deiters et al. subsequently presented caged MOs where multiple caged nucleotide monomers were incorporated during solid-phase synthesis (Dieters et al., 2010, J. Am. Chem. Soc. 132:15644-15650). In this example, MO-mRNA hybridization was sterically blocked until the caging groups were released from the nucleobases (Dieters et al., 2010, J. Am. Chem. Soc. 132:15644-15650). A newer design strategy (Yamazoe et al., 2012, Angew. Chem., Int. Ed. 51:6908-6911; Wang et al., 2012, Nucleic Acids Res. 40:11155-11162; Wu et al., 2013, Nucleic Acids Res. 41:677-686) has involved linking the 5' and 3' ends with a photocleavable moiety. The covalent linkage enforces the closed circular conformation, which prevents efficient MO hybridization to target mRNA until photocleavage restores the linear, biologically active MO. All of these approaches employed an organic photocleavable linker, such as o-nitrobenzyl or hydroxycoumarin, which yielded optimally to near-UV irradiation (Ando et al., 2001, Nat. Genet. 28:317-325).

To expand in vivo applications using caged oligos, there is need for synthetically versatile photolinkers that can be activated at visible or near-IR wavelengths as near-UV light has poor tissue penetration and can be toxic at high exposure levels (Pawley, in Handbook of Biological Confocal Microscopy, $3^{rd}$ ed.; Springer, 2006; Jayakumar et al., 2012, Proc. Natl. Acad. Sci. U.S.A. 8483-8488; Stoien and Wang, 1974, Proc. Natl. Acad. Sci. U.S.A. 71:3961-3965). The Deiters and Chen labs recently advanced this concept by employing a red-shifted organic caging moiety, [7-(diethylamino)coumarin-4-yl]-methyl (DEACM) (Yamazoe et al., 2014, Angew. Chem., Int. Ed. 53:10114-10118). By co-injecting zebrafish embryos with 470 nm responsive DEACM-caged MO targeting flh and 365 nm responsive 2-nitrobenzyl-caged MO targeting spt, discrete spatiotemporal control was retained over each gene. Previous strategies include the use of near-IR-to-UV upconversion nanoparticles to achieve siRNA photoactivation in cells and tissues (Jayakumar et al., 2012, Proc. Natl. Acad. Sci. U.S.A. 8483-8488), however, this approach limits the potential for multiplexing experiments involving two (or more) orthogonally caged compounds.

Ruthenium complexes of the general type $[Ru(bipyridine)_2(X)_2]^{2+}$, where X=amine (Zayat et al., 2006, Inorg. Chem. 45:1728-1731), nitrile (Gamer et al., 2011, Inorg. Chem. 50:9213-9215), pyridine (Zayat et al., 2003, J. Am. Chem. Soc. 125:882-883), or thioether (Gamer et al., 2011, Inorg. Chem. 50:4384-4391) ligands, have been shown to undergo facile X ligand exchange with solvent upon irradiation with visible one-photon or near-IR two-photon excitation (Araya et al., 2013, ACS Chem. Neurosci. 4:1163-1167). Biologically active small molecules can be directly ligated to the $Ru^{2+}$ center, and then released with visible light (Zayat et al., 2013, Philos. Trans. R. Soc., A 371: 20120330). In 2003 Etchenique and co-workers first applied this Ru-ligand exchange property by caging a potassium channel blocker, 4-aminopyridine (Zayat et al., 2003, J. Am. Chem. Soc. 125:882-883), and have since caged several neurotransmitters. (Saliemo et al, 2008, Eur. J. Inorg. Chem. 2008:1125-1128; Fino et al., 2009, Front. Neural Circuits 3:1-9; Filevich and Etchenique, 2013, Photochem. Photobiol. Sci. 12:1565-1570). More recently, ruthenium polypyridyl complexes have been investigated for their potential as photodynamic drugs (Albani et al., 2013, J. Phys. Chem. A 117:13885-13892; Albani et al., 2014, Photochem. Photobiol. Sci. 13:272-280).

Thus there is a need in the art for improved photosensitive molecules. The present invention satisfies this unmet need.

SUMMARY OF THE INVENTION

The present invention includes a composition comprising at least one ruthenium-based photolinker compound of formula (II):

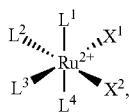

(II)

wherein in formula (II):
$L^1$, $L^2$, $L^3$, and $L^4$ are each independently a ligand; and
$X^1$ and $X^2$ are each independently a photolabile ligand having a reactive moiety.

In one embodiment, $X^1$ and $X^2$ are each independently selected from the group consisting of 3-ethynylpyridine, 3-(bromomethyl)pyridine, maleimide, nicotinaldehyde, 1-(4-(pyridin-3-yl)-1H-1,2,3-triazol-1-yl)ethanone, 4-pentynenitrile, and 4-aminobutyne. In another embodiment, $L^1$ and $L^2$ are joined to form a first bidentate ligand and $L^3$ and $L^4$ are joined to form a second bidentate ligand, further wherein the first bidentate ligand and the second bidentate ligand are selected from the group consisting of 2,2'-bipyridyl (bpy) and biquinoline. In another embodiment, $L^1$, $L^2$, and $L^3$ are joined to form a tridentate ligand, further wherein the tridentate ligand is 2,2':6',2''-terpyridine. In another embodiment, $L^4$ is a fluorophore. In another embodiment, the compound formula (II) is selected from the group consisting of [Ru(bipyridine)$_2$(3-ethynyl-pyridine)$_2$]$^{2+}$, Ru(bipyridine)$_2$(3-ethynylpyridine)$_2$Cl$_2$, Ru(bipyridine)$_2$(3-ethynylpyridine)$_2$(PF$_6$)$_2$, [Ru(biquinoline)$_2$(4-pentynenitrile)$_2$]$^{2+}$, Ru(biquinoline)$_2$(4-pentynenitrile)$_2$Cl$_2$, Ru(biquinoline)$_2$(4-pentynenitrile)$_2$(PF$_6$)$_2$, [Ru(bipyridine)$_2$(4-aminobutyne)$_2$]$^{2+}$, [Ru(bipyridine)$_2$(4-pentynenitrile)$_2$]$^{2+}$, [Ru(bipyridine)$_2$(nicotinaldehyde)$_2$]$^{2+}$, [Ru(bipyridine)$_2$(1-(4-(pyridin-3-yl)-1H-1,2,3-triazol-1-yl)ethanone)$_2$]$^{2+}$, [Ru(bipyridine)$_2$(3-(bromomethyl)pyridine)$_2$]$^{2+}$, [Ru(bipyridine)$_2$(maleimide)$_2$]$^{2+}$, a salt thereof, and any combinations thereof. In another embodiment, the compound of formula (II) is a compound of formula (III):

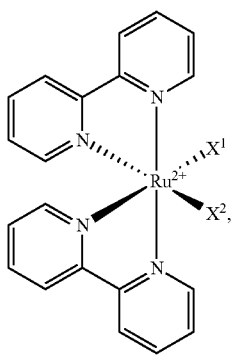

(III)

wherein in formula (III):
$X^1$ and $X^2$ are each independently a photolabile ligand having a reactive moiety.

In one embodiment, the composition comprises a caged molecule, wherein the caged molecule comprises at least one active domain conjugated to the at least one ruthenium-based photolinker compound. In another embodiment, the active domain is at least one selected from the group consisting of a peptide, protein, antibody, oligonucleotide, polynucleotide, morpholino, antisense polynucleotide, probe, oligosaccharide, polysaccharide, and a small molecule. In another embodiment, the composition comprises a circular caged molecule comprising the at least one ruthenium-based photolinker compound and the active domain, wherein a first end of the active domain is conjugated to a first photolabile ligand of the compound and wherein a second end of the active domain is conjugated elsewhere on the compound. In another embodiment, the second end of the active domain is conjugated to a second photolabile ligand of the compound. In another embodiment, the active domain is an oligonucleotide comprising a nucleic acid sequence that is substantially complementary to a target molecule. In another embodiment, the oligonucleotide comprises at least one intramolecular base pair. In another embodiment, the active domain is a morpholino comprising a nucleobase sequence substantially complementary to a target nucleic acid. In another embodiment, the caged molecule further comprises a cell penetrating domain. In another embodiment, the caged molecule further comprises a label.

The present invention also includes a method of manipulating the expression of a gene in a cell. The method includes the step of administering to the cell a composition comprising a caged molecule comprising an active domain conjugated to the at least one ruthenium-based photolinker compound of formula (II)

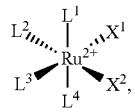

(II)

wherein in formula (II):
$L^1$, $L^2$, $L^3$, and $L^4$ are each independently a ligand; and
$X^1$ and $X^2$ are each independently a photolabile ligand having a reactive moiety.

In one embodiment, the method further includes the step of irradiating the cell thereby cleaving the ruthenium-based photolinker compound and exposing the active domain. In another embodiment, the active domain is at least one selected from the group consisting of a peptide, protein, antibody, oligonucleotide, polynucleotide, morpholino, antisense polynucleotide, probe, oligosaccharide, polysaccharide, and a small molecule. In another embodiment, the active domain is an oligonucleotide comprising a nucleic acid sequence that is substantially complementary to a target molecule. In another embodiment, the oligonucleotide comprises at least one intramolecular base pair. In another embodiment, the active domain is a morpholino comprising a nucleobase sequence substantially complementary to a target nucleic acid.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 3 is a series of ORTEP drawings of RuBEP with 50% probability of thermal ellipsoids.

FIGS. 4A-4C, depicts spectra of electrospray mass spectrometry of [RuBEP](PF$_6$)$_2$+/−light. The sample was prepared in a stock solution of 50% acetonitrile and 0.1% formic acid, and directly infused as nanospray onto a Thermo ORBI trap XL mass spectrometer at 60 K resolution. FIG. 4A is a spectrum depicting the expected mass of [RuBEP](PF$_6$)$_2$ before irradiation (expected mass=620.13 Da). FIG. 4B is a spectrum depicting a doubly charged peak observed for [RuBEP]$^{2+}$ (310.06m/z). FIG. 4C is a spectrum depicting Hi-Res MS after irradiation (3 min, 14 mW/cm$^2$ LED). The expected mass is 552.02 Da for [Ru(bpy)$_2$(3EP)OH].

FIGS. 5A-5B, depicts $^1$H NMR spectra in D$_2$O of pre- and post-photolysis of RuBEP. FIG. 5A is a $^1$H NMR spectrum in D$_2$O depicting the pre-photolysis of RuBEP. FIG. 5B is a $^1$H NMR spectrum in D$_2$O depicting the post-photolysis of RuBEP. The appearance of a second major peak in the alkyne region indicates that one ligand exchanged with solvent (D$_2$O), and one remained coordinated to ruthenium. The loss of symmetry in the remaining complex gives a more complex peak pattern in the aromatic region.

FIGS. 6A-6B, depicts the change in absorbance as one 3EP ligand is dissociated from RuBEP. FIG. 6A is a scheme depicting the disassociation of one 3EP ligand from RuBEP, which is then replaced by a solvent molecule. Irradiation of RuBEP with a 450 nm laser induced ligand exchange. FIG. 6B is a table depicting change in the UV-Vis spectrum of RuBEP upon 450-nm focal irradiation. UV-Vis absorption spectroscopy showed isosbestic points at 364, 385, and 450 nm, consistent with the exchange of one 3EP ligand for solvent (water).

FIGS. 10A-10D, depicts HPLC traces for N$_3$-DNA, Ru-DNA, N$_3$-DNA-N$_3$, and Ru-cDNA. A gradient of increasing acetonitrile in 0.05 M triethylammonium acetate in H$_2$O was used with a Zorbax reverse-phase C18 column. The column was heated to 40° C. during purification. Product elution times are indicated on HPLC traces. FIG. 10A is an HPLC trace of N$_3$-DNA. FIG. 10B is an HPLC trace of Ru-DNA (linear). FIG. 10C is an HPLC trace of N$_3$-DNA-N$_3$. FIG. 10D is an HPLC trace of Ru-cDNA (circular).

FIGS. 13A-13C, depicts click reactions with chd morpholino. FIG. 13A is an image of a gel demonstrating the results of a 15% native PAGE gel-shift assay with 25 pmol of complementary 25mer DNA (lane 1) and DNA hybridized to 25 pmol chd-MO (lane 2), Ru-cMO-chd (lane 3) and its subsequent photo-product (lane 4). FIG. 13B is an exemplary structure of a MO+DNA hybrid. FIG. 13C is an exemplary structure of a circular MO.

FIGS. 16A-16E, depicts representative images of 24-28 hpf zebrafish embryos, showing different degrees of chd knockdown phenotype, depending on experimental protocol. FIG. 16A is an image of a wildtype embryo, uninjected. FIG. 16B is an image of a Ru-cMO-chd zebrafish, incubated in the dark, showing normal development. FIG. 16C is an image of a Ru-cMO-chd zebrafish irradiated for 5 min at 1 hpf with 450-nm light, showing chd knockdown phenotype. FIG. 16D is an image of a Bis-azido chd-MO zebrafish showing chd knockdown phenotype. All embryos were injected at 1-cell stage. FIG. 16E is a graph demonstrating Ru-MO-ntl in vivo data. MO Control: Zebrafish embryos were injected at the 1-cell stage with 0.25 mM ntl-MO and imaged at 24 hpf. Ru-MO-ntl: Zebrafish embryos were injected at the 1-cell stage with 0.25 mM Ru-MO-ntl. Half of the embryos were irradiated (450 nm, 14 mW/cm$^2$, 5 min) at 1 hpf, while the other half were incubated in the dark. Embryos were scored for phenotype at 24 hpf and compared to wildtype. Decreased uncaging efficiency of the caged Ru-MO-ntl is attributed to decreased purity of the injected Ru-MO.

FIG. 25A-25B, depicts exemplary compounds of the invention. FIG. 25A depicts the structures of Ru420, RuBEP, and Ru530. FIG. 25B is a graph depicting experimental data demonstrating that compounds Ru420, RuBEP, and Ru530 can be selectively activated.

FIGS. 27A-27B, depicts exemplary caged molecules of the invention. FIG. 27A depicts the structure of an exemplary caged molecule with a linear oligonucleotide. FIG. 27B depicts the structure of an exemplary caged molecule with an oligonucleotide having intramolecular base pairing to form a stem-loop structure.

FIGS. 28A-28B, depicts images of gels of exemplary circular Ru-DNA molecules produced using click reactions. FIG. 28A is an image of a gel of an exemplary circular Ru-DNA molecule produced using a linear oligonucleotide. The main product (the bottom band) is contaminated significantly by extensive polymerization. FIG. 28B is an image of a gel of an exemplary circular Ru-DNA molecule produced using an oligonucleotide having intramolecular base pairing to form a stem-loop structure. The main product appears as two bands, due to the secondary structure, and lacks polymerization.

FIG. 31, comprising FIGS. 31A-31C, is a series of images of zebrafish embryos treated with RuBEP+/−light in vivo with control. FIG. 31A is an image depicting an uninjected wildtype zebrafish embryo. FIG. 31B is an image depicting a zebrafish embryo injected at the 1-cell stage with 500 μM RuBEP and incubated in the dark. FIG. 31C is an image depicting a zebrafish embryo injected at the 1-cell stage with 500 μM RuBEP and irradiated (450 nm, 14 mW/cm$^2$, 15 min). All embryos showed normal development (n>50).

FIG. 32, comprising FIGS. 32A-32B, is a series of images of zebrafish embryos treated with scramble morpholino in vivo with control. FIG. 32A is an image depicting an uninjected wildtype zebrafish embryo. FIG. 32B is an image depicting a zebrafish embryo injected at the 1-cell stage with 500 μM standard scramble control morpholino (see sequence, Table S9). All embryos showed normal development (n>50).

FIG. 33 depicts the crystal structure of [RuBEP](PF$_6$)$_2$.

DETAILED DESCRIPTION

Figure 1:
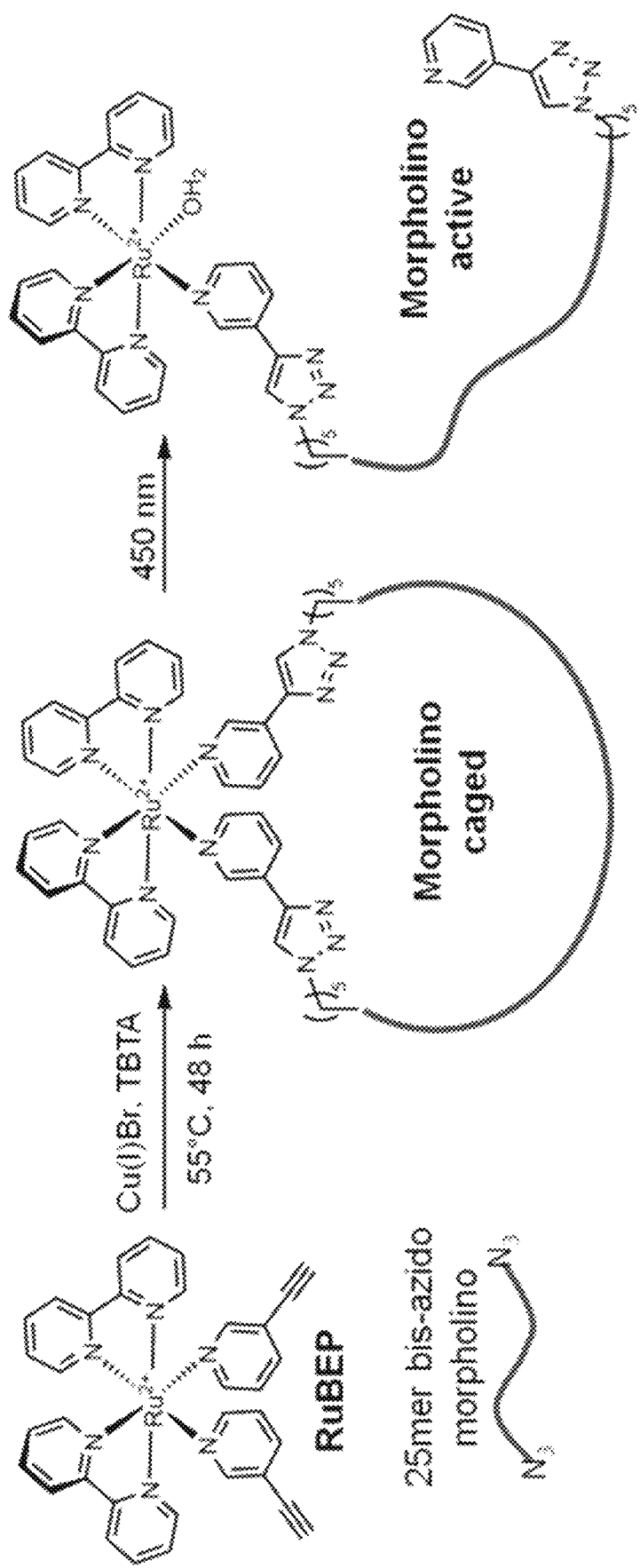
FIG. 1 is an exemplary synthetic scheme of photolinker Ru(bpy)$_2$(3-ethynyl pyr)$_2$, which is abbreviated herein as RuBEP. The conjugation of RuBEP is shown with 25mer bis-azido morpholino (MO) to form "caged" antisense MO, and subsequent 450 nm irradiation to restore biologically active MO.

The present invention provides ruthenium-based photolinker compounds, caged molecules comprising the ruthenium-based photolinker compounds, and methods of use. In certain aspects, the compositions disclosed herein comprise an active domain conjugated to a ruthenium-based photolinker, such that irradiation of the photolinker exposes the active domain.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

"Amplification" refers to any means by which a polynucleotide sequence is copied and thus expanded into a larger number of polynucleotide molecules, e.g., by reverse transcription, polymerase chain reaction, and ligase chain reaction, among other methods.

"Antisense" refers to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Binding" is used herein to mean that a first moiety interacts with a second moiety.

"Biological sample," as that term is used herein, means a sample obtained from a single-cellular or multi-cellular organism that can be used to assess the level of expression of a nucleic acid, the level of a protein present, or both. Such a sample includes, but is not limited to, a cell, a blood sample, a neural tissue sample, a brain sample, and a cerebrospinal fluid sample.

"Caged" is used herein to describe a molecule that is in an inactive state. For example, in certain embodiments, a caged molecule has a conformation that prevents the activity of the molecule. In contrast, an "uncaged" molecule describes a molecule in an active state. In certain embodiments, an uncaged molecule has a conformation that allows the activity of the molecule. In certain embodiments, an uncaged molecule is generated from a corresponding caged molecule. For example, in one embodiment, a caged molecule is activated to become an uncaged molecule.

A "cell penetrating domain" is used herein to refer to a domain that facilitates the entry of said domain, along with any molecule associated with the domain, across one or more membranes to the interior of a cell.

A "cell penetrating peptide" is used herein to refer to a polypeptide that facilitates the entry of said polypeptide, along with any molecule associated with the polypeptide, across one or more membranes to the interior of a cell.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A "fluid medium" or "fluid media" is used herein to refer to a form of matter, such as air, liquid, solid or plasma, preferably liquid, that is capable of flowing.

An "isolated cell" refers to a cell which has been separated from other components and/or cells which naturally accompany the isolated cell in a tissue or organism.

An "isolated nucleic acid" refers to a nucleic acid (or a segment or fragment thereof) which has been separated from sequences which flank it in a naturally occurring state, e.g., a RNA fragment which has been removed from the sequences which are normally adjacent to the fragment. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

"Linker" refers to one or more atoms comprising a chain connecting a nucleic acid analog to a moiety such as a peptide, nucleotide, label, modifier, stabilizing group, or the like.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

"Nucleic acid analogs" are structurally modified, polymeric analogs of DNA and RNA made by chemical synthesis from monomeric nucleotide analog units, and possessing some of the qualities and properties associated with nucleic acids. PNA and phosphorothioate oligonucleotides are examples of two of many nucleic acid analogs known in the art. "Watson/Crick base-pairing" and "Watson/Crick complementarity" refer to the pattern of specific pairs of nucleotides, and analogs thereof, that bind together through hydrogen bonds, e.g. A pairs with T and U, and G pairs with C. The act of specific base-pairing is "hybridization" or "hybridizing". A hybrid forms when two, or more, complementary strands of nucleic acids or nucleic acid analogs undergo base-pairing.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "photoreactive label" refers to a label that becomes chemically active upon irradiation of the label with light energy. Light energy useful for activating such labels includes, but is not limited to, visible light, ultraviolet (UV) light, infrared (IR) light, among others. An activated label may contain a free radical, or other highly reactive group, and may be reactive with an adjacent molecule. A photoreactive label is "incorporated into" a nucleic acid analog or a cell-penetrating peptide when the label is attached to, incorporated within, integrated into, or linked to the nucleic acid analog or the cell-penetrating peptide. This includes coupling of a label to the terminus of a nucleic acid analog or a cell-penetrating peptide as well as incorporating the label into a nucleic acid analog or a cell-penetrating peptide by including a nucleobase or amino acid analog that contains such a label.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As applied to a protein, a "fragment" of a polypeptide, protein or an antigen, is about 6 amino acids in length. More preferably, the fragment of a protein is about 8 amino acids, even more preferably, at least about 10, yet more preferably, at least about 15, even more preferably, at least about 20, yet more preferably, at least about 30, even more preferably, about 40, and more preferably, at least about 50, more preferably, at least about 60, yet more preferably, at least about 70, even more preferably, at least about 80, and more preferably, at least about 100 amino acids in length amino acids in length, and any and all integers there between.

A "genomic DNA" is a DNA strand which has a nucleotide sequence homologous with a gene as it exists in the natural host. By way of example, a fragment of a chromosome is a genomic DNA.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5'TATGGC3' share 50% homology.

In addition, when the terms "homology" or "identity" are used herein to refer to the nucleic acids and proteins, it should be construed to be applied to homology or identity at both the nucleic acid and the amino acid sequence levels.

"Conjugate" or "conjugated" refer to a covalent, ionic, or hydrophobic interaction whereby the moieties of a molecule are held together and preserved in proximity.

"Chimera" as used herein refers to an oligonucleotide including one or more nucleotide and one or more nucleotide analog units. The monomer units are linked through phosphodiester and phosphodiester analog linkages.

"Phosphodiester analog" or "internucleotide analog" refer to analogs of natural phosphodiester 3',5'-internucleotide linkages differing in their composition and/or location of attachment to a nucleotide, including but not limited to 2',5'-linkage, 3',3'-linkage, 5',5' linkage, methyl phosphonate, alkylated phosphotriester, 3'-N-phosphoramidate, and non-bridging N-substituted phosphoramidate.

The term "2'-modified RNA" means a nucleic acid analog containing one or more ribonucleotides in which a 2' position on a sugar bears a substituent replacing a hydroxyl. As an example, 2'-O-alkyl RNA comprises a nucleic acid analog containing one or more ribonucleotides in which a 2' position on a sugar consists of the moiety —OR where R is lower alkyl, such as, but not limited to, a methyl or ethyl moiety (Sproat, 1994, Protocols for Oligonucleotides and Analogs, Humana Press).

The terms "permeant" and "permeable" refer to the ability of a construct of the present invention to pass through a cellular membrane, a cell compartment membrane, or a nuclear membrane, or ascribed as characteristics of the susceptibility of membranes to have constructs pass through them (Alberts et al., 1989, Molecular Biology of the Cell, 2nd Ed., Garland Publishing, New York).

"Detection" refers to detecting, observing, or measuring a construct on the basis of the properties of a detection label.

The term "labile" refers to a bond or bonds in a molecule with the potentiality of being cleaved by reagents, enzymes, or constituents of a cell.

The term "ligand" as used herein means a molecular group that is associated with a central metal atom.

As used herein, a "solvate" of a molecule refers to a complex between the molecule and a finite number of solvent molecules. In one embodiment, the solvate is a solid isolated from solution by precipitation or crystallization. In another embodiment, the solvate is a hydrate.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to ruthenium-based photolinkers, compositions comprising ruthenium-based photolinkers, and their methods of use. In one embodiment, the present invention provides a ruthenium-based photolinker compound comprising two or more potentially photolabile ligands. In one embodiment, the two or more photolabile groups each comprise a reactive moiety, used for the attachment of a cargo. In certain embodiments, the cargo comprises a biomolecule, such as a peptide, protein, antibody, oligonucleotide, polynucleotide, morpholino, antisense polynucleotide, probe, oligosaccharide, polysaccharide, small molecule or the like. The ruthenium-based photolinkers described herein allow for the caging of the cargo, which may then be selectively released or exposed upon irradiation of the photolinker.

The present invention is at least partly based upon the design and discovery of ruthenium-based photolinkers that are ultrafast, releasing or exposing a cargo faster than about 20 ns after irradiation. Further, it is described herein, that only slightly different structures allow for the development of different versions of photolinkers which display photosensitivity to varied wavelengths, thereby allowing for multiplexed or longitudinal uses.

In one embodiment, the invention comprises a composition comprising a ruthenium-based photolinker compound comprising two or more photolabile ligands and at least one active domain conjugated to at least one of the photolabile ligands. In certain embodiments, the composition is a caged molecule, wherein irradiation of the photolinker releases or exposes the active domain. In one aspect, the composition is a circular caged molecule, where a first end of the active domain is conjugated to a first photolabile ligand, while a second end of the active domain is conjugated elsewhere on the photolinker. For example, in one embodiment, the second end of the active domain is conjugated to a second photolabile ligand. In certain embodiments, irradiation of the linker cleaves one of the photolabile ligands thereby linearizing the circular caged molecule and thus exposing the active domain. In one embodiment, irradiation of the linker cleaves two of the photolabile ligands thereby releasing the active domain. In certain embodiments, the active domain comprises a biomolecule, such as a peptide, protein, antibody, oligonucleotide, polynucleotide, morpholino, antisense polynucleotide, probe, oligosaccharide, polysaccharide, small molecule or the like.

In one embodiment, the invention provides a composition comprising a caged morpholino antisense oligonucleotide for modifying or manipulating expression of a gene of interest, wherein the morpholino comprises a ruthenium-based photolinker. In one embodiment, the invention provides a composition comprising a photosensitive protein scaffold or supramolecular complex, wherein the scaffold or complex comprises one or more ruthenium-based photolinkers.

In one embodiment, the invention provides methods of regulating gene expression comprising administering to a cell or subcellular compartment a caged morpholino molecule, wherein the molecule comprises a ruthenium-based photolinker. In one embodiment, the method comprises activating the caged morpholino molecule by irradiating the photolinker in the cell or subcellular compartment, thereby exposing the antisense morpholino. The exposed antisense morpholino is thus allowed to hybridize to a nucleic acid molecule of the cell or subcellular compartment, thereby manipulating the expression, transcription, or translation of the nucleic acid molecule.

In one embodiment, the invention provides a method of capturing one or more nucleic acid molecules of a cell or subcellular compartment, comprising administering to the cell or subcellular compartment a caged molecule comprising a ruthenium-based photolinker and an antisense oligonucleotide. In one embodiment, the method comprises activating the caged molecule irradiating the photolinker in the cell or subcellular compartment, thereby exposing the antisense oligonucleotide. The exposed antisense oligonucleotide hybridizes to a nucleic acid molecule of the cell or cell compartment to form a complex. In one embodiment, the method comprises isolating the complex from the cell or subcellular compartment. In certain embodiments, the method is used to capture a specific target nucleic acid, as defined by the sequence of the antisense oligonucleotide. In one embodiment, the method is used to capture all mRNA by allowing the antisense oligonucleotide to bind to the polyA tails of mRNA.

Compounds

The compounds of the present invention may be synthesized using techniques well-known in the art of organic and inorganic synthesis. The starting materials and intermediates required for the synthesis may be obtained from commercial sources or synthesized according to methods known to those skilled in the art.

In one aspect, the compound of the invention is a compound of formula (I), or a salt, solvate, or N-oxide thereof:

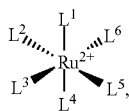

(I)

wherein in formula (I):

$L^1, L^2, L^3, L^4, L^5$, and $L^6$ are each independently a ligand, wherein at least two of $L^1, L^2, L^3, L^4, L^5$, and $L^6$ are each independently a potentially photolabile ligand having a reactive moiety.

In some embodiments, the compound of the invention comprises two potentially photolabile ligands having a reactive moiety, which may be the same or different. In one embodiment, the two photolabile ligands are cis to each other. In another embodiment, the two photolabile ligands are trans to each other. In one embodiment, $L^5$ is photolabile ligand, and $L^6$ is photolabile ligand, wherein each of the photolabile ligands may be the same or different.

The photolabile ligands of the present invention are capable of undergoing ligand exchange with solvent upon irradiation. In one embodiment, the irradiation is visible one-photon (1P) excitation. In another embodiment, the irradiation is near-IR two-photon (2P) excitation. Varying the photolabile ligand permits excitation and activation of compounds at different wavelengths. In a non-limiting example, compounds that are activated at different wavelengths may be useful for studying the interactions of two or more genes, proteins, or other biological systems. Any ligand that is capable of undergoing ligand exchange with solvent upon irradiation and has a reactive moiety may be used as a photolabile ligand in the invention, as would be understood by one skilled in the art. Non-limiting examples of photolabile ligands include amines, nitriles, pyridines, thioethers, pyridines, maleimides, imidazoles, triazoles, triaryl phosphines, trialkyl phosphines, and thiocyanates.

In another aspect of the invention, the photolabile ligands have a reactive moiety. The reactive moiety reacts with a reactive site on the desired biomolecule, resulting in the conjugation of the compound to the biomolecule. Direct $Ru^{2+}$ ligand substitution chemistry typically requires elevated temperatures (>70° C.) over several hours, which makes the conjugation reaction between the compound and the biomolecule extremely difficult to perform. Instead, the compounds of the present invention are already installed with photolabile ligands having a reactive moiety, permitting conjugation between the compound and the biomolecule under mild conditions.

Any reactive moiety that permits conjugation of the compound to the biomolecule under mild conditions may be used in the invention, as would be understood by one skilled in the art. In a non-limiting example, the reactive moiety is an alkyne, and the reactive site on the biomolecule is an azide. Under mild conditions, the alkyne and azide undergo a [3+2] cyclization reaction to produce a triazole, thereby conjugating the compound to the biomolecule via the triazole moiety. It should be understood that the reactive moiety and the reactive site on the biomolecule are interchangeable, permitting an equivalent conjugation reaction wherein the functionality between the reactive moiety and the reactive site on the biomolecule have been switched. In another non-limiting example, representing the reverse of the previous example, the reactive moiety is an azide, and the reactive site on the biomolecule is an alkyne, permitting a [3+2] cyclization reaction under mild conditions to produce a triazole to conjugate the compound to the biomolecule. In another non-limiting example, the reactive moiety is an alkyl or aryl bromide or a maleimide. These reactive moieties can react with a sulfur group or an amine on the biomolecule in order to conjugate the compound to the biomolecule. In addition, alkyl or aryl bromides and maleimides form covalent bonds with cysteine residues in proteins under mild conditions, resulting in a photolinker that can enforce secondary structure, then release ultrafast for protein structure studies. Other non-limiting examples of reactive moieties include carbonyl groups such as aldehydes or ketones. Aldehydes and ketones may undergo reaction with amines on the biomolecule, thereby conjugating the compound to the biomolecule. Compounds with aldehydes or ketones may be used as IR probes in 2D IR studies or femtosecond transient IR experiments, or to study the photophysical properties of the linker following conjugation or photorelease. In one embodiment, at least two photolabile ligands having a reactive moiety are selected from the group consisting of 3-ethynylpyridine, 3-(bromomethyl)pyridine, maleimide, nicotinaldehyde, 1-(4-(pyridin-3-yl)-1H-1,2,3-triazol-1-yl)ethanone, 4-pentynenitrile, and 4-aminobutyne.

In one embodiment, any of $L^1$, $L^2$, $L^3$, $L^4$, $L^5$, and $L^6$ are monodentate ligands. Non-limiting examples of monodentate ligands include nitriles, such as acetonitrile and propionitrile, sulfoxides, such as dimethylsulfoxide, amides such as dimethylformamide, ethers, such as tetrahydrofuran, water, ammonia, amines, piperidine, pyridine, pyrazine, sulfur-donor ligands such as thioethers, thiols, thioureas, or phosphorous donor ligands such as triaryl or trialkyl phosphines, or arsenic donor ligands.

In some embodiments, any of $L^1$, $L^2$, $L^3$, $L^4$, $L^5$, and $L^6$ are joined to form multi dentate ligands, such as bi dentate, tridentate, or tetradentate ligands. In one embodiment, any two of $L^1$, $L^2$, $L^3$, $L^4$, $L^5$, and $L^6$ are joined to form a bidentate ligand. As will be known to those of ordinary skill in the art, a bidentate ligand generally includes species which have two sites capable of binding to a metal center. For example, the bidentate ligand may comprise two heteroatoms that coordinate the metal center, or a heteroatom and an anionic carbon atom that coordinate the metal center. Examples of bidentate ligands include, but are not limited to, N,N' bidentate ligands, N,O bidentate ligands, and O,O' bidentate ligands. Non-limiting examples of N,N' bidentate ligands include diamines, such as ethylene diamine, bipyridyl such as 2,2'-bipyridyl (bpy), bridged bipyridyl, such as phenanthroline, bisquinoline, and the like. Non-limiting examples of N, O bidentate ligands include amino acids and Schiff base type groups. Non-limiting examples of O, O' bidentate ligands include dicarboxylate, 2-hydroxyacetophenone, acetylacetone type and catechol type groups. Other non-limiting examples of bidentate ligands include diimines, pyridylimines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments.

In some embodiments, the compound of the present invention comprises one bidentate ligand. In one embodiment, $L^1$ and $L^2$ are joined to form a bidentate ligand. In another embodiment, $L^3$ and $L^4$ are joined to form a bidentate ligand. In another embodiment, $L^5$ and $L^6$ are joined to form a bidentate ligand. In other embodiments, the compound of the invention comprises two bidentate ligands. In one embodiment, the two bidentate ligands are the same. In another embodiment, the two bidentate ligands are different. In one embodiment, both $L^1$ and $L^2$ are joined to form a first bidentate ligand and $L^3$ and $L^4$ are joined to form a second bidentate ligand. In one embodiment, both the bidentate ligand formed by $L^1$ and $L^2$ and the bidentate ligand formed by $L^3$ and $L^4$ are 2,2'-bipyridyl (bpy). In another embodiment, both the bidentate ligand formed by $L^1$ and $L^2$ and the bidentate ligand formed by $L^3$ and $L^4$ are biquinoline.

In one embodiment, any three of $L^1$, $L^2$, $L^3$, $L^4$, $L^5$, and $L^6$ are joined to form a tridentate ligand. As will be known to those of ordinary skill in the art, a tridentate ligand generally includes species which have three sites capable of binding to a metal center. For example, the tridentate ligand may comprise three heteroatoms that coordinate the metal center, or a combination of heteroatom(s) and anionic carbon atom(s) that coordinate the metal center. Non-limiting examples of tridentate ligands include 2,5-diiminopyridyl ligands, tripyridyl moieties such as 2,2':6',2"-terpyridine, triimidazoyl moieties, and tris pyrazoyl moieties. In one embodiment, $L^1$, $L^2$, and $L^3$ are joined to form a tridentate ligand. In one embodiment, the tridentate ligand formed by $L^1$, $L^2$, and $L^3$ is 2,2':6',2"-terpyridine.

In one embodiment, any four of $L^1$, $L^2$, $L^3$, $L^4$, $L^5$, and $L^6$ are joined to form a tetradentate ligand. As will be known to those of ordinary skill in the art, a tetradentate ligand generally includes species which have four sites capable of binding to a metal center. For example, the tetradentate ligand may comprise four heteroatoms that coordinate the metal center, or a combination of heteroatom(s) and anionic carbon atom(s) that coordinate the metal center. A non-limiting example of a tetradentate ligand is triethylenetetramine. In one embodiment, $L^1$, $L^2$, $L^3$, and $L^4$ are joined to form a tetradentate ligand.

In one aspect of the invention, the ruthenium metal of the compounds of the present invention has an oxidation state of +2 (Ru(II)). In some embodiments, the complex contains at least one counterion Z of appropriate charge to render the overall charge of the complex neutral. Suitable counterions for cationic complexes, include but are not limited to, halide ($F^-$, $Cl^-$, $Br^-$ or $I^-$), $SO_4^{-2}$, $PF_6^-$, $BPh_4^-$, $ClO_4^-$ and $NO_3^-$. In one embodiment, Z is selected from the group consisting of $Cl^-$ and $PF_6$.

In some embodiments, at least one of $L^1$, $L^2$, $L^3$, $L^4$, $L^5$, and $L^6$ is a fluorophore. Any fluorophore with a suitable excitation or emission wavelength may be used in the invention, as would be understood by one skilled in the art. Non-limiting examples of fluorophores include acridine orange, anthracene ring, allophycocyanin, BODIPY, cyanines, coumarin, Edans, Eosin, Erythrosin, fluorescamine, fluorescein, FAM (carboxyfluorescein), HEX (hexachlorofluorescein), JOE (6-carboxy-4',5'-dichloro-2',7'-dimethoxyfluorescein), Oregon Green, phycocyanin, phycoerythrin, rhodamine, ROX (carboxy-X-rhodamine), TAMRA (carboxytetramethylrhodamine), TET (tetrachloro-fluorescein), Texas Red, tetramethylrhodamine, and xanthines. In one embodiment, the fluorophore has an excitation wavelength between about 550 nm and about 700 nm. In one embodiment, $L^4$ is a fluorophore. In another embodiment, $L^4$ is a fluorophore and $L^1$, $L^2$, and $L^3$ are joined to form a tridentate ligand.

In another aspect, the compound of the invention is a compound of formula (II), or a salt, solvate, or N-oxide thereof:

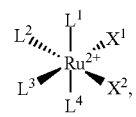

(II)

wherein in formula (II):

$L^1$, $L^2$, $L^3$, and $L^4$ are each independently a ligand; and
$X^1$ and $X^2$ are each independently a potentially photolabile ligand having a reactive moiety.

In one embodiment, $X^1$ and $X^2$ are each independently selected from the group consisting of 3-ethynylpyridine, 3-(bromomethyl)pyridine, maleimide, nicotinaldehyde, 1-(4-(pyridin-3-yl)-1H-1,2,3-triazol-1-yl)ethanone, 4-pentynenitrile, and 4-aminobutyne. In one embodiment, $X^1$ and $X^2$ are each 3-ethynylpyridine. In another embodiment, $X^1$ and $X^2$ are each 4-pentynenitrile.

In one embodiment, $L^1$ and $L^2$ are joined to form a first bidentate ligand and $L^3$ and $L^4$ are joined to form a second bidentate ligand. In another embodiment, the first bidentate ligand and the second bidentate ligand are selected from the group consisting of 2,2'-bipyridyl (bpy) and 2,2'-biquinoline (biq). In one embodiment, the first bidentate ligand and the second bidentate ligand are 2,2'-bipyridyl (bpy). In another embodiment, the first bidentate ligand and the second bidentate ligand are 2,2'-biquinoline.

In one embodiment, $L^1$, $L^2$, and C are joined to form a tridentate ligand. In one embodiment, the tridentate ligand is 2,2':6',2''-terpyridine.

In one embodiment, $L^1$, $L^2$, and $L^3$ are joined to form a tridentate ligand, and $L^4$ is a fluorophore. In one embodiment, the tridentate ligand is 2,2':6',2''-terpyridine.

In one embodiment, the compound of the invention comprises a counterion. In one embodiment, the counterion is selected from the group consisting of $Cl^-$ and $PF_6^-$.

In one embodiment, the compound of the invention is selected from the group consisting of [Ru(bipyridine)$_2$(3-ethynylpyridine)$_2$]$^{2+}$, Ru(bipyridine)$_2$(3-ethynylpyridine)$_2$Cl$_2$, Ru(bipyridine)$_2$(3-ethynylpyridine)$_2$(PF$_6$)$_2$, [Ru(biquinoline)$_2$(4-pentynenitrile)$_2$]$^{2+}$, Ru(biquinoline)$_2$(4-pentynenitrile)$_2$Cl$_2$, Ru(biquinoline)$_2$(4-pentynenitrile)$_2$(PF$_6$)$_2$, [Ru(bipyridine)$_2$(4-aminobutyne)$_2$]$^{2+}$, [Ru(bipyridine)$_2$(4-pentynenitrile)$_2$]$^{2+}$, [Ru(bipyridine)$_2$(nicotinaldehyde)$_2$]$^{2+}$, [Ru(bipyridine)$_2$(1-(4-(pyridin-3-yl)-1H-1,2,3-triazol-1-yl) ethanone)$_2$]$^{2+}$, [Ru(bipyridine)$_2$(3-(bromomethyl) pyridine)$_2$]$^{2+}$, [Ru(bipyridine)$_2$(maleimide)$_2$]$^{2+}$, a salt thereof, and any combinations thereof.

In another aspect, the compound of the invention is a compound of formula (III), or a salt, solvate, or N-oxide thereof:

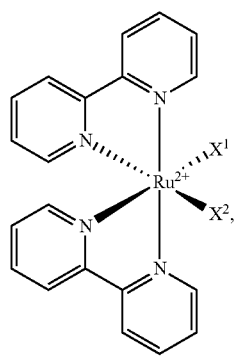

(III)

wherein in formula (III):

$X^1$ and $X^2$ are each independently a photolabile ligand having a reactive moiety.

In one embodiment, $X^1$ and $X^2$ are each independently selected from the group consisting of 3-ethynylpyridine, 3-(bromomethyl)pyridine, maleimide, nicotinaldehyde, 1-(4-(pyridin-3-yl)-1H-1,2,3-triazol-1-yl)ethanone, 4-pentynenitrile, and 4-aminobutyne. In one embodiment, $X^1$ and $X^2$ are each 3-ethynylpyridine.

In one embodiment, the compound comprises a counterion. In one embodiment, the counterion is selected from the group consisting of $Cl^-$ and $PF_6^-$.

In one embodiment, the compound of the invention is selected from the group consisting of [Ru(bipyridine)$_2$(3-ethynyl-pyridine)$_2$]$^{2+}$, Ru(bipyridine)$_2$(3-ethynylpyridine)$_2$Cl$_2$ and Ru(bipyridine)$_2$(3-ethynylpyridine)$_2$(PF$_6$)$_2$.

Preparation of the Compounds of the Invention

Compounds of formulae (I)-(III) may be prepared by the general schemes described herein, using the synthetic methods known by those skilled in the art. The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomers is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one aspect, compounds useful in the invention are synthesized by the reaction of a dichlororuthinium compound with silver trifluoromethanesulfonate (silver triflate) to form a ruthenium-triflate complex. The triflate group can then be displaced by reacting the ruthenium-triflate complex with desired ligands to form compounds of the invention.

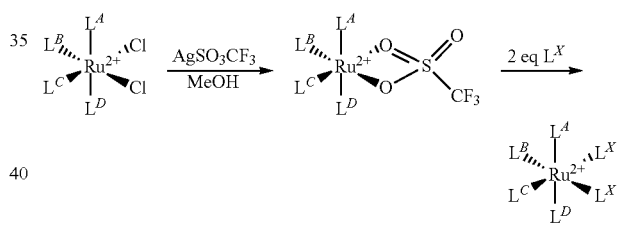

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water and ethanol. In another embodiment, the compounds described herein exist in unsolvated form.

In one embodiment, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$.

Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

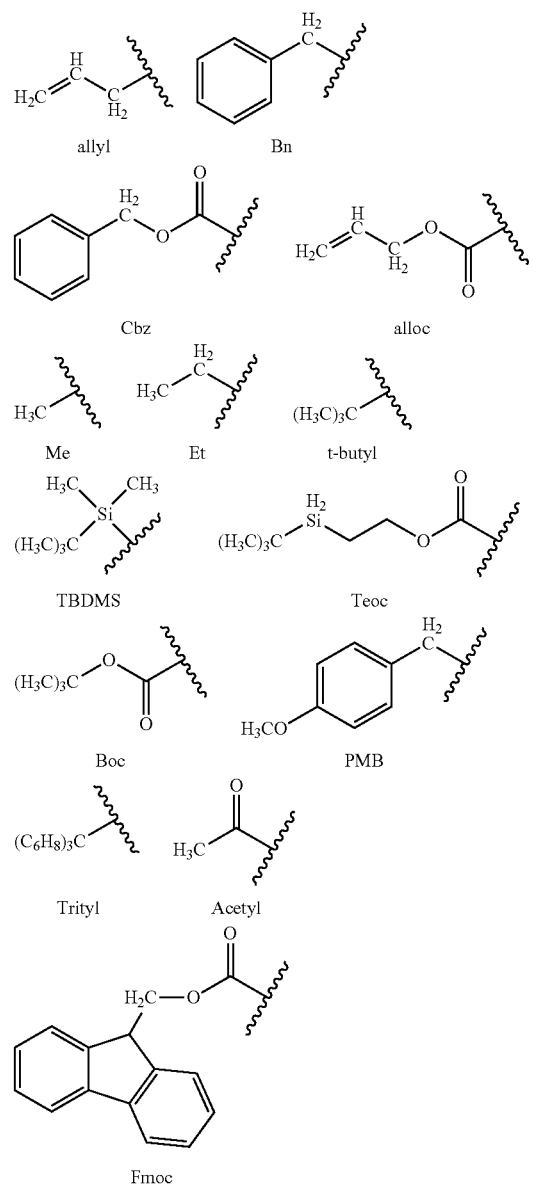

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Caged Molecules and Methods of Use

In one embodiment, the invention comprises a composition comprising a ruthenium-based photolinker compound comprising two or more photolabile ligands and at least one active domain conjugated to at least one of the photolabile ligands. In certain embodiments, the composition is a caged molecule, wherein irradiation of the photolinker releases or exposes the active domain. In certain embodiments, the active domain comprises a biomolecule, such as a peptide, protein, antibody, oligonucleotide, polynucleotide, morpholino, antisense polynucleotide, probe, oligosaccharide, polysaccharide, small molecule or the like. Exemplary caged molecules are described in the concurrently filed application of Eberwine et al. This application incorporates by reference the concurrently filed application of Jim Eberwine, Ivan J. Dmochowski, Sean B. Yeldell, Julianne C. Griepenburg, Teresa L. Rapp, Jennifer M. Singh, Jaehee Lee, and Jai-Yoon Sul, titled "Transcriptome In Vivo Analysis (TIVA) and Transcriptome In Situ Analysis (TISA)," App. No. PCT/US2015/043581, filed August 4$^{th}$, 2015.

In one aspect, the composition is a circular caged molecule, where a first end of the active domain is conjugated to a first photolabile ligand, while a second end of the active domain is conjugated elsewhere on the photolinker. For example, in one embodiment, the second end of the active domain is conjugated to a second photolabile ligand. In certain embodiments, irradiation of the linker cleaves one of the photolabile ligands thereby linearizing the circular caged molecule and thus exposing the active domain. In one embodiment, irradiation of the linker cleaves two of the photolabile ligands thereby releasing the active domain.

In one embodiment, the active domain of the composition comprises a reactive moiety at one or both ends, which react with a reactive moiety of the photolabile ligand, as defined elsewhere herein. For example, in certain instances, the active domain is conjugated to a photolabile ligand of ruthenium-based photolinker via click chemistry. For example, in certain embodiments, the active domain is terminated at both ends with an azide to allow for reaction with the photolabile ligand of the ruthenium-based photolinker. The reactive moieties of the active domain may be added to the active domain using any suitable chemistry or reaction as known in the art. Exemplary methods of attaching a reactive moiety to exemplary active domains are discussed elsewhere herein.

In one embodiment, the caged molecule comprises a cell penetrating domain, including for example a peptide, small molecule, or the like, which allows entry of the caged molecule into a cell or subcellular compartment. In another embodiment, the caged molecule does not comprise a cell penetrating domain, but rather gains entry to a cell or subcellular compartment by use of a suitable delivery vehicle, such as a lipid, lipososme, micelle, nanoparticle, and the like.

In one embodiment, the caged molecule comprises a tag or label that allows detection of the caged molecule. For example, in certain embodiments, the caged molecule comprises a fluorescent label or enzymatic label that allows visualization of the molecule. In certain embodiments, the molecule comprises a label, such as a biotin tag, His tag, and the like. Other exemplary labels useful in the present invention includes, but should not be limited to, avidin, streptavidin, dinitrophenyl, acridine, fluorescein, rhodamine, cyanine (such as Cy3 and Cy5, among others), digoxigenin, an intercalator, a minor-groove binder, a chemiluminescent precursor, selenium, cadmium, labels useful in quantum dot technology, and the like.

The active domain of the caged molecule may, when released or exposed, exhibits the native functionality of the domain. For example, the active domain may be a therapeutic agent, diagnostic agent, research tool, probe, or the like.

In one embodiment, the active domain is a therapeutic agent, which, when released or exposed, exhibits its therapeutic activity. The therapeutic agent may be, for example, a peptide, protein, antibody, oligonucleotide, polynucleotide, morpholino, antisense polynucleotide, probe, oligosaccharide, polysaccharide, small molecule or the like. Thus, the caged molecule provides for the selective tuning of a therapeutic activity of a therapeutic agent, controlled via the irradiation or activation of the ruthenium-based photolinker.

In one embodiment, the active domain is a diagnostic agent, which when released or exposed, exhibits its diagnostic activity. The diagnostic agent may be, for example, a peptide, protein, antibody, oligonucleotide, polynucleotide, morpholino, antisense polynucleotide, probe, oligosaccharide, polysaccharide, small molecule or the like. Thus, the caged molecule provides for the selective tuning of a diagnostic agent, controlled via the irradiation or activation of the ruthenium-based photolinker. For example, in one embodiment, the diagnostic agent may be uncaged to allow for its binding to a target molecule. In another example, the diagnostic agent may be uncaged to allow the agent to adopt a conformation that allows for its detection.

In one embodiment, the active domain is a research tool. For example, in one embodiment, the active domain is a peptide or protein that is held in an altered conformation in the caged molecule. For example, ruthenium-based photolinkers comprising methyl bromides or maleimides as reactive moieties can form covalent bonds with cysteine residues in quick, easy, and clean reactions. The release or exposure of the active domain, upon irradiation, allows the active domain to adopt it native conformation. Thus, the caged molecule allows for the study of protein or peptide folding.

In one embodiment, the active domain of the caged molecule comprises a peptide. The peptide may be a therapeutic peptide, research tool, peptide probe, or the like. For example, in one embodiment, exposure or release of the peptide allows for the peptide to bind to a target molecule. Upon uncaging, the peptide may be used to modulate the activity of one or more biomolecules, including for example inhibiting or enhancing the activity or expression of a gene or gene product.

The peptide of the present invention may be made using chemical methods. For example, peptides can be synthesized by solid-phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer. The peptide may alternatively be made by recombinant means or by cleavage from a longer polypeptide. The composition of a peptide may be confirmed by amino acid analysis or sequencing. The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

The peptide may comprise one or more unnatural or non-natural amino acids. Non-natural amino acids include, but are not limited to, the D-amino acids, 2,4-diaminobutyric acid, α-amino isobutyric acid, 2-aminoisobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general.

In one embodiment, the caged molecule of the invention comprises an oligonucleotide or polynucleotide molecule. In one embodiment, the oligonucleotide or polynucleotide molecule may be a therapeutic oligonucleotide, research tool, oligonucleotide probe, or the like. For example, in one embodiment, exposure or release of the oligonucleotide allows for the oligonucleotide to bind to a target molecule. Upon uncaging, the oligonucleotide may be used to modulate the activity of one or more biomolecules, including for example inhibiting or enhancing the activity or expression of a gene or gene product. In one embodiment, the oligonucleotide of the composition comprises a nucleic acid sequence that is substantially complementary to a target nucleic acid. For example, in one embodiment, the oligonucleotide is an antisense oligonucleotide. The target nucleic acid may be any form of nucleic acid, including but not limited to DNA and RNA. Exemplary forms of RNA to which the oligonucleotide of the composition may bind include, but are not limited to, microRNAs, lincRNAs, piwi-interacting RNAs, intron-containing RNAs, exonic RNA, fragmented RNA, hnRNAs, poly-A+ mRNA and poly-A− mRNA. In one embodiment, the oligonucleotide hybridizes to a target nucleic acid and inhibits the activity of the target. In one embodiment, the oligonucleotide hybridizes to a target nucleic acid to detect the presence or amount of the target.

As would be understood by those skilled in the art, the oligonucleotide of the caged molecule may be of any suitable length necessary to bind to a target. In certain embodiments, the oligonucleotide comprises 1 or more, 2 or more, 5 or more, 10 or more, 15 or more, 20 or more, 30, or more, or 50 or more nucleotide bases. The oligonucleotide of the composition may be produced using any known methodology known in the art, including being produced recombinantly or synthetically. Generally, the design and synthesis of an oligonucleotide follows conventional teachings. By way of a non-limiting examples, an oligonucleotide is synthesized on an automated, solid-phase DNA synthesizer using phosphoramidite chemistry or on an automated, solid-phase peptide synthesizer.

In certain embodiments, the oligonucleotide of the composition is a nucleic acid analog. For example, in one embodiment, the sugar moiety of at least one of the nucleotides of the nucleic acid analog is modified. In one embodiment, the 2'-position of a nucleoside is modified. Oligonucleotides bearing 2'-modified nucleosides have been studied as ribozymes, nuclease-resistance antisense analogs, and other cellular mechanism probes (Lamond, A., et al., Cell, 58:383-90 (1989); (Goodchild, J., Nucleic Acids Research, 20:4607-12 (1992)). Desirable features of 2'-O-alkyl-oligoribonucleosides include high chemical stability, substantial RNA- and DNA-nuclease resistance (including RNaseH), and increased thermal duplex stability (Ohtsuka, E., et al., U.S. Pat. No. 5,013,830).

In another embodiment, a fraction of the ribonucleotides of a nucleic acid analog are 2'-O-alkylribonucleotides, preferably 2'-O-methyl-ribonucleotides. Additional preferred modified ribonucleotides include 2'-O-allyl-ribonucleotides, ribonucleotides, 2'-halo-ribonucleotides, 2'-O-methoxyethyl-ribonucleotides, 2'-branching group-ribonucleotides, and 2'-O-branching group-ribonucleotides. In one embodiment, the oligonucleotide of the caged molecule of the invention is 2'fluoro RNA.

In one embodiment, at least one of the nucleotides in the nucleic acid analogs includes modified nucleobases. Nucleobase modifications of the invention include, but are not limited to, C-5-alkyl pyrimidine, 2,6-diaminopurine, 2-thiopyrimidine, C-5-propyne pyrimidine, 7-deazapurine, isocytosine and isoguanine, and universal base, which shows diminished base-specific discrimination in a Watson/Crick, base-pairing hybridization interaction, e.g., 3-nitropyrrole (Nichols, R., et al., Nature, 369:492-3 (1994)) and 5-nitroindole (Loakes, D., et al., Nucleic Acids Research, 22:4039-43 (1994)).

In one embodiment, the oligonucleotide may be comprised of at least one intramolecular base pair. Intramolecular base pairing provides a stem-loop structure, as would be understood by one of ordinary skill in the art. The stem-loop design brings the two ends of the oligonucleotide closer together, thereby increasing the efficiency of forming a circular structure, which may further improve caging of the molecule.

In one aspect, the caged molecule described herein is a caged morpholino which may be used for manipulating gene expression. For example, the caged morpholino, may, when uncaged, modulate the expression, transcription, or translation of a nucleic acid molecule of interest. For example, in one embodiment, the composition is an antisense morpholino, where the antisense morpholino has a nucleobase sequence substantially complementary to a target sequence within an RNA or DNA molecule of interest. For example, in certain embodiments, the morpholino hybridizes to a target nucleic acid molecule to block translation of mRNA, interfere with pre-mRNA splicing, block miRNA activity, or the like.

In one embodiment the morpholino has a length of about 5-100 nucleobases. In one embodiment, the morpholino has a length of about 25 nucleobases.

Morpholinos behave like small molecule therapeutics and have an outstanding safety record in multiple clinical trials. Morpholinos are highly specific, stable, effective and non-toxic (Shrewsbury, S. B. (2010) "Preclinical Safety Of A VI-4658, A Phosphorodiamidate Morpholino Oligomer (PMO), Being Developed To Skip Exon 51 In Duchenne Muscular Dystrophy (DMD)," AVI Biopharma, Inc.; Press Release (2011) "Systemic Treatment With AVI-4658 Demonstrates RNA Exon Skipping and Dystrophin Protein Expression in Duchenne Muscular Dystrophy Patients," AVI Biopharma, Inc.). They generally comprise about 20-25 nucleic acid bases linked by an uncharged synthetic backbone. They bind to complementary sequences of RNA by base pairing to prevent processes from happening at the bound sites. They may be targeted to stop the progression of a ribosomal initiation complex toward the start codon of an mRNA, preventing protein translation. They may also be targeted to interfere with pre-mRNA splicing machinery, altering content of mature mRNA.

In certain embodiments, the morpholino oligonucleotides described herein comprise a six member morpholino ring in lieu of the pentose sugar of DNA or RNA:

Additionally, such morpholino oligonucleotides possess a non-ionic backbone, most preferably achieved by replacing the phosphorodiester bonds of DNA or RNA with phosphorodiamidate linkages:

In certain embodiments, the sequences of the morpholino oligonucleotides of the present invention will be designed to be between 10-30 bases long, more preferably, 15-30 bases long, and still more preferably 20-25 bases long. In certain embodiments, the sequence is designed to bind close to an ATG start codon of a target nucleic acid, and to exhibit a Tm of 75° C.-115° C., of 80° C.-100° C., or of 90° C.-110° C. In one embodiment, oligonucleotide will have a % GC content of 40-80%.

In one embodiment, the morpholino is a translation-blocking morpholino. In another embodiment, the morpholino is a splice-modifying morpholino. In one embodiment, the translation-blocking morpholino oligonucleotides are targeted across the start codon. In one embodiment, splice-modifying morpholino oligonucleotides are targeting regions of the pre-mRNA with lower CG content than the 5'-UTR+start of coding region, leading to morpholino oligonucleotides that, in some instances, are likely to be more specific for their intended targets. The splice-modifying morpholino oligonucleotides are targeted to interfere with snRNP binding at intronic sites near the splice junctions.

In one embodiment, the invention provides a method of manipulating the activity or expression of a gene or gene product comprising administering a caged molecule, described herein, to a cell or subcellular region. In one embodiment, the method comprises activating the caged molecule by irradiating the cell or subcellular compartment with light at a wavelength in which the ruthenium-based photolinker is sensitive. The particular wavelength of the irradiation will depend upon the particular ruthenium-based photolinker used in the caged molecule. In certain embodiments, the method comprises contacting the cell with a plurality of different caged molecules, where one or more of the different types having differing sensitivity to different wavelengths and/or differing active domains, thereby allowing multiplexed regulation or manipulation of different genes or gene products.

Delivery of the caged molecule to a cell, tissue, embryo, or organism of interest may be carried out using any suitable methodology. For example, in one embodiment, the molecule comprises a cell penetrating domain that delivers the molecule to cell and/or cell compartment. In one embodiment, the molecule is delivered via a nanoparticle, lipid, liposome, micelle, or the like. In one embodiment, the molecule is delivered via microinjection.

Activation of the caged molecule may be carried out using any suitable wavelength, including, for example wavelengths of the UV, near-UV, visible, near-IR, or IR spectrum.

In one embodiment, the method comprises administering a caged morpholino, described elsewhere herein, to a subject. In certain embodiments, the caged morpholinos are used in a method of treatment to inhibit the expression of one or more genes or gene products, whose activity may be associated with a disease or disorder. The caged morpholinos may also be used in ex vivo or in vitro methods to inhibit the expression of one or more genes or gene products.

The present invention also provides pharmaceutical compositions comprising one or more of the compositions described herein. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

Administration of the compositions of this invention may be carried out, for example, by parenteral, by intravenous, intratumoral, subcutaneous, intramuscular, or intraperitoneal injection, or by infusion or by any other acceptable systemic method.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the HMW-HA or other composition of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxy ethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid.

Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

The present invention also provides methods of identifying nucleic acid molecules in an individual live cell. The method includes the steps of providing a caged molecule of the invention in a caged form into a cell or cell compartment, activating the molecule in the cell or cell compartment under conditions suitable for binding of the antisense oligonucleotide to cellular nucleic acid to form a complex.

In one embodiment, the method comprises isolating the hybridized complex. In one embodiment of the invention, the method includes lysing the cell containing the hybridized complex to form a cell lysate, contacting the cell lysate with a solid support under conditions suitable to allow the hybridized complex to bind to the solid support, and separating the complex from the lysate. In one aspect, the isolating step includes lysing the cell containing the hybridized complex to form a cell lysate, and contacting the cell lysate with a solid support comprising a binding moiety specific for a tag or label of the molecule of the invention. For example, if the tag is biotin, a binding moiety specific for the tag would be streptavidin beads. However, the invention should not be limited to biotin as the tag and streptavidin as the binding moiety thereof. Rather, the invention encompasses the used of any tag and corresponding binding moiety for purposes of isolating the hybridized complex from a cell or cell lysate.

In one embodiment, the caged molecule is administered to the cell via the action of a CPD of the molecule. However, the method is not limited to the use of a CPD. Rather, the method encompasses any method known in the art to deliver the molecule into a cell or cell compartment of interest. For example, in certain embodiments, the molecule is deliverable upon forming a nanoparticle with a lipid, liposome, micelle, or other delivery vehicle. In one embodiment, the molecule is noncovalently complexed with PepFect6 (PF$_6$), derived from the known TP10 cell-penetrating peptide (Andaloussi et al., 2011, Nucleic Acids Res, 39(9): 3972-3987). In one embodiment, the molecule is microinjected into a cell or tissue of interest.

The recipient cell for molecule of the invention may be at least one of any type of cell. A recipient cell may be a eukaryotic cell or a prokaryotic cell. When the cell is a eukaryotic cell, the cell is preferably a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell, the cell is a bacterial cell. A recipient cell may be a differentiated cell and/or a non-dividing cell. The cell may also be a progenitor cell or a stem cell. Preferably, the recipient cell is a tissue-specific cell, more preferably a mammalian tissue-specific cell and more preferably still, a human tissue-specific cell. Non-limiting examples of cells suitable as a recipient cell include epithelial cells, neurons, fibroblasts, embryonic fibroblasts, keratinocytes, adult stem cells, embryonic stem cells, and cardiomyocytes.

The method of the invention may be performed on a cell comprising a cellular process. Such a cellular process includes, but is not limited to, a dendrite, an axon, a microvilli, a cilia, a stereocilia, a process, an astrocytic process, and the like.

The present invention further comprises methods for introducing the molecule of the invention into a live slice of tissue or a live animal. Methods for sustaining the cellular processes in the cells comprising a live slice of tissue are known in the art. As a non-limiting example, live slices can be refrigerated and perfused with natural or artificial fluids, such as artificial spinal fluid, artificial central nervous system fluid, and buffers disclosed elsewhere herein. Methods for the manipulation of live slice cultures are described in, for example, Roelandse, et al. (2004, J. Neuroscience, 24: 7843-7847); and Chen, et al. (2005, Magn. Reson. Med. 53: 69-75).

In one embodiment, activation of the caged molecule of the invention in a cell or cell compartment is accomplished by irradiation of the ruthenium-based photolinker to cleave one or more of the photolabile ligands of the photolinker. For example, exposure to light induces cleavage of one or more of the photolabile ligands of the ruthenium-based photolinker contained in the molecule of the invention. In one embodiment, the method comprises cleaving a single photolabile ligand of a ruthenium-based photolinker of a circular caged molecule, thereby linearizing the molecule and exposing the antisense oligonucleotide.

In certain embodiments, the photolinker is activated by use of any suitable light source capable of delivering light at the wavelength needed to activate the particular linker. For example, in certain embodiments, the light source is a white light source. In one embodiment, the light source is a white light source with a colored filter. In one embodiment, the light source is a UV-light box. In one embodiment, the light is light from a laser source. In certain embodiments, the light is UV-light, visible light, near infrared light, or infrared light. In one embodiment, the light used to cleave the linker has a wavelength of about 350 nm to about 1500 nm. In one embodiment, the ruthenium-based photolinker is designed to be cleaved when exposed to light of a particular wavelength, or range of wavelength. Once the ruthenium-based photolinker is cleaved, the antisense oligonucleotide of the molecule of the invention is available for binding to target cellular nucleic acid. For example, following photolysis, the 2'-fluoro antisense oligonucleotide containing poly T's or poly U's is available for binding to cellular poly A tails.

In one embodiment, the method comprises a multiplexed detection of cellular nucleic acid species by administering to a cell or tissue sample, a plurality of caged molecules, where one or more of the differing types of molecules comprise ruthenium-based photolinkers having different sensitivities to different wavelengths, thereby allowing selective activation of particular caged molecule species. The ruthenium-based photolinkers described herein are easily tuned to be reactive to varying wavelengths, thereby allowing for multiplexed detection.

For example, in certain embodiments, the method allows for multiplexed detection in longitudinal studies of detecting nucleic acid species over a time course in the same cell or subcellular compartment. In one embodiment, the method allows for multiplexed detection of nucleic acid species in different subcellular compartments of a cell. In one embodiment, the method allows for multiplexed detection of nucleic acid species in different cells of a tissue.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Ruthenium-Caged Antisense Morpholinos for Regulating Gene Expression in Zebrafish Embryos Described herein is a visible light-responsive antisense morpholino (MO) oligonucleotide, the first example which was circularized using a ruthenium bis-(3-ethynylpyridine) (Ru(3-EP)$_2$) (RuBEP) photocleavable linker. RuBEP was reacted stoichiometrically with a 25mer DNA or MO oligonucleotide functionalized with 3' and 5' terminal azides, via Cu(I)-mediated [3+2] Huisgen cycloaddition reaction. These results demonstrate a Ru-photolinker amenable to caging oligonucleotides and other large biomolecules, while bypassing the harsh synthetic conditions typically required for ligand substitution at Ru$^{2+}$, and avoiding direct reaction between biomolecules and Ru$^{2+}$. RuBEP-caged circular morpholinos (Ru-cMOs) targeting two early developmental zebrafish genes, chordin and notail, were synthesized and tested in vivo. One-cell-stage zebrafish embryos microinjected with Ru-cMO and incubated in the dark for 24 h developed normally, consistent with caging, whereas irradiation at 450 nm dissociated one 3-ethynylpyridine ligand (Φ=0.33 in air) and uncaged the MO to achieve gene knockdown. As demonstrated, Ru photolinkers provide a versatile method for controlling structure and function of polymeric systems.

Table 1 below identifies compounds of the present invention which are discussed in Example 1 and throughout the specification.

TABLE 1

Compounds of the present invention

| Structure | Name | Compound Name |
|---|---|---|
|  | [Ru(bipyridine)$_2$(3-ethynyl-pyridine)$_2$]$^{2+}$ | RuBEP |

TABLE 1-continued

Compounds of the present invention

| Structure | Name | Compound Name |
| --- | --- | --- |
| 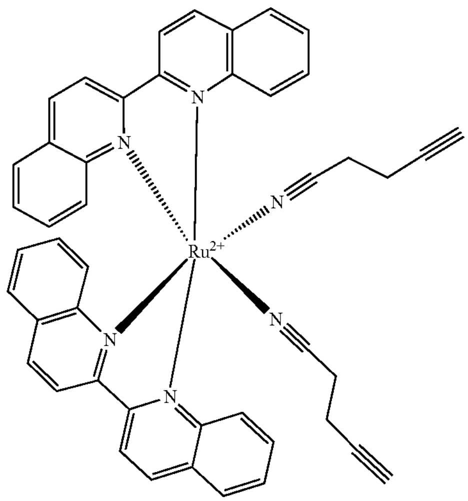 | [Ru(biquinoline)$_2$(4-pentynenitrile)$_2$]$^{2+}$ | Ru530 |
| 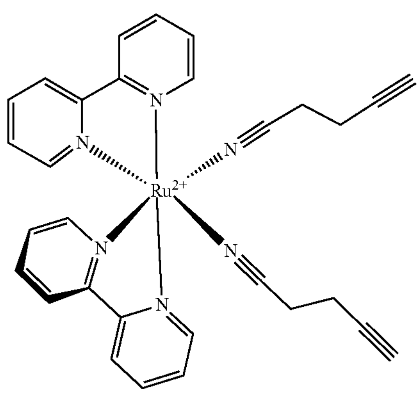 | [Ru(bipyridine)$_2$(4-aminobutyne)$_2$]$^{2+}$ | |
| 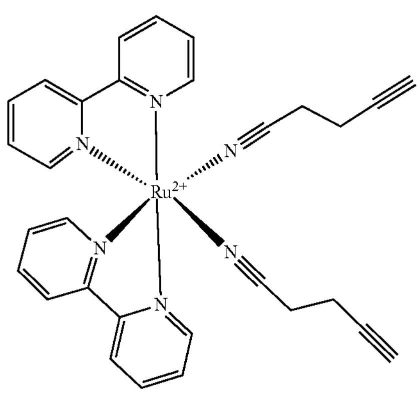 | [Ru(bipyridine)$_2$(4-pentynenitrile)$_2$]$^{2+}$ | Ru420 |

TABLE 1-continued

Compounds of the present invention

| Structure | Name | Compound Name |
|---|---|---|
| 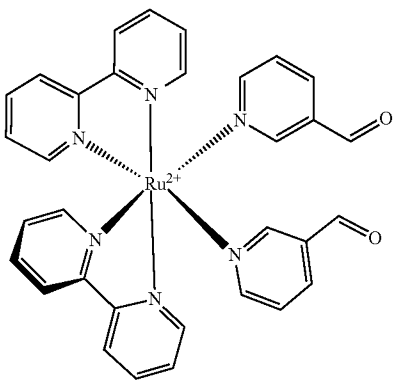 | [Ru(bipyridine)$_2$(nicotinaldehyde)$_2$]$^{2+}$ | |
| 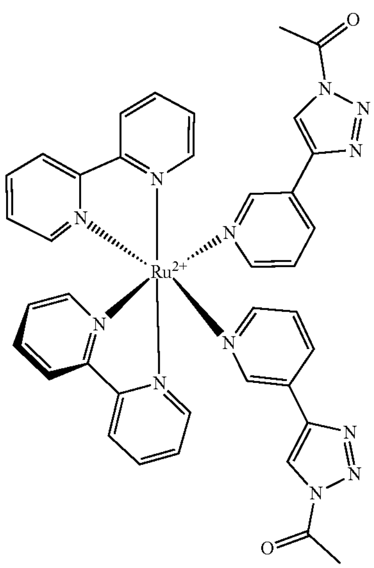 | [Ru(bipyridine)$_2$(1-(4-(pyridin-3-yl)-1H-1,2,3-triazol-1-yl)ethanone)$_2$]$^{2+}$ | |
| 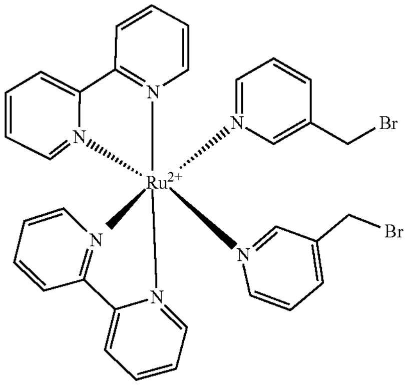 | [Ru(bipyridine)$_2$(3-(bromomethyl)pyridine)$_2$]$^{2+}$ | |

TABLE 1-continued

Compounds of the present invention

| Structure | Name | Compound Name |
|---|---|---|
| 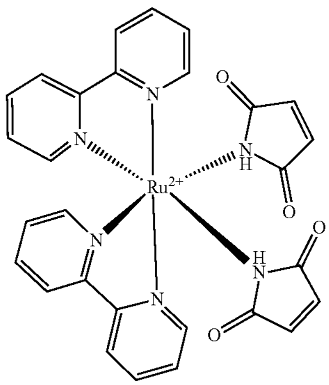 | [Ru(bipyridine)$_2$(maleimide)$_2$]$^{2+}$ |  |

The materials and methods employed in these experiments are now described.

Materials

Organic reagents and solvents were used as purchased from the following chemical sources:

Fisher: methanol, methylene chloride (HPLC grade), acetonitrile (HPLC grade), acetone.

Acros Organics: cis-dichloro-bis(2,2'-bipyridine)ruthenium(II) (98%), 3-ethynylpyridine (96%), silver trifluoromethansulfonate (99+%), ammonium hexafluorophosphate (99.5%), acetonitrile-d$^3$ (99.8 atom %), tetrabutylammonium chloride hydrate (98%), deuterium oxide (99.8 atom %)

Complementary DNA oligonucleotides, azido-DNA oligonucleotides, and molecular beacons were custom synthesized and HPLC purified by Integrated DNA technologies (Coralville, Iowa). Azido-MOs were custom synthesized by Gene Tools (Philomath, Oreg.). All gel reagents were purchased from Bio-Rad (Hercules, Calif.). TBTA ligand (Tris[(1-benzyl-1H-1,2,3-triazol-4-yl)methyl]amine) was purchased through Anaspec (Fremont, Calif.). Zebrafish embryos were obtained through the CDB Zebrafish Core Facility at the University of Pennsylvania Perelman School of Medicine.

Instrumentation

A Luxeon III Star® Royal Blue© LED was used for uncaging experiments post-click reactions, including in vivo work. It was purchased from Quadica Developments Inc. (Ontario, Canada) with a maximum output wavelength of 450 nm. Measured power at sample was 14 mW/cm$^2$.

A sapphire Galaxy Blue handheld laser was purchased from Beam of Light Technologies (Oregon, USA) and used to determine the quantum yield of RuBEP. Measured power at the sample was 53 mW/cm$^2$, with a maximum output wavelength of 450 nm.

UV-Visible spectroscopy was performed using an Agilent 8453 UV-Visible spectrometer (Agilent Technologies, Germany) in water unless otherwise specified. $^1$H NMR spectra were obtained on a Bruker DMX 500 spectrometer, and $^{13}$C NMR spectra were obtained using a Bruker AVIII cryo500 probe spectrometer at the University of Pennsylvania NMR facility and were recorded at room temperature. The $^1$H and $^{13}$C spectra were referenced to the central line of the solvent residual or to TMS at 0.00 ppm. $^1$H NMR and $^{13}$C NMR chemical shifts ($\delta$) are given in parts per million and reported to a precision off ±0.01 and ±0.1 ppm, respectively. Proton coupling constants (J) are given in Hz and reported to a precision of ±0.1 Hz.

High-resolution mass spectra (HRMS) were obtained using electrospray ionization (ESI) mass spectrometry on a Micromass Autospec at the Mass Spectrometry Facility in the Department of Chemistry at the University of Pennsylvania. Irradiated sample was analyzed via direct infusion nanospray with a Thermo ORBI trap XL mass spectrometer at 60 K resolution. Gels were imaged with a Typhoon FLA 7000 imaging system (GE Healthcare Life Sciences, Pittsburgh, Pa.).

All oligo purifications were performed with Agilent 1200 Analytical HPLC using a diode-array detector set to 260 nm. A 5-micron Zorbax semi-preparatory C18 column (9.4×215 mm) was used for all reverse-phase purifications.

Synthesis of [Ru(bpy)$_2$(3-ethynylpyridine)$_2$](Cl)$_2$

[Ru(bpy)$_2$(3-ethynylpyridine)$_2$](Cl)$_2$ was prepared as follows. Ru(bpy)$_2$Cl$_2$ (101.8 mg, 0.20 mmol) and AgSO$_3$CF$_3$ (105 mg, 0.41 mmol) were suspended in distilled methanol (10 mL). The solution was placed in the freezer overnight under nitrogen. The solution was then brought to rt, filtered to remove AgCl, and 3-ethynylpyridine (3EP, 201.7 mg, 0.40 mmol) was added. The reaction was heated to 75° C. for 5 h until no further changes were observed by UV-Vis spectroscopy. The methanol was removed under reduced pressure and product was redissolved in boiling water. Solid ammonium hexafluorophosphate was added to the chilled solution until a light orange precipitate was formed. This was vacuum filtered, washed twice with cold water and dried. The compound was further purified by 1.5×15 cm silica column (230-400 mesh) with 9:1 dichloromethane:acetonitrile as eluent and isolated in 71% yield (106.6 mg, 0.12 mmol). The water-soluble chloride salt was synthesized by addition of tetrabutylammonium chloride to a solution of [Ru(bpy)$_2$(3EP)$_2$](PF$_6$)$_2$ dissolved in acetone.

$^1$H NMR (500 MHz, CD$_3$CN): $\delta$ 3.74 (s, 1H, 3EP-H$_5$), 7.33 (dd, 1H, J=7.9, 3EP-H$_3$), 7.39 (ddd, 1H, J=6.7, bpy-H$_3$), 7.82 (ddd, 1H, J=6.4, bpy-H$_6$), 7.90 (d, 1H, J=5.4, bpy-H$_1$), 7.95 (dd, 1H, J=5.8, 3EP-H$_2$), 7.97 (dd, 1H, J=7.6, bpy-H$_2$), 8.19 (td, 1H, J=7.9, bpy-H$_7$), 8.31 (d, 1H, J=8.2, bpy-H$_4$), 8.32 (d, 1H, J=5.2, 3EP-H$_1$), 8.38 (s, 1H, 3EP-H$_4$), 8.40 (d, 1H, J=7.9, bpy-H$_5$), 8.95 (d, 1H, J=5.2, bpy-H$_8$).

$^{13}$C NMR (500 MHz, CD$_3$CN) δ 78.8, 84.5, 122.8, 124.9, 125.2, 126.9, 128.7, 129.0, 138.9, 139.2, 142.1, 153.5, 153.7, 154.5, 156.5, 158.6, 158.7.

Anal. Calc. for C$_{34}$H$_{12}$N$_6$RuP$_2$F$_{12}$: C, 65.90; H, 4.23; N, 13.56. Found: C, 66.2; H, 4.30; N, 13.7. MS(ES): m/2z 310.06, expected: m/2z 310.06

Circularization Procedure for DNA and Morpholino

Ru-oligo cyclization reactions were performed on a 10-12 nmol scale. Mono-azido DNA and bis-azido DNA were purchased from Integrated DNA Technologies, Coralville, Iowa. Bis-azido morpholinos were custom ordered from GeneTools, Philomath, Oreg. Bis-azido oligonucleotides were premixed with RuBEP at the indicated stoichiometric ratios. Cu(I)Br was dissolved in 3:1 DMSO/t-butanol to make a 0.1 M solution. TBTA ([(1-benzyl-1H-1,2,3-triazol-4-yl)methyl]amine) (Anaspec, Freemont, Calif.) was dissolved in 3:1 DMSO/t-butanol to make a 0.1 M solution. Cu(I)Br and TBTA were mixed in a 1:2 ratio and preincubated. The azide/alkyne solution volume was adjusted to 25 μL (for morpholino reactions) and 50 μl (for DNA reactions). 12% v/v of the Cu(I)Br/TBTA solution was added to the oligonucleotide solution. Solutions were sparged with N$_2$ and sealed tightly with parafilm. Reactions proceeded for 3 h (DNA) and 24-48 h (MO). Temperatures varying from RT to 55° C. were tested, and no significant correlation was found between temperature and product formation. Additionally, vortexing or not mixing did not seem to change product formation. After reaction completion, a NAP-5 desalting column (GE Healthcare) was used to remove unreacted RuBEP, Cu(I)Br, and TBTA. Circular product was stored in aqueous solution at −20° C.

| Reagent | nmol |
| --- | --- |
| Azido-oligo | 10-12 nmol |
| RuBEP | 10. |
| Cu(I)Br | 100. |
| TBTA | 200. |

Zebrafish Microinjection Experimental Details

Zebrafish embryos were obtained. All embryos obtained were TLFxTLF WT. Zebrafish embryo injection solutions were prepared to contain a final concentration of 0.1 M KCl and 0.25% phenol red dye. All injections were performed at the one-cell stage and injected into the cell compartment only. A Harvard Apparatus PLI-100 pico-injector was used to inject controlled volumes. Injection volume was calibrated to dispense 5 nL per embryo. Zebrafish embryos were incubated at 28° C. in E3 zebrafish medium. All embryos were incubated in the dark, except for irradiated embryos, which were exposed to 450-nm light (14 mW/cm$^2$, 5 min) at 1 hpf and returned to the dark incubator. Embryo micrographs were collected at 24 hpf with an Olympus FV1000 laser scanning confocal microscope using transmitted light imaging. A 10× air objective was used for single embryo imaging.

MALDI-MS Data

Figure 30:
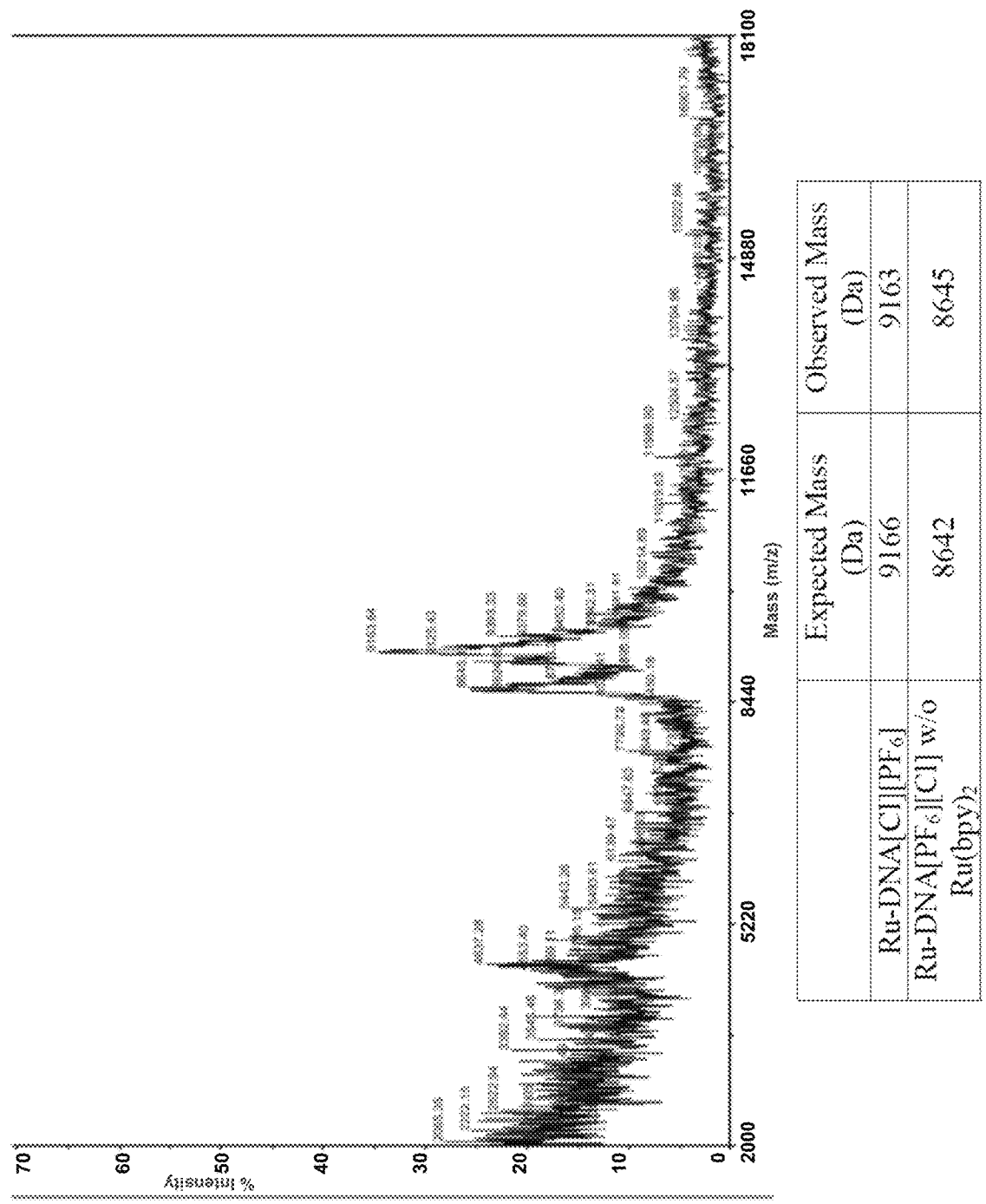
FIG. 30 is a spectrum of MALDI-TOF MS data for Ru-DNA.

Samples were analyzed using 3-hydroxypicolinic acid (3-HPA) matrix in linear positive ion mode on a Bruker Ultraflex III MALDI-TOF/TOF mass spectrometer (FIG. 30). Table 10 shows obtained MALDI-MS data.

TABLE 10

MALDI-MS data

|  | Expected mass (Da) | MALDI mass (Da) |
| --- | --- | --- |
| Ru-DNA* | 9166 | 9163 |
| Ru-cMO-chd | 9561 | 9567 |
| Ru-cMO-ntl | 9357 | 9385 |

*Ru-DNA[PF$_6$][Cl]: MALDI was performed by the Wistar Proteomics Facility at the University of Pennsylvania. All masses were attained in linear negative mode on an Applied Biosystems Voyager-DE ® PRO MALDI TOF Mass Spectrometer, using 3-hydroxypicolinic acid (3-HPA) matrix.

Molecular Beacon Hybridization Assay

Molecular beacons (Integrated DNA Technologies, Coralville, Iowa), complementary to the zebrafish chd and ntl MO sequence was designed, with fluorophore, 6-FAM on the 5' end and quencher, BHQ1 on the 3' end. Caging, indicative of circularization, was monitored by the opening of the molecular beacon in the presence of oligonucleotide.

A 3-fold excess of target sample (mismatched sequence, linear DNA or MO, Ru-MO/Ru-DNA, or its post-irradiation counterpart) was combined (mixed and gently vortexed) with the molecular beacon and allowed to hybridize over 20 min at 25° C. to best approximate physiological conditions. Irradiated samples were photolysed (3 min, 450 nm, 14 mW/cm$^2$) prior to addition of the beacon. The fluorescence intensity was then measured ($\lambda_{ex}$=454 nm, $\lambda_{em}$=513 nm). Significant decrease in fluorescence for the circularized Ru-MO/Ru-DNA sample relative to the linear MO indicated caging.

The beacon used for the Ru-MO had a higher melting point of activation than the beacon employed for Ru-DNA, which decreased the maximum fluorescence intensity observed. As such, the difference between the maximum and the minimum fluorescence intensity observed (for both the mismatched sequence and the caged Ru-MO) was less than that observed for the Ru-DNA molecular beacon reported in this work.

All solutions contained 1 pmol/μL of molecular beacon in a total volume of 70 μL.

Oligonucleotide Sequences

Table 11 shows the oligonucleotide sequences used in the experiments (5' to 3').

| | |
| --- | --- |
| DNA | GACTTGAGGCAGGCATATTTCCGAT (SEQ ID NO: 1) |
| reverse complement | ATCGGAAATATGCCTGCCTCAAGTC (SEQ ID NO: 2) |
| molecular beacon | 6FAM-CCACCCATCGGAAATATGCCTGCCTCAAGTCGGGTGG-BHQ1 (SEQ ID NO: 3) |
| chd-MO | ATCCACAGCAGCCCCTCCATCATCC (SEQ ID NO: 4) |

| | |
|---|---|
| chd reverse complement | GGATGATGGAGGGGCTGCTGTGGAT (SEQ ID NO: 5) |
| chd molecular beacon | 6FAM-CGGGCGGGATGATGGAGGGGCTGCTGTGGATCGCCCG-BHQ1 (SEQ ID NO: 6) |
| ntl MO* | AGCTTGAGATAAGTCCGACGATCCT (SEQ ID NO: 7) |
| ntl reverse complement | AGGATCGTCGGACTTATCTCAAGCT (SEQ ID NO: 8) |
| standard control MO | CCTCTTACCTCAGTTACAATTTATA (SEQ ID NO: 9) |

*notail MO sequence used was nt2-MO from Tallafuss et al. (Tallafuss et al., 2012, Development (Cambridge, England) 139:1691-1699)

Crystal Structure of [RuBEP](PF$_6$)$_2$

Compound $C_{34}H_{26}N_6P_2F_{12}Ru\cdot2\frac{1}{2}$ acetone, crystallized in the Triclinic space group PT with a=11.2159(7) Å, b=12.5550(8) Å, c=18.1382(12) Å, α=70.206(3)°, β=85.323(3)°, γ=67.450(2)°, V=2216.1(2)Å3, Z=2, and $d_{calc}$=1.581 g/cm3 (FIG. 33). X-ray intensity data were collected on a Bruker APEXII CCD area detector employing graphite-monochromated Mo-Kα radiation (λ=0.71073 Å) at a temperature of 100(1)K. Preliminary indexing was performed from a series of thirty-six 0.5° rotation frames with exposures of 10 seconds. A total of 2348 frames were collected with a crystal to detector distance of 37.6 mm, rotation widths of 0.5° and exposures of 20 seconds as demonstrated in Table 2.

TABLE 2

| scan type | 2Θ | ω | Φ | χ | frames |
|---|---|---|---|---|---|
| Φ | 19.50 | 327.79 | 15.97 | 36.30 | 739 |
| Φ | −20.50 | 342.55 | 321.55 | −73.06 | 739 |
| ω | −23.00 | 333.53 | 158.99 | −70.01 | 64 |
| ω | −15.50 | 340.80 | 341.11 | −63.64 | 99 |
| ω | −25.50 | 330.51 | 47.91 | −56.95 | 185 |
| ω | −25.50 | 239.19 | 209.98 | 28.88 | 204 |
| ω | −18.00 | 243.20 | 310.97 | 36.30 | 208 |
| ω | 27.00 | 277.79 | 5.00 | 57.63 | 221 |
| Φ | −10.50 | 318.39 | 249.35 | 52.47 | 254 |
| ω | 17.00 | 322.24 | 318.36 | 83.36 | 114 |
| Φ | 27.00 | 352.41 | 83.39 | 85.83 | 157 |
| Φ | −18.00 | 124.02 | 292.98 | −95.28 | 588 |

Rotation frames were integrated using SAINT (Bruker (2009) SAINT. Bruker AXS Inc., Madison, Wis., USA) producing a listing of unaveraged F2 and σ(F2) values which were then passed to the SHELXTL (Bruker (2009) SHELXTL. Bruker AXS Inc., Madison, Wis., USA) program package for further processing and structure solution. A total of 73021 reflections were measured over the ranges 1.86≤Θ≤27.54°, −14≤h≤14, −16≤k≤16, −23≤l≤23 yielding 10200 unique reflections ($R_{int}$=0.0189). The intensity data were corrected for Lorentz and polarization effects and for absorption using SADABS (Sheldrick, G. M. (2007) SADABS. University of Gottingen, Germany) (minimum and maximum transmission 0.6876, 0.7456).

The structure was solved by direct methods (SHELXS-97) (Sheldrick, 2008, Acta Cryst. A64,112-122). Refinement was by full-matrix least squares based on F2 using SHELXL-97 (Sheldrick, 2008, Acta Cryst. A64,112-122). All reflections were used during refinement. The weighting scheme used was w=1/[σ2($F_o^2$)+(0.0907P)$^2$+0.3133P] where P=($F_o^2$+2$F_c^2$)/3. Non-hydrogen atoms were refined anisotropically and hydrogen atoms were refined using a riding model. Refinement converged to R1=0.0266 and wR2=0.0630 for 9570 observed reflections for which F>4σ(F) and R1=0.0292 and wR2=0.0655 and GOF=1.051 for all 10200 unique, non-zero reflections and 643 variables using the following equation:

$$R1 = \Sigma ||F_o| - |F_c|| / \Sigma |F_o|$$

$$wR2 = [\Sigma w(F_o^2 - F_c^2)^2 / \Sigma w(F_o^2)^2]^{1/2}$$

$$GOF = [\Sigma w(F_o^2 - F_c^2)^2 / (n-p)]^{1/2}$$

where n=the number of reflections and p=the number of parameters refined.

The maximum Δ/σ in the final cycle of least squares was 0.002 and the two most prominent peaks in the final difference Fourier were +1.120 and −0.826 e/Å$^3$.

Table 3 lists cell information, data collection parameters, and refinement data. Final positional and equivalent isotropic thermal parameters are given in Tables 4 and 5. Anisotropic thermal parameters are in Table 6. Tables S5 and S6 list bond distances and bond angles. FIG. 3 is an ORTEP representation of the molecule with 50% probability thermal ellipsoids displayed.

TABLE 3

Summary of Structure Determination of [RuBEP](PF$_6$)$_2$

| | |
|---|---|
| Empirical formula | $C_{83}H_{82}F_{24}N_{12}O_5P_4Ru_2$ |
| Formula weight | 2109.63 |
| Temperature | 100(1) K |
| Wavelength | 0.71073 Å |
| Crystal system | Triclinic |
| Space group | P1 |
| Cell constants: | |
| a | 11.2159(7) Å |
| b | 12.5550(8) Å |
| c | 18.1382(12) Å |
| α | 70.206(3)° |
| β | 85.323(3)° |
| γ | 67.450(2)° |
| Volume | 2216.1(2) Å$^3$ |
| Z | 1 |
| Density (calculated) | 1.581 Mg/m$^3$ |
| Absorption coefficient | 0.522 mm$^{-1}$ |
| F(000) | 1068 |
| Crystal size | 0.42 × 0.26 × 0.10 mm$^3$ |
| Theta range for data collection | 1.86 to 27.54° |
| Index ranges | −14 ≤ h ≤ 14, −16 ≤ k ≤ 16, −23 ≤ l ≤ 23 |
| Reflections collected | 73021 |
| Independent reflections | 10200 [R(int) = 0.0189] |

TABLE 3-continued

Summary of Structure Determination of [RuBEP](PF$_6$)$_2$

| | |
|---|---|
| Completeness to theta = 27.54° | 99.6% |
| Absorption correction | Semi-empirical from equivalents |
| Max. and min. transmission | 0.7456 and 0.6876 |
| Refinement method | Full-matrix least-squares on F$^2$ |
| Data/restraints/parameters | 10200/122/643 |
| Goodness-of-fit on F$^2$ | 1.051 |
| Final R indices [I > 2sigma(I)] | R1 = 0.0266, wR2 = 0.0630 |
| R indices (all data) | R1 = 0.0292, wR2 = 0.0655 |
| Largest diff. peak and hole | 1.120 and −0.826 e · Å$^{-3}$ |

TABLE 4

Refined Positional Parameters for [RuBEP](PF$_6$)$_2$

| Atom | x | y | z | U$_{eq}$, Å$^2$ |
|---|---|---|---|---|
| Ru1 | 0.506258(11) | 0.163868(11) | 0.264396(7) | 0.01291(4) |
| N1 | 0.65818(12) | 0.13185(12) | 0.19098(8) | 0.0153(2) |
| N12 | 0.45450(12) | 0.07306(12) | 0.20479(8) | 0.0149(2) |
| N13 | 0.57466(12) | −0.00632(12) | 0.34959(8) | 0.0155(2) |
| N24 | 0.35555(12) | 0.17812(12) | 0.33876(8) | 0.0154(2) |
| N25 | 0.57819(13) | 0.24338(12) | 0.32652(8) | 0.0155(2) |
| N33 | 0.41533(12) | 0.33223(12) | 0.17585(8) | 0.0151(2) |
| C2 | 0.75831(15) | 0.16753(15) | 0.18526(10) | 0.0188(3) |
| C3 | 0.85450(16) | 0.14474(16) | 0.13324(10) | 0.0219(3) |
| C4 | 0.84615(17) | 0.08520(16) | 0.08327(10) | 0.0235(3) |
| C5 | 0.74281(16) | 0.04878(16) | 0.08769(10) | 0.0218(3) |
| C6 | 0.65119(15) | 0.07173(14) | 0.14269(9) | 0.0169(3) |
| C7 | 0.54123(15) | 0.03182(14) | 0.15400(9) | 0.0173(3) |
| C8 | 0.52811(17) | −0.04635(17) | 0.11907(11) | 0.0247(4) |
| C9 | 0.42495(18) | −0.08374(17) | 0.13656(12) | 0.0272(4) |
| C10 | 0.33660(17) | −0.04140(16) | 0.18777(10) | 0.0226(3) |
| C11 | 0.35404(15) | 0.03707(15) | 0.22011(9) | 0.0180(3) |
| C14 | 0.68458(15) | −0.09937(15) | 0.34717(10) | 0.0195(3) |
| C15 | 0.71162(17) | −0.21890(16) | 0.39519(11) | 0.0247(4) |
| C16 | 0.62293(18) | −0.24480(16) | 0.44906(11) | 0.0261(4) |
| C17 | 0.51085(17) | −0.14999(16) | 0.45341(10) | 0.0222(3) |
| C18 | 0.48813(15) | −0.03161(14) | 0.40305(9) | 0.0165(3) |
| C19 | 0.36860(15) | 0.07434(14) | 0.40007(9) | 0.0161(3) |
| C20 | 0.27411(16) | 0.07009(16) | 0.45418(10) | 0.0204(3) |
| C21 | 0.16281(17) | 0.17312(17) | 0.44612(10) | 0.0235(3) |
| C22 | 0.15004(17) | 0.27882(16) | 0.38419(11) | 0.0239(3) |
| C23 | 0.24783(16) | 0.27815(15) | 0.33221(10) | 0.0198(3) |
| C26 | 0.50882(15) | 0.35333(14) | 0.33424(9) | 0.0173(3) |
| C27 | 0.55503(16) | 0.40441(15) | 0.37742(10) | 0.0200(3) |
| C28 | 0.67825(17) | 0.33911(15) | 0.41461(10) | 0.0211(3) |
| C29 | 0.75013(16) | 0.22637(15) | 0.40647(10) | 0.0198(3) |
| C30 | 0.69787(15) | 0.18182(14) | 0.36276(9) | 0.0172(3) |
| C31 | 0.47574(18) | 0.52329(17) | 0.38143(11) | 0.0262(4) |
| C32 | 0.4114(2) | 0.62209(19) | 0.38320(13) | 0.0366(5) |
| C34 | 0.47048(15) | 0.41520(14) | 0.14776(9) | 0.0164(3) |
| C35 | 0.41314(15) | 0.52533(14) | 0.08664(9) | 0.0173(3) |
| C36 | 0.29400(16) | 0.55052(15) | 0.05305(9) | 0.0191(3) |
| C37 | 0.23679(16) | 0.46539(15) | 0.08154(10) | 0.0191(3) |
| C38 | 0.29993(15) | 0.35806(15) | 0.14190(9) | 0.0174(3) |
| C39 | 0.47884(16) | 0.60893(15) | 0.05965(10) | 0.0201(3) |
| C40 | 0.53479(18) | 0.67633(17) | 0.03667(11) | 0.0259(4) |
| P1 | 0.91753(4) | 0.07849(4) | 0.63543(3) | 0.01945(9) |
| F1 | 0.77189(10) | 0.10137(11) | 0.61329(8) | 0.0342(3) |
| F2 | 1.06165(11) | 0.05864(13) | 0.65717(9) | 0.0424(3) |
| F3 | 0.92791(14) | −0.04413(12) | 0.70349(9) | 0.0504(4) |
| F4 | 0.97134(12) | 0.00549(13) | 0.57550(9) | 0.0439(3) |
| F5 | 0.90455(13) | 0.20274(12) | 0.56596(8) | 0.0429(3) |
| F6 | 0.86228(11) | 0.15488(12) | 0.69372(7) | 0.0368(3) |
| P2 | 0.86742(4) | 0.76441(4) | −0.00468(3) | 0.02104(9) |
| F7 | 0.83036(18) | 0.78269(12) | 0.07769(9) | 0.0564(4) |
| F8 | 0.89749(19) | 0.75132(17) | −0.08864(9) | 0.0644(5) |
| F9 | 0.71659(13) | 0.81513(15) | −0.02793(10) | 0.0695(6) |
| F10 | 0.86397(11) | 0.90155(10) | −0.04003(7) | 0.0306(2) |
| F11 | 1.01548(12) | 0.71759(12) | 0.01791(11) | 0.0554(4) |
| F12 | 0.86992(12) | 0.62856(11) | 0.03176(8) | 0.0373(3) |
| C41 | 0.8714(2) | 0.33261(18) | 0.77964(12) | 0.0307(4) |
| C42 | 1.0085(2) | 0.2875(3) | 0.75661(19) | 0.0539(7) |
| C43 | 0.8319(3) | 0.2412(2) | 0.84166(13) | 0.0412(5) |
| O1 | 0.79828(19) | 0.43755(14) | 0.75071(11) | 0.0501(4) |
| C44 | 0.7925(4) | 0.4704(4) | 0.2172(3) | 0.0285(8) |
| C45 | 0.9341(4) | 0.4331(4) | 0.2064(3) | 0.0467(10) |
| C46 | 0.7225(4) | 0.5914(5) | 0.2295(4) | 0.0436(12) |
| O2 | 0.7350(3) | 0.4074(3) | 0.21545(17) | 0.0437(6) |
| C47 | 0.7960(5) | 0.5225(4) | 0.2705(3) | 0.0266(9) |
| C48 | 0.6794(7) | 0.6370(7) | 0.2342(5) | 0.0403(16) |
| C49 | 0.8510(10) | 0.4355(8) | 0.2255(5) | 0.052(2) |
| O3 | 0.8449(3) | 0.5035(3) | 0.33352(18) | 0.0263(7) |
| C50 | 0.9372(4) | 0.4879(4) | 0.4842(3) | 0.0275(9) |
| C51 | 0.8817(5) | 0.4529(4) | 0.5634(3) | 0.0425(11) |
| C52 | 1.0506(5) | 0.5301(5) | 0.4789(3) | 0.0392(11) |
| O4 | 0.8932(3) | 0.4866(3) | 0.42707(17) | 0.0347(6) |

U$_{eq}$ = ⅓[U$_{11}$(aa*)$^2$ + U$_{22}$(bb*)$^2$ + U$_{33}$(cc*)$^2$ + 2U$_{12}$aa*bb*cos γ + 2U$_{13}$aa*cc*cos β + 2U$_{23}$bb*cc*cosα]

TABLE 5

Positional Parameters for Hydrogens in [RuBEP](PF$_6$)$_2$

| Atom | x | y | z | U$_{iso}$, Å$^2$ |
|---|---|---|---|---|
| H2 | 0.7632 | 0.2095 | 0.2178 | 0.025 |
| H3 | 0.9235 | 0.1690 | 0.1319 | 0.029 |
| H4 | 0.9089 | 0.0698 | 0.0473 | 0.031 |
| H5 | 0.7349 | 0.0095 | 0.0542 | 0.029 |
| H8 | 0.5881 | −0.0732 | 0.0843 | 0.033 |
| H9 | 0.4153 | −0.1367 | 0.1141 | 0.036 |
| H10 | 0.2665 | −0.0653 | 0.2003 | 0.030 |
| H11 | 0.2936 | 0.0662 | 0.2540 | 0.024 |
| H14 | 0.7450 | −0.0826 | 0.3117 | 0.026 |
| H15 | 0.7882 | −0.2811 | 0.3914 | 0.033 |
| H16 | 0.6387 | −0.3246 | 0.4816 | 0.035 |
| H17 | 0.4508 | −0.1651 | 0.4898 | 0.030 |
| H20 | 0.2856 | −0.0018 | 0.4957 | 0.027 |
| H21 | 0.0982 | 0.1713 | 0.4815 | 0.031 |
| H22 | 0.0766 | 0.3496 | 0.3775 | 0.032 |
| H23 | 0.2386 | 0.3499 | 0.2911 | 0.026 |
| H26 | 0.4265 | 0.3972 | 0.3097 | 0.023 |
| H28 | 0.7113 | 0.3704 | 0.4441 | 0.028 |
| H29 | 0.8329 | 0.1810 | 0.4302 | 0.026 |
| H30 | 0.7473 | 0.1059 | 0.3580 | 0.023 |
| H32 | 0.3608 | 0.6998 | 0.3846 | 0.049 |
| H34 | 0.5502 | 0.3985 | 0.1700 | 0.022 |
| H36 | 0.2535 | 0.6231 | 0.0122 | 0.025 |
| H37 | 0.1569 | 0.4803 | 0.0603 | 0.025 |
| H38 | 0.2613 | 0.3009 | 0.1600 | 0.023 |
| H40 | 0.5786 | 0.7291 | 0.0187 | 0.034 |
| H42a | 1.0273 | 0.3552 | 0.7214 | 0.081 |
| H42b | 1.0201 | 0.2290 | 0.7310 | 0.081 |
| H42c | 1.0658 | 0.2495 | 0.8027 | 0.081 |
| H43a | 0.8614 | 0.2331 | 0.8922 | 0.062 |
| H43b | 0.8695 | 0.1636 | 0.8335 | 0.062 |
| H43c | 0.7394 | 0.2679 | 0.8392 | 0.062 |
| H45a | 0.9675 | 0.3548 | 0.1992 | 0.070 |
| H45b | 0.9768 | 0.4278 | 0.2521 | 0.070 |
| H45c | 0.9493 | 0.4926 | 0.1612 | 0.070 |
| H46a | 0.6326 | 0.6048 | 0.2359 | 0.065 |
| H46b | 0.7310 | 0.6558 | 0.1848 | 0.065 |
| H46c | 0.7591 | 0.5910 | 0.2757 | 0.065 |
| H48a | 0.6533 | 0.6840 | 0.2689 | 0.060 |
| H48b | 0.6099 | 0.6152 | 0.2253 | 0.060 |
| H48c | 0.7006 | 0.6847 | 0.1851 | 0.060 |
| H49a | 0.9247 | 0.3670 | 0.2547 | 0.077 |
| H49b | 0.8769 | 0.4766 | 0.1757 | 0.077 |
| H49c | 0.7866 | 0.4072 | 0.2171 | 0.077 |
| H51a | 0.8093 | 0.4324 | 0.5583 | 0.064 |
| H51b | 0.8537 | 0.5205 | 0.5827 | 0.064 |
| H51c | 0.9467 | 0.3836 | 0.5994 | 0.064 |
| H52a | 1.0786 | 0.5469 | 0.4262 | 0.059 |
| H52b | 1.1208 | 0.4668 | 0.5143 | 0.059 |
| H52c | 1.0229 | 0.6029 | 0.4928 | 0.059 |

TABLE 6

Refined Thermal Parameters (U's) for [RuBEP](PF$_6$)$_2$

| Atom | $U_{11}$ | $U_{22}$ | $U_{33}$ | $U_{23}$ | $U_{13}$ | $U_{12}$ |
|---|---|---|---|---|---|---|
| Ru1 | 0.01149(6) | 0.01408(6) | 0.01414(6) | −0.00525(4) | 0.00267(4) | −0.00578(5) |
| N1 | 0.0133(6) | 0.0157(6) | 0.0157(6) | −0.0045(5) | 0.0025(5) | −0.0053(5) |
| N12 | 0.0145(6) | 0.0150(6) | 0.0148(6) | −0.0042(5) | 0.0016(5) | −0.0061(5) |
| N13 | 0.0141(6) | 0.0169(6) | 0.0169(6) | −0.0066(5) | 0.0008(5) | −0.0066(5) |
| N24 | 0.0153(6) | 0.0181(6) | 0.0154(6) | −0.0072(5) | 0.0027(5) | −0.0081(5) |
| N25 | 0.0160(6) | 0.0164(6) | 0.0146(6) | −0.0047(5) | 0.0033(5) | −0.0075(5) |
| N33 | 0.0147(6) | 0.0161(6) | 0.0154(6) | −0.0066(5) | 0.0031(5) | −0.0061(5) |
| C2 | 0.0170(7) | 0.0220(8) | 0.0192(7) | −0.0070(6) | 0.0028(6) | −0.0095(6) |
| C3 | 0.0163(7) | 0.0256(8) | 0.0230(8) | −0.0052(7) | 0.0047(6) | −0.0104(6) |
| C4 | 0.0195(8) | 0.0262(8) | 0.0232(8) | −0.0088(7) | 0.0089(6) | −0.0080(7) |
| C5 | 0.0221(8) | 0.0231(8) | 0.0214(8) | −0.0104(7) | 0.0061(6) | −0.0081(7) |
| C6 | 0.0153(7) | 0.0157(7) | 0.0182(7) | −0.0049(6) | 0.0018(6) | −0.0052(6) |
| C7 | 0.0157(7) | 0.0174(7) | 0.0182(7) | −0.0063(6) | 0.0017(6) | −0.0056(6) |
| C8 | 0.0229(8) | 0.0274(9) | 0.0298(9) | −0.0173(7) | 0.0072(7) | −0.0103(7) |
| C9 | 0.0282(9) | 0.0294(9) | 0.0348(10) | −0.0196(8) | 0.0052(7) | −0.0154(8) |
| C10 | 0.0225(8) | 0.0247(8) | 0.0258(8) | −0.0093(7) | 0.0029(7) | −0.0140(7) |
| C11 | 0.0166(7) | 0.0201(7) | 0.0180(7) | −0.0060(6) | 0.0025(6) | −0.0083(6) |
| C14 | 0.0156(7) | 0.0212(8) | 0.0218(8) | −0.0071(6) | 0.0015(6) | −0.0071(6) |
| C15 | 0.0196(8) | 0.0190(8) | 0.0309(9) | −0.0071(7) | 0.0000(7) | −0.0032(6) |
| C16 | 0.0274(9) | 0.0174(8) | 0.0291(9) | −0.0017(7) | −0.0009(7) | −0.0085(7) |
| C17 | 0.0221(8) | 0.0221(8) | 0.0225(8) | −0.0044(7) | 0.0028(7) | −0.0113(7) |
| C18 | 0.0160(7) | 0.0194(7) | 0.0167(7) | −0.0068(6) | 0.0013(6) | −0.0086(6) |
| C19 | 0.0172(7) | 0.0184(7) | 0.0159(7) | −0.0074(6) | 0.0019(6) | −0.0090(6) |
| C20 | 0.0238(8) | 0.0232(8) | 0.0183(8) | −0.0077(6) | 0.0056(6) | −0.0133(7) |
| C21 | 0.0216(8) | 0.0295(9) | 0.0246(8) | −0.0140(7) | 0.0104(7) | −0.0126(7) |
| C22 | 0.0197(8) | 0.0251(8) | 0.0266(9) | −0.0131(7) | 0.0069(7) | −0.0056(7) |
| C23 | 0.0189(8) | 0.0198(8) | 0.0201(8) | −0.0076(6) | 0.0034(6) | −0.0064(6) |
| C26 | 0.0164(7) | 0.0174(7) | 0.0169(7) | −0.0052(6) | 0.0029(6) | −0.0061(6) |
| C27 | 0.0222(8) | 0.0189(8) | 0.0203(8) | −0.0082(6) | 0.0042(6) | −0.0083(6) |
| C28 | 0.0236(8) | 0.0224(8) | 0.0218(8) | −0.0097(6) | 0.0009(6) | −0.0112(7) |
| C29 | 0.0173(7) | 0.0211(8) | 0.0202(8) | −0.0051(6) | −0.0007(6) | −0.0076(6) |
| C30 | 0.0162(7) | 0.0167(7) | 0.0178(7) | −0.0052(6) | 0.0025(6) | −0.0062(6) |
| C31 | 0.0268(9) | 0.0264(9) | 0.0281(9) | −0.0135(7) | 0.0001(7) | −0.0087(7) |
| C32 | 0.0350(11) | 0.0292(10) | 0.0446(12) | −0.0212(9) | −0.0036(9) | −0.0021(8) |
| C34 | 0.0151(7) | 0.0194(7) | 0.0174(7) | −0.0088(6) | 0.0038(6) | −0.0075(6) |
| C35 | 0.0196(7) | 0.0177(7) | 0.0166(7) | −0.0082(6) | 0.0067(6) | −0.0080(6) |
| C36 | 0.0200(8) | 0.0171(7) | 0.0172(7) | −0.0053(6) | 0.0021(6) | −0.0042(6) |
| C37 | 0.0161(7) | 0.0211(8) | 0.0207(8) | −0.0088(6) | 0.0009(6) | −0.0060(6) |
| C38 | 0.0153(7) | 0.0188(7) | 0.0210(8) | −0.0089(6) | 0.0033(6) | −0.0082(6) |
| C39 | 0.0209(8) | 0.0196(8) | 0.0193(8) | −0.0077(6) | 0.0049(6) | −0.0068(6) |
| C40 | 0.0298(9) | 0.0251(9) | 0.0268(9) | −0.0100(7) | 0.0096(7) | −0.0149(7) |
| P1 | 0.01575(19) | 0.0244(2) | 0.0210(2) | −0.01088(17) | 0.00422(15) | −0.00833(16) |
| F1 | 0.0199(5) | 0.0419(7) | 0.0526(7) | −0.0303(6) | 0.0009(5) | −0.0113(5) |
| F2 | 0.0166(5) | 0.0530(8) | 0.0643(9) | −0.0304(6) | −0.0008(5) | −0.0103(5) |
| F3 | 0.0471(8) | 0.0362(7) | 0.0502(8) | −0.0053(6) | 0.0052(6) | −0.0149(6) |
| F4 | 0.0363(7) | 0.0536(8) | 0.0534(8) | −0.0411(7) | 0.0134(6) | −0.0111(6) |
| F5 | 0.0426(7) | 0.0355(7) | 0.0405(7) | −0.0020(5) | 0.0113(6) | −0.0151(6) |
| F6 | 0.0305(6) | 0.0582(8) | 0.0378(6) | −0.0358(6) | 0.0084(5) | −0.0177(6) |
| P2 | 0.01733(19) | 0.0287(2) | 0.0218(2) | −0.01123(17) | 0.00414(16) | −0.01182(17) |
| F7 | 0.1081(13) | 0.0372(7) | 0.0286(7) | −0.0170(6) | 0.0303(7) | −0.0324(8) |
| F8 | 0.1137(14) | 0.0909(12) | 0.0411(8) | −0.0449(8) | 0.0397(9) | −0.0807(12) |
| F9 | 0.0283(7) | 0.0710(10) | 0.0773(11) | −0.0349(9) | −0.0177(7) | −0.0329(7) |
| F10 | 0.0297(6) | 0.0302(6) | 0.0310(6) | −0.0061(5) | 0.0064(5) | −0.0148(5) |
| F11 | 0.0200(6) | 0.0354(7) | 0.0984(12) | −0.0064(7) | −0.0155(7) | −0.0078(5) |
| F12 | 0.0438(7) | 0.0322(6) | 0.0451(7) | −0.0163(5) | 0.0065(6) | −0.0221(5) |
| C41 | 0.0405(11) | 0.0273(9) | 0.0309(10) | −0.0136(8) | −0.0054(8) | −0.0148(8) |
| C42 | 0.0437(13) | 0.0595(16) | 0.0807(19) | −0.0376(15) | 0.0061(13) | −0.0310(12) |
| C43 | 0.0648(15) | 0.0345(11) | 0.0319(11) | −0.0191(9) | 0.0104(10) | −0.0216(11) |
| O1 | 0.0649(12) | 0.0273(8) | 0.0487(10) | −0.0093(7) | −0.0069(8) | −0.0086(8) |
| C44 | 0.030(2) | 0.035(2) | 0.0234(18) | −0.0038(16) | 0.0006(17) | −0.0205(18) |
| C45 | 0.033(2) | 0.056(3) | 0.047(2) | −0.0104(19) | −0.0049(18) | −0.0172(19) |
| C46 | 0.052(3) | 0.039(3) | 0.051(3) | −0.018(3) | 0.016(3) | −0.029(3) |
| O2 | 0.0426(15) | 0.0430(15) | 0.0558(17) | −0.0174(13) | 0.0019(12) | −0.0259(12) |
| C47 | 0.030(2) | 0.024(2) | 0.025(2) | −0.0034(18) | 0.0004(19) | −0.019(2) |
| C48 | 0.038(4) | 0.042(4) | 0.030(3) | −0.003(3) | −0.011(3) | −0.013(3) |
| C49 | 0.062(6) | 0.052(5) | 0.042(4) | −0.021(4) | −0.008(5) | −0.018(4) |
| O3 | 0.0254(16) | 0.0274(16) | 0.0234(15) | −0.0020(13) | −0.0050(12) | −0.0114(13) |
| C50 | 0.0300(16) | 0.0191(14) | 0.0274(16) | −0.0095(14) | 0.0036(14) | −0.0020(11) |
| C51 | 0.065(3) | 0.041(2) | 0.028(2) | −0.0137(18) | 0.014(2) | −0.028(2) |
| C52 | 0.046(3) | 0.032(2) | 0.040(3) | −0.010(2) | −0.010(3) | −0.013(2) |
| O4 | 0.0321(15) | 0.0307(14) | 0.0386(16) | −0.0121(12) | 0.0000(12) | −0.0082(12) |

The form of the anisotropic displacement parameter is:
$\exp[-2\pi^2(a^{*2}U_{11}h^2 + b^{*2}U_{22}k^2 + c^{*2}U_{33}l^2 + 2b^*c^*U_{23}kl + 2a^*c^*U_{13}hl + 2a^*b^*U_{12}hk)]$

TABLE 7

Bond Distances in [RuBEP](PF$_6$)$_2$, Å

| | | | | | |
|---|---|---|---|---|---|
| Ru1—N13 | 2.0595(13) | Ru1—N12 | 2.0617(13) | Ru1—N24 | 2.0660(13) |
| Ru1—N1 | 2.0750(13) | Ru1—N33 | 2.0981(13) | Ru1—N25 | 2.1083(13) |
| N1—C2 | 1.345(2) | N1—C6 | 1.359(2) | N12—C11 | 1.344(2) |
| N12—C7 | 1.362(2) | N13—C14 | 1.345(2) | N13—C18 | 1.363(2) |
| N24—C23 | 1.345(2) | N24—C19 | 1.362(2) | N25—C26 | 1.349(2) |
| N25—C30 | 1.355(2) | N33—C34 | 1.346(2) | N33—C38 | 1.354(2) |
| C2—C3 | 1.384(2) | C3—C4 | 1.384(3) | C4—C5 | 1.388(2) |
| C5—C6 | 1.391(2) | C6—C7 | 1.476(2) | C7—C8 | 1.390(2) |
| C8—C9 | 1.384(2) | C9—C10 | 1.381(3) | C10—C11 | 1.382(2) |
| C14—C15 | 1.383(2) | C15—C16 | 1.387(3) | C16—C17 | 1.380(2) |
| C17—C18 | 1.392(2) | C18—C19 | 1.471(2) | C19—C20 | 1.388(2) |
| C20—C21 | 1.384(2) | C21—C22 | 1.384(3) | C22—C23 | 1.386(2) |
| C26—C27 | 1.398(2) | C27—C28 | 1.395(2) | C27—C31 | 1.438(2) |
| C28—C29 | 1.386(2) | C29—C30 | 1.383(2) | C31—C32 | 1.182(3) |
| C34—C35 | 1.397(2) | C35—C36 | 1.391(2) | C35—C39 | 1.439(2) |
| C36—C37 | 1.385(2) | C37—C38 | 1.383(2) | C39—C40 | 1.187(3) |
| P1—F3 | 1.5831(13) | P1—F4 | 1.5904(12) | P1—F6 | 1.5956(11) |
| P1—F2 | 1.5998(12) | P1—F5 | 1.6021(13) | P1—F1 | 1.6064(11) |
| P2—F11 | 1.5717(13) | P2—F8 | 1.5821(14) | P2—F7 | 1.5907(13) |
| P2—F12 | 1.5967(12) | P2—F9 | 1.5980(13) | P2—F10 | 1.6070(12) |
| C41—O1 | 1.207(3) | C41—C43 | 1.488(3) | C41—C42 | 1.498(3) |
| C44—O2 | 1.205(4) | C44—C45 | 1.490(5) | C44—C46 | 1.504(6) |
| C47—O3 | 1.217(5) | C47—C49 | 1.499(7) | C47—C48 | 1.506(6) |
| C50—O4 | 1.192(5) | C50—C51 | 1.509(5) | C50—C52 | 1.538(6) |

TABLE 8

Bond Angles in [RuBEP](PF$_6$)$_2$,

| | | | | | |
|---|---|---|---|---|---|
| N13—Ru1—N12 | 83.17(5) | N13—Ru1—N24 | 78.73(5) | N12—Ru1—N24 | 96.51(5) |
| N13—Ru1—N1 | 97.01(5) | N12—Ru1—N1 | 78.84(5) | N24—Ru1—N1 | 174.11(5) |
| N13—Ru1—N33 | 172.47(5) | N12—Ru1—N33 | 91.25(5) | N24—Ru1—N33 | 96.99(5) |
| N1—Ru1—N33 | 86.80(5) | N13—Ru1—N25 | 93.45(5) | N12—Ru1—N25 | 174.24(5) |
| N24—Ru1—N25 | 87.36(5) | N1—Ru1—N25 | 97.01(5) | N33—Ru1—N25 | 92.52(5) |
| C2—N1—C6 | 118.06(13) | C2—N1—Ru1 | 126.69(11) | C6—N1—Ru1 | 115.21(10) |
| C11—N12—C7 | 118.18(14) | C11—N12—Ru1 | 125.44(11) | C7—N12—Ru1 | 115.65(10) |
| C14—N13—C18 | 118.04(14) | C14—N13—Ru1 | 125.13(11) | C18—N13—Ru1 | 115.42(10) |
| C23—N24—C19 | 117.88(13) | C23—N24—Ru1 | 126.67(11) | C19—N24—Ru1 | 115.45(10) |
| C26—N25—C30 | 117.15(14) | C26—N25—Ru1 | 123.00(11) | C30—N25—Ru1 | 119.83(10) |
| C34—N33—C38 | 117.45(14) | C34—N33—Ru1 | 122.42(11) | C38—N33—Ru1 | 120.04(10) |
| N1—C2—C3 | 123.04(15) | C2—C3—C4 | 118.81(15) | C3—C4—C5 | 119.01(15) |
| C4—C5—C6 | 119.28(16) | N1—C6—C5 | 121.77(15) | N1—C6—C7 | 115.09(14) |
| C5—C6—C7 | 123.14(15) | N12—C7—C8 | 121.53(15) | N12—C7—C6 | 114.77(14) |
| C8—C7—C6 | 123.64(15) | C9—C8—C7 | 119.35(16) | C10—C9—C8 | 119.12(16) |
| C9—C10—C11 | 118.91(16) | N12—C11—C10 | 122.89(15) | N13—C14—C15 | 122.82(15) |
| C14—C15—C16 | 119.12(16) | C17—C16—C15 | 118.79(16) | C16—C17—C18 | 119.60(16) |
| N13—C18—C17 | 121.61(16) | N13—C18—C19 | 114.62(14) | C17—C18—C19 | 123.71(14) |
| N24—C19—C20 | 121.75(15) | N24—C19—C18 | 114.87(13) | C20—C19—C18 | 123.38(15) |
| C21—C20—C19 | 119.82(16) | C22—C21—C20 | 118.42(15) | C21—C22—C23 | 119.33(16) |
| N24—C23—C22 | 122.79(16) | N25—C26—C27 | 123.01(15) | C28—C27—C26 | 118.87(15) |
| C28—C27—C31 | 121.66(16) | C26—C27—C31 | 119.46(15) | C29—C28—C27 | 118.30(15) |
| C30—C29—C28 | 119.51(15) | N25—C30—C29 | 123.16(15) | C32—C31—C27 | 178.6(2) |
| N33—C34—C35 | 122.86(15) | C36—C35—C34 | 118.75(15) | C36—C35—C39 | 121.81(15) |
| C34—C35—C39 | 119.44(15) | C37—C36—C35 | 118.71(15) | C38—C37—C36 | 119.18(15) |
| N33—C38—C37 | 123.05(15) | C40—C39—C35 | 178.65(18) | F3—P1—F4 | 90.54(8) |
| F3—P1—F6 | 90.85(8) | F4—P1—F6 | 178.55(8) | F3—P1—F2 | 91.13(8) |
| F4—P1—F2 | 90.12(7) | F6—P1—F2 | 90.26(7) | F3—P1—F5 | 178.94(8) |
| F4—P1—F5 | 89.28(8) | F6—P1—F5 | 89.32(7) | F2—P1—F5 | 89.91(8) |
| F3—P1—F1 | 89.77(8) | F4—P1—F1 | 90.64(7) | F6—P1—F1 | 88.97(6) |
| F2—P1—F1 | 178.82(7) | F5—P1—F1 | 89.19(7) | F11—P2—F8 | 91.44(10) |
| F11—P2—F7 | 91.11(10) | F8—P2—F7 | 177.15(11) | F11—P2—F12 | 91.15(7) |
| F8—P2—F12 | 91.85(8) | F7—P2—F12 | 89.35(7) | F11—P2—F9 | 178.68(9) |
| F8—P2—F9 | 88.88(11) | F7—P2—F9 | 88.54(10) | F12—P2—F9 | 90.12(8) |
| F11—P2—F10 | 88.99(7) | F8—P2—F10 | 89.09(7) | F7—P2—F10 | 89.69(7) |
| F12—P2—F10 | 179.04(7) | F9—P2—F10 | 89.74(7) | O1—C41—C43 | 122.0(2) |
| O1—C41—C42 | 121.9(2) | C43—C41—C42 | 116.0(2) | O2—C44—C45 | 121.9(4) |
| O2—C44—C46 | 120.7(4) | C45—C44—C46 | 117.4(4) | O3—C47—C49 | 121.7(5) |
| O3—C47—C48 | 120.6(5) | C49—C47—C48 | 117.7(5) | O4—C50—C51 | 121.7(4) |
| O4—C50—C52 | 120.6(5) | C51—C50—C52 | 117.7(5) | | |

The results of the experiments are now described.

Described herein is the synthesis, characterization, and application of the first Ru-photolinker, [Ru(bipyridine)$_2$(3-ethynylpyridine)$_2$]Cl$_2$ (RuBEP) (FIG. 1). The bis-alkyne functionality enabled circularization of an oligonucleotide containing azides at both 5' and 3' termini via [3+2] azide-alkyne copper(I)-mediated cycloaddition reactions (Tomoe et al., 2002, J. Org. Chem. 67:3057-3064; Rostovtsev et al., 2002, Angew. Chem., Int. Ed. Engl. 41:2596-2599). In this way, the octahedral $Ru^{2+}$ center remained coordinatively saturated, and side-reactions between $Ru^{2+}$ and the nucleobases were avoided. Photolysis at 450 nm restored the linear, biologically active oligo (FIG. 1).

Figure 2:
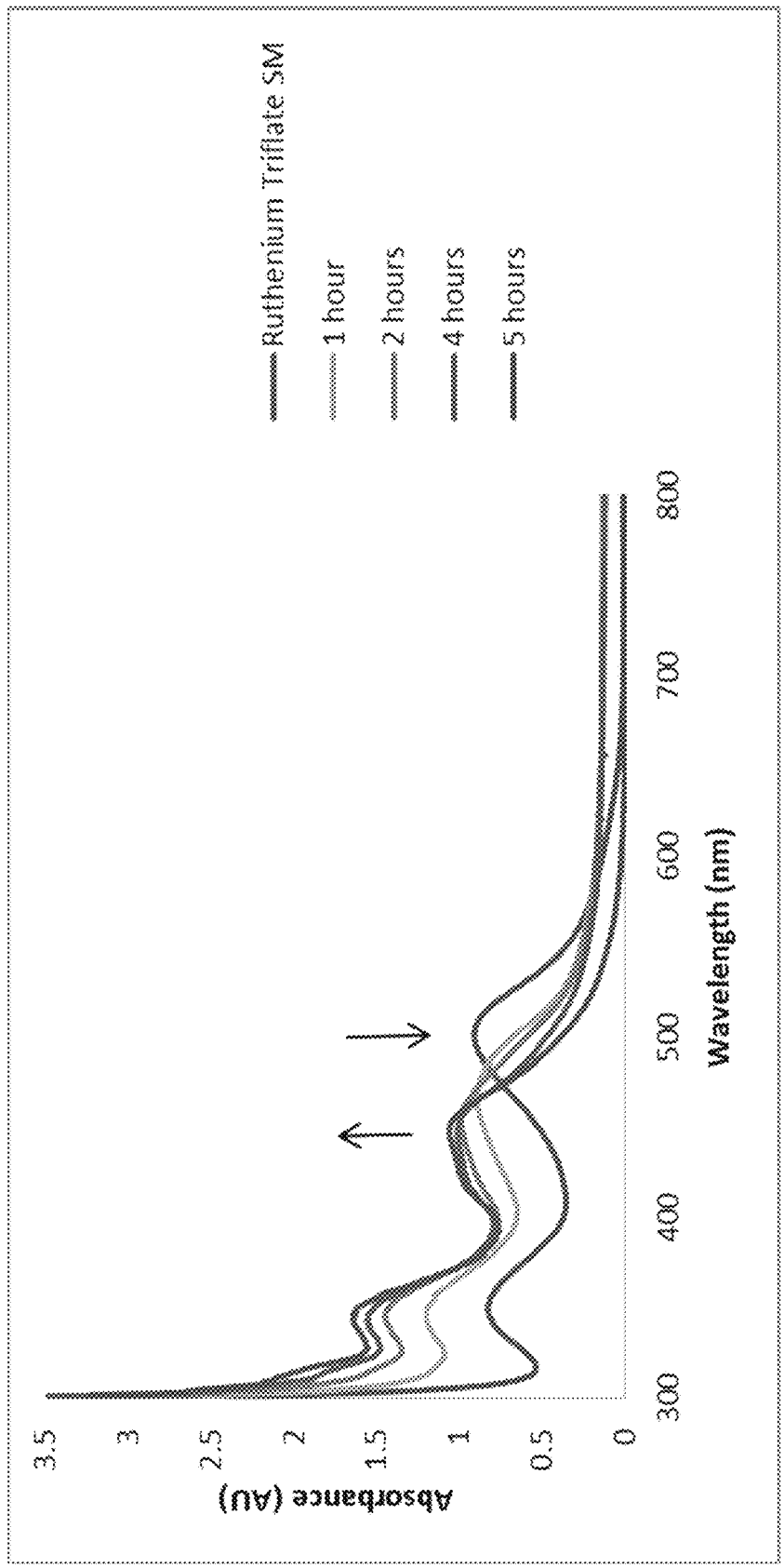
FIG. 2 is a spectrum depicting UV-Vis spectroscopy monitoring of the synthesis of RuBEP. The reaction solution was methanol heated to 75° C. The peak at 520 nm was due to Rubpy$_2$OTf, which disappeared as RuBEP was formed to give the double peak near 450 nm.
Figure 20:
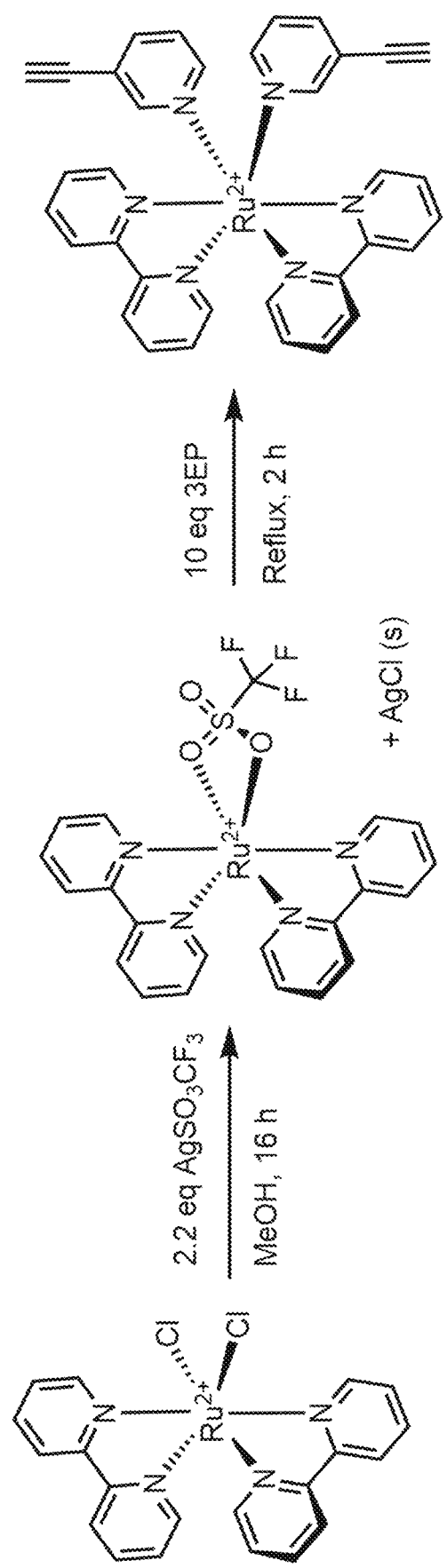
FIG. 20 is a scheme depicting an exemplary synthesis of RuBEP.
Figure 21:
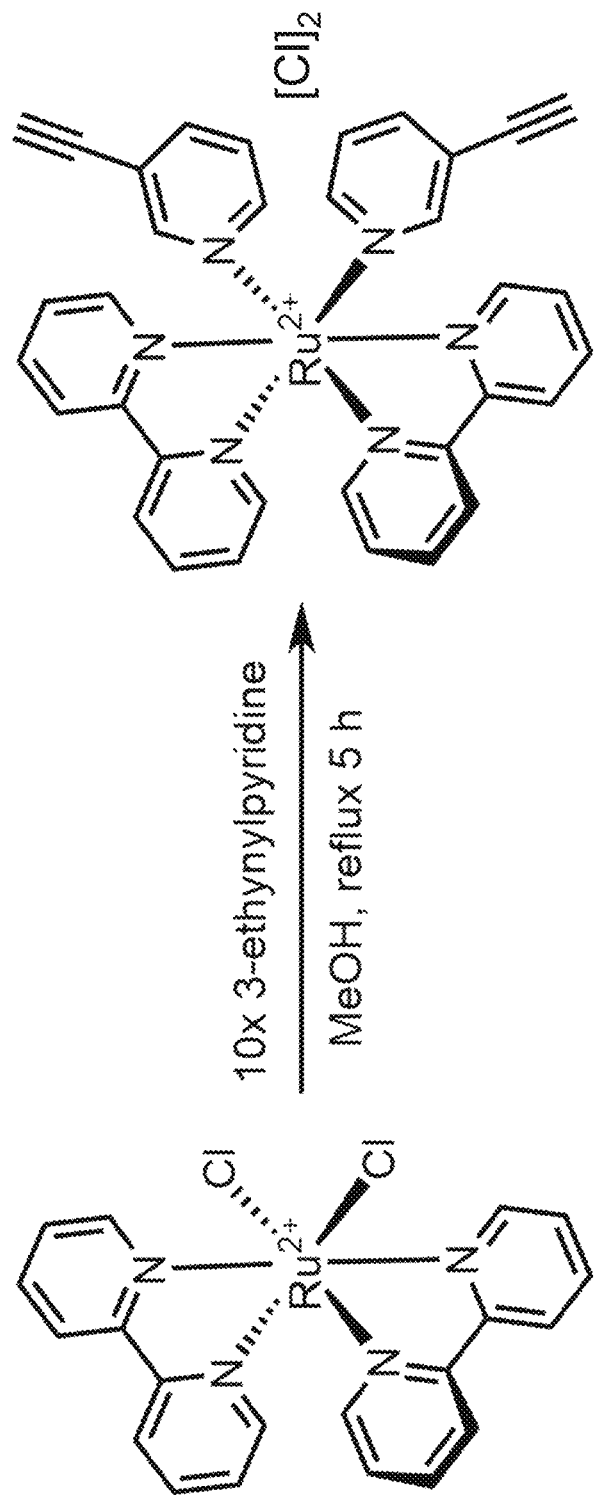
FIG. 21 is a scheme depicting an exemplary synthesis of RuBEP.
Figure 24:
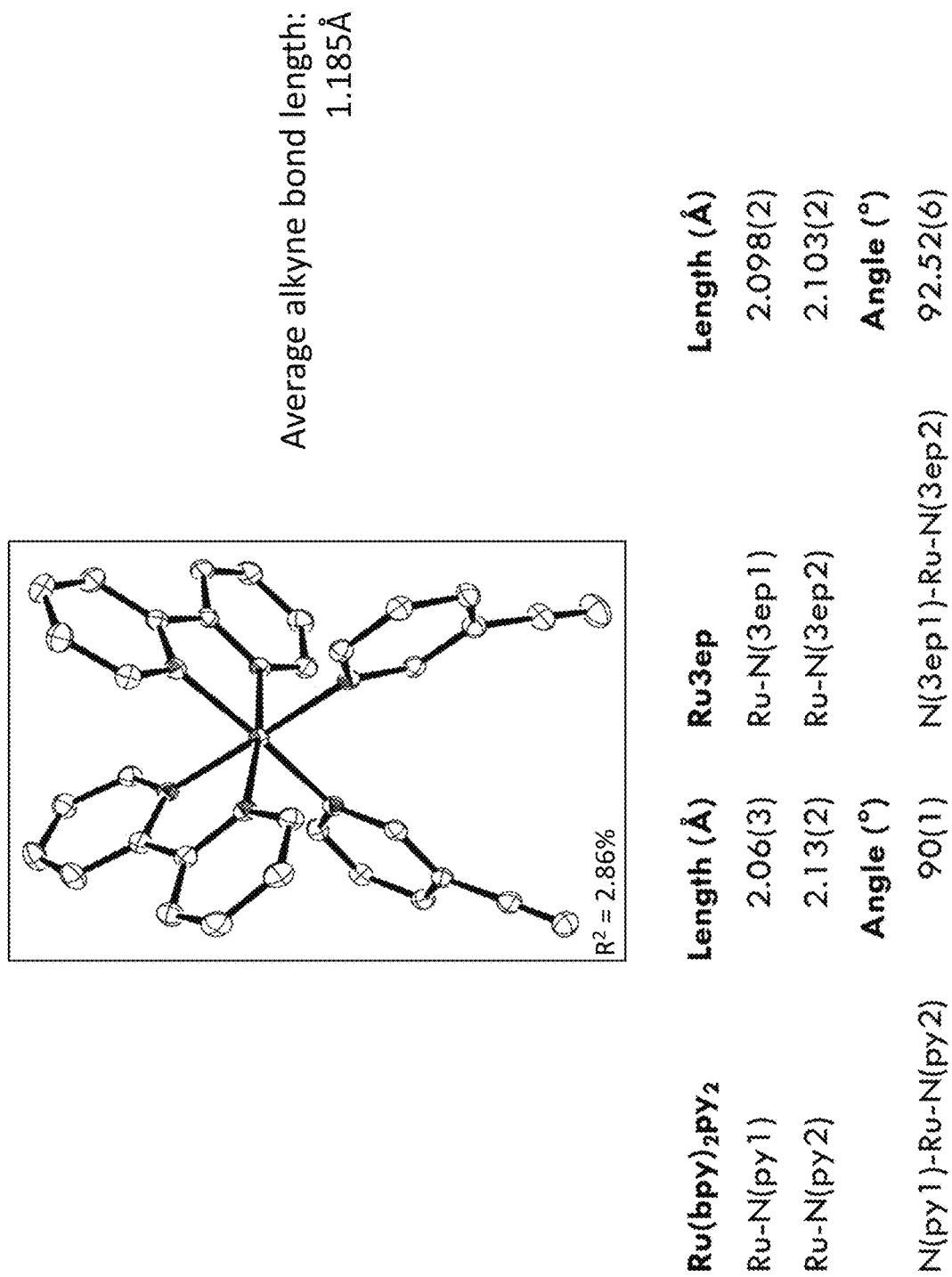
FIG. 24 is an image depicting the crystal structure of RuBEP.

The RuBEP photolinker was synthesized via a triflate intermediate from commercially available cis-Ru(bpy)$_2$Cl$_2$ and 3-ethynylpyridine (3EP) (See methods section above; also FIGS. 20-21 for exemplary syntheses) (Tang and Dmochowski, 2006, Angew. Chem., Int. Ed. Engl. 45:3523-3526). Reaction progress was monitored by UV-Vis spectroscopy until an MLCT band at 450 nm was observed (FIG. 2). The PF$_6^-$ salt (RuBEP[PF$_6$]$_2$), synthesized by metathesis with ammonium hexafluorophosphate in cold water, was purified in the dark by silica column chromatography using 1:9 acetonitrile:dichloromethane as the eluent. The water-soluble chloride salt (RuBEP) was then generated by metathesis with TBACl in cold acetone. Final yield of product was 60-70%. The identity and purity of RuBEP was confirmed by X-ray crystallography (FIGS. 3 and 24), ESI-MS (FIG. 4), $^1$H and $^{13}$C NMR, (FIG. 5), and elemental analysis. X-ray crystallography revealed standard $Ru^{2+}$—N bond lengths for the bipyridine and pyridine ligands. The $N_{3EP}$—Ru—$N_{3EP}$ bond angle was 92.5° and twisting of the two 3EP ligands positioned the alkynes (C40–C32=6.188(3) Å) for subsequent cycloaddition reactions.

Figure 4:
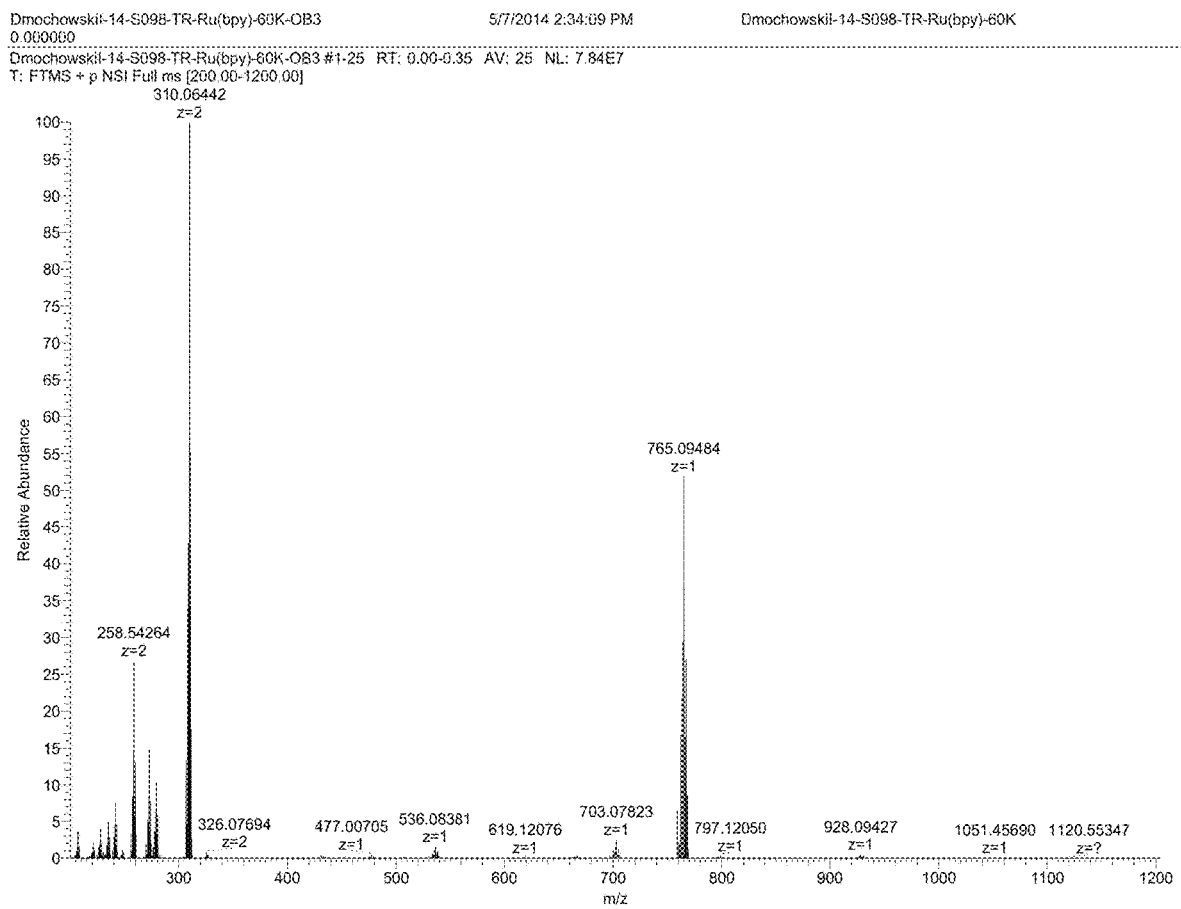
FIG. 4, comprising
Figure 5:
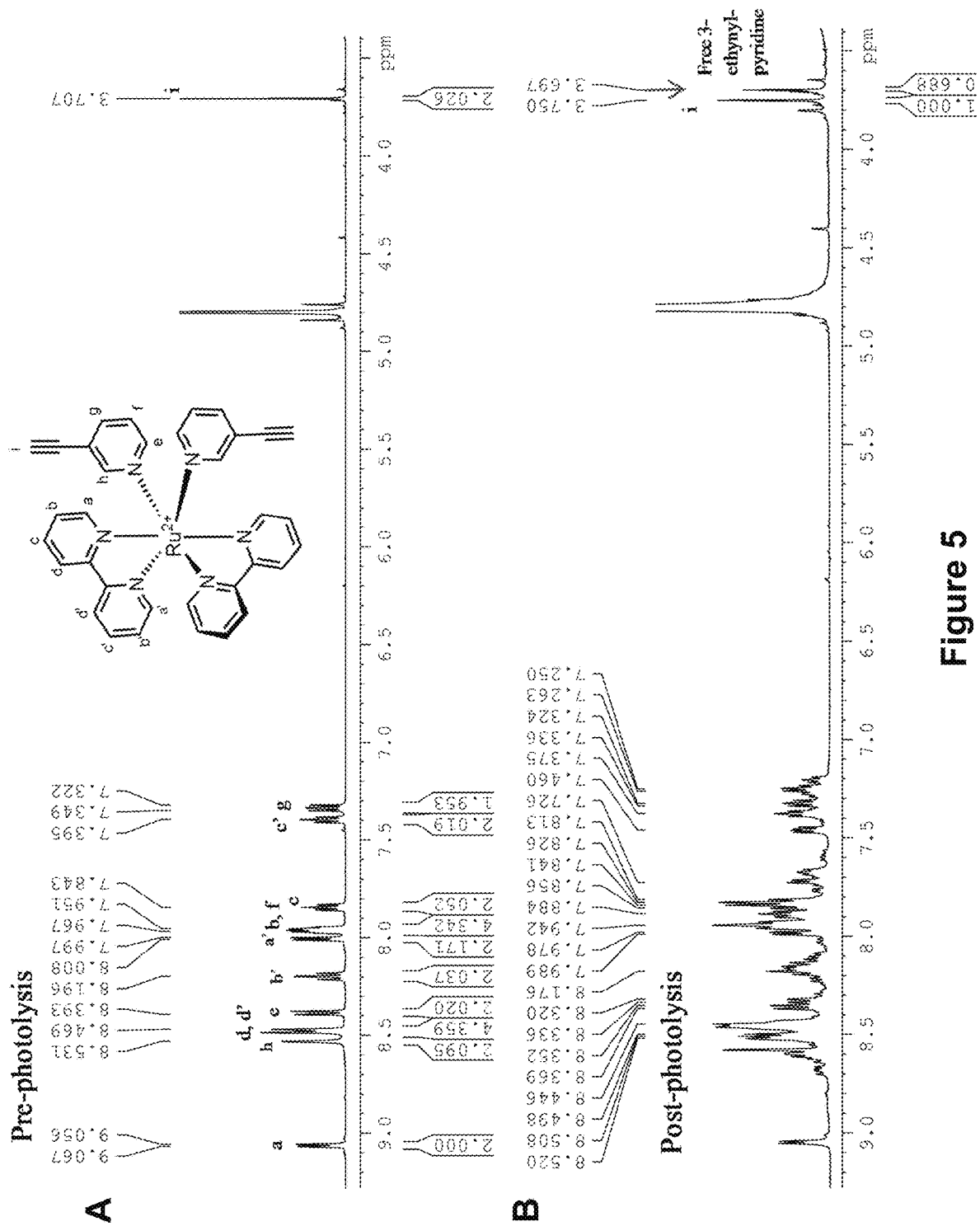
FIG. 5, comprising
Figure 6:
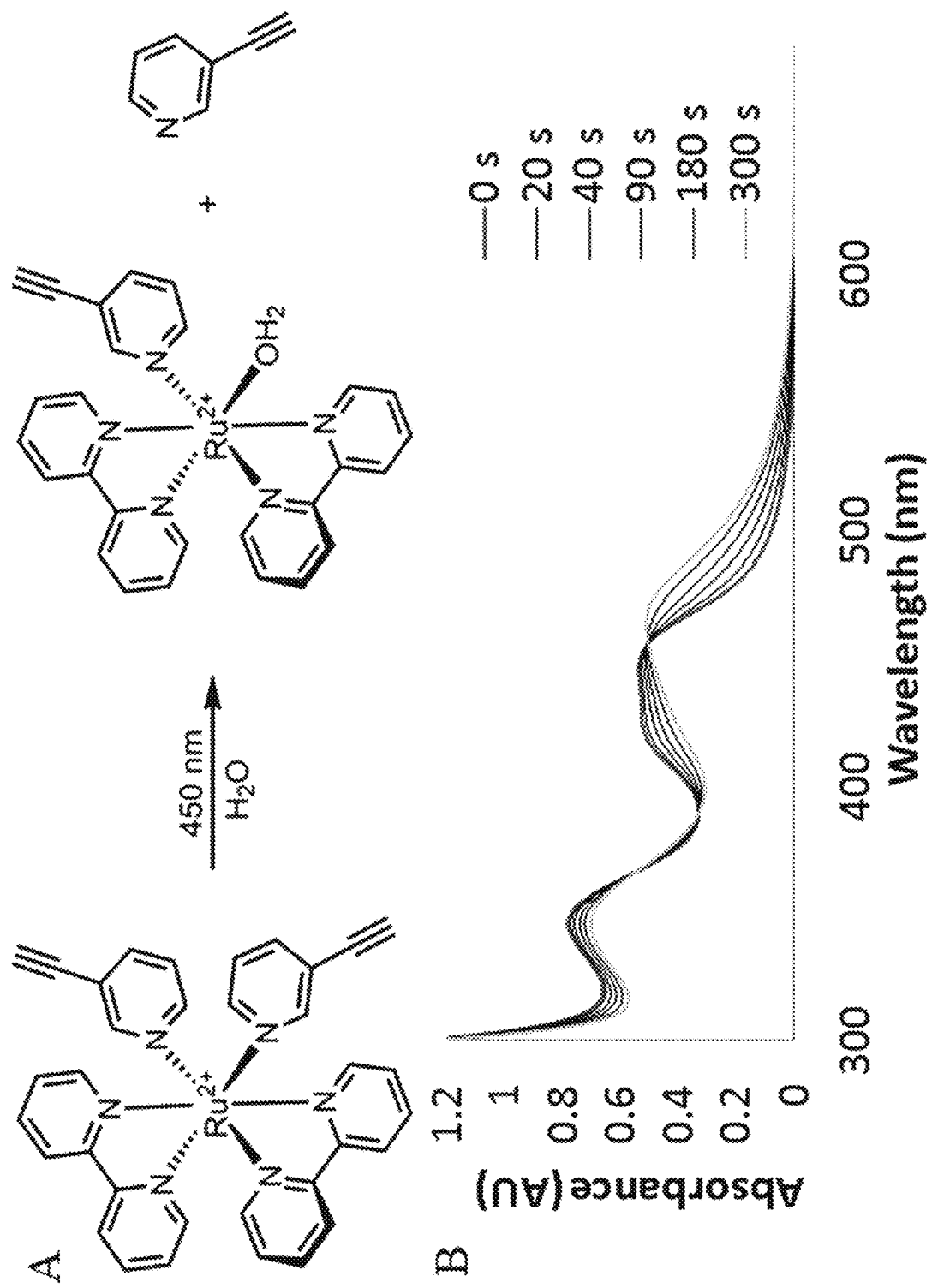
FIG. 6, comprising

Photodissociation of 3EP from RuBEP was monitored by LCMS (FIG. 4), UV-Vis (FIG. 6B) and $^1$H and $^{13}$C NMR (FIG. 5) spectroscopies. Upon continuous irradiation with 450-nm light (53 mW/cm$^2$, focused to 0.5 cm$^2$), the $\lambda_{max}$ red-shifted from 450 nm to 473 nm (FIG. 6B). Complete photolysis of the bulk RuBEP solution (80 μM, 1.5 mL, stirred) occurred in 5 min. The orange photo-product ([Ru(bpy)$_2$(3EP)(OH$_2$)]$^{2+}$ was consistent with previously characterized [Ru(bpy)$_2$(pyr)(OH$_2$)]$^{2+}$ complexes (Bryant and Mayer, 2003, J. Am. Chem. Soc. 125:10351-10361). Isosbestic points were observed at 450 nm and in the near-UV for the exchange of one pyridine ligand without forming rate-limiting intermediates (Sears et al., 2013, J. Inorg. Biochem. 121:77-87). $^1$H NMR also showed the exchange of only one 3EP ligand with a solvent water molecule, based on an observed shift in alkyne peak and change in integration (FIG. 5). HR-MS also confirmed the photoproduct assignment (FIG. 4). Finally, 1-cell-stage zebrafish embryos were microinjected with RuBEP and were observed to remain healthy and develop normally, whether incubated in the dark or irradiated with 450-nm light.

Figure 7:
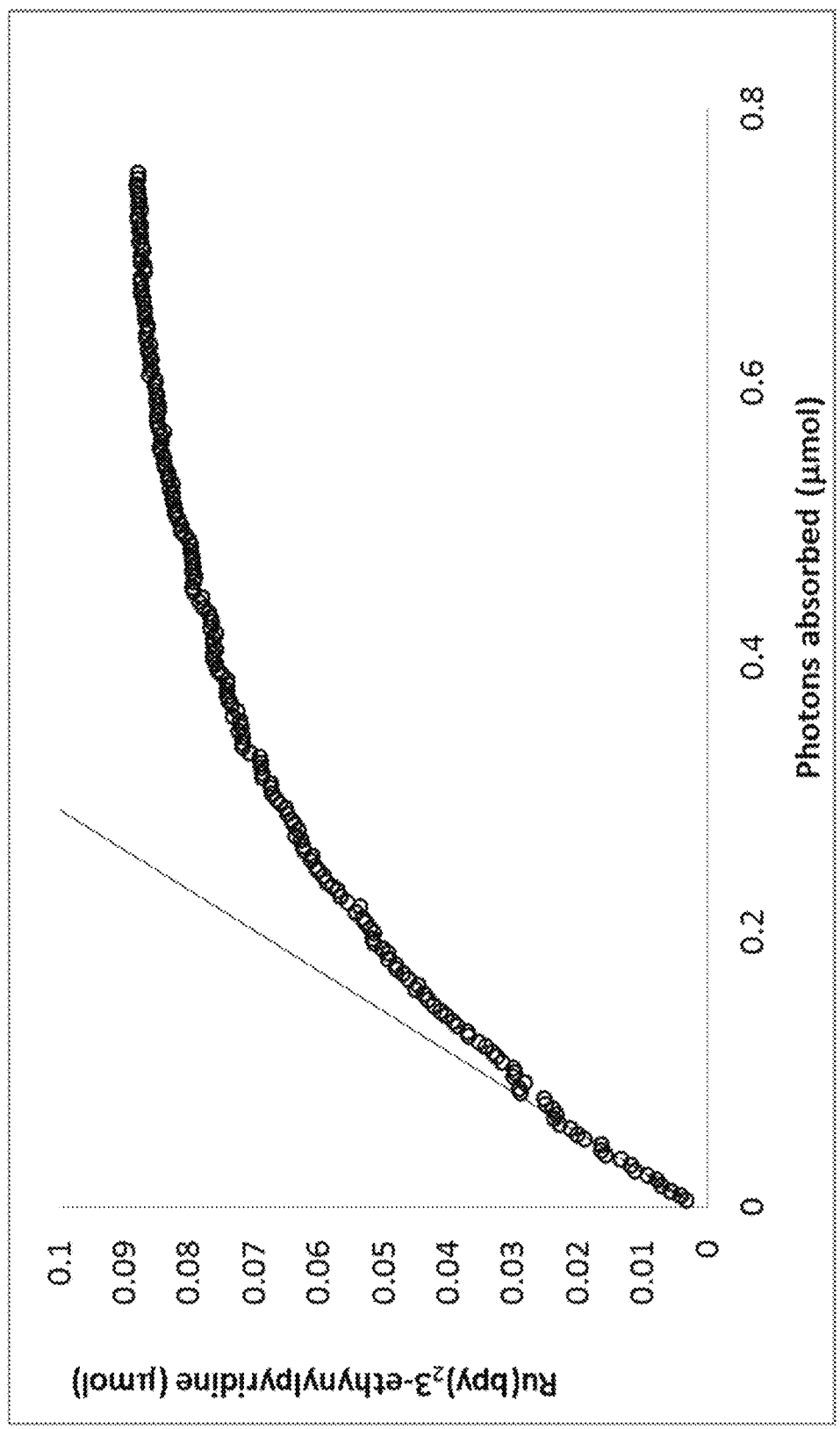
FIG. 7 is a graph depicting the kinetics trace of an exemplary photolysis reaction. Light source: 450 nm laser (14 mW/cm$^2$), 14 µM RuBEP in water, 0.2 OD. Quantum yield of photorelease=0.33±0.06.

The quantum yield of ligand exchange in water under ambient oxygen (φ=0.33+/−0.06) was determined by fitting the initial kinetics of the photoreaction (FIG. 7). This was comparable to the quantum yield of ligand exchange reported for Ru(bpy)$_2$(pyr)$_2$Cl$_2$ (φ=0.4) (Zayat et al., 2003, J. Am. Chem. Soc. 125:882-883). The uncaging efficiency for RuBEP ($\varepsilon_{450}$ times φ) was determined to be 2.0×10$^3$ M$^{-1}$ cm$^{-1}$ at 450 nm, which is much higher than measured for typical organic chromophores activated at near-UV wavelengths. Commonly used nitrobenzyl derivatives, for example, have uncaging efficiencies less than 100 M$^{-1}$ cm$^{-1}$ at 365 nm. (Gatterdam et al., 2014, Angew. Chem., Int. Ed. 53:5680-5684; Furuta et al., 1999, Proc. Natl. Acad. Sci. U.S.A. 96:1193-1200). The formula for fitting the initial kinetics of the photoreaction is as follows:

$$\text{Moles Product Ru(bpy)}2{3EP}(OH_2) = \text{initial moles RuBEP} - \text{current moles RuBEP} \quad (1)$$

$$\text{current moles RuBEP} = \left(\frac{Abs - \varepsilon_p[RuBEP]_i}{\varepsilon_S - \varepsilon_p}\right) \times V_{cuvet} \quad (2)$$

$$\text{photons absorbed} = \frac{E}{P_1} \quad (3)$$

Figure 8:
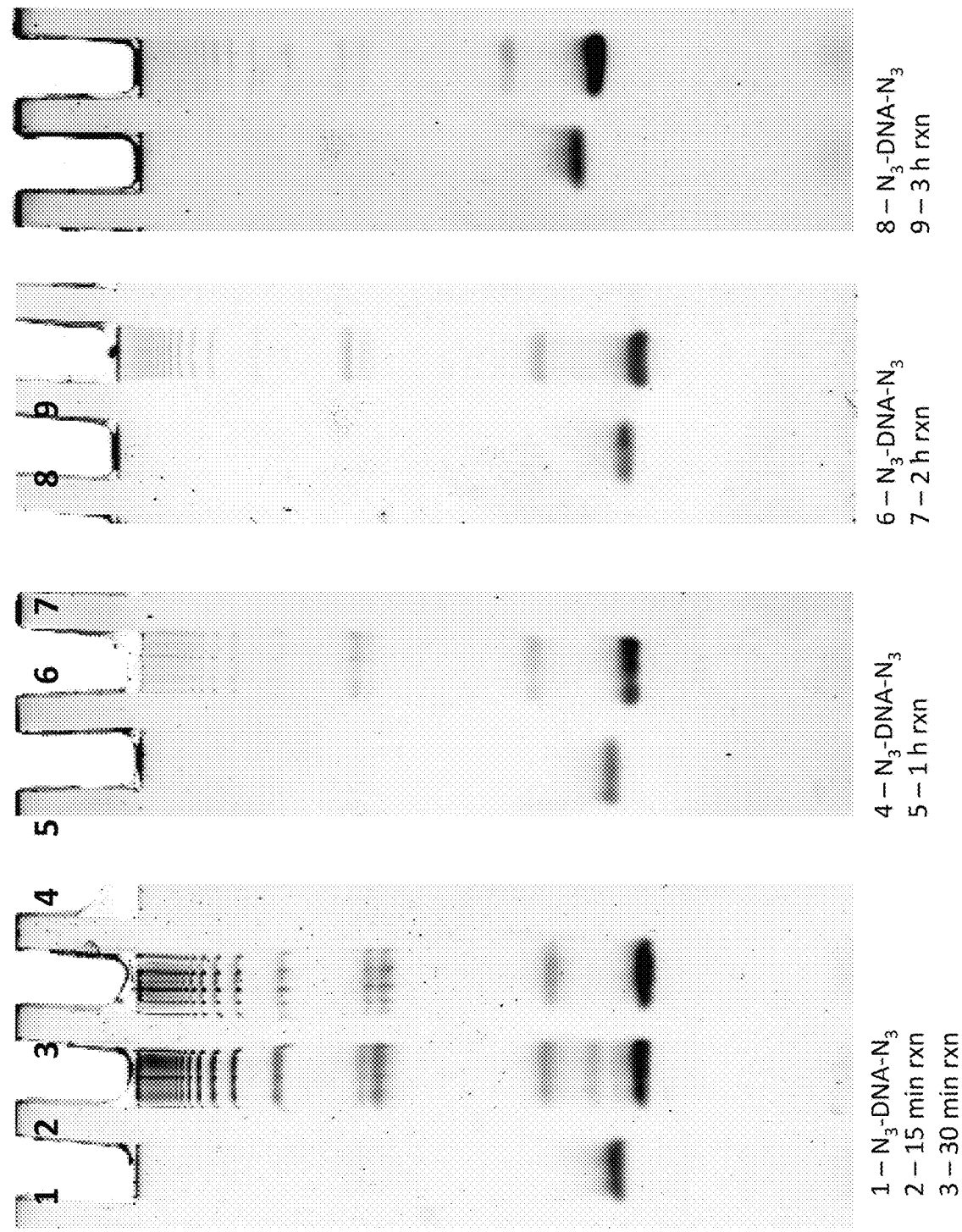
FIG. 8 is a series of time-course gels demonstrating DNA circularization. 25 pmol aliquots were removed over the course of the DNA circularization reaction. Each aliquot was run on a 15% PAGE/7M urea gel at 300 V for 45 min and stained for 15 min with EtBr. Click reaction aliquots were compared to the linear bis-azido DNA migration (lanes 1, 4, 6, 8). Circular product appeared as the fastest migrating band, within the first 15 min of the reaction, with more product formation at 3 h (lane 9).
Figure 9:
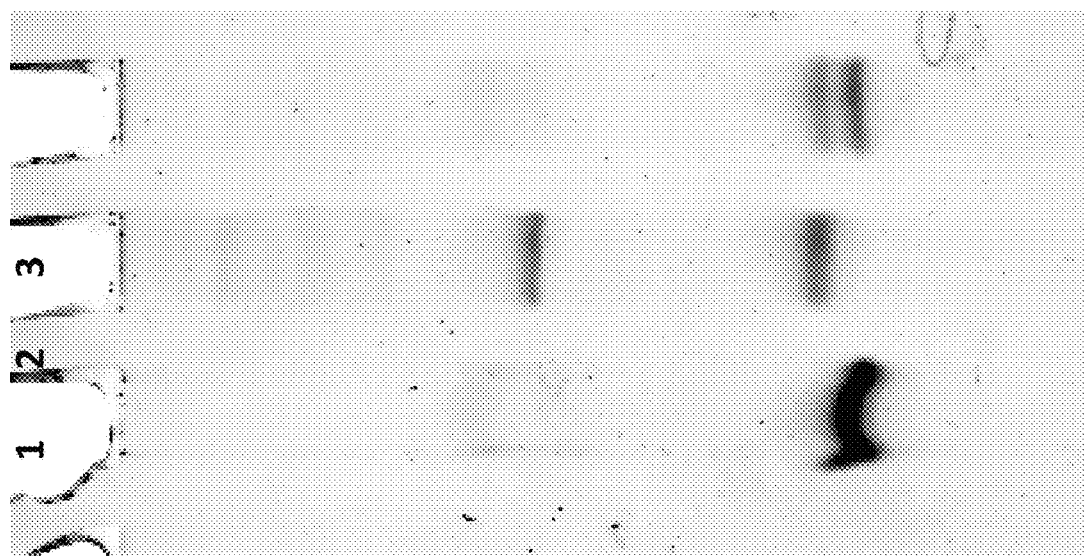
FIG. 9 is an image of a gel depicting results of an exemplary mono-azide DNA click reaction. A mono-azido DNA 25mer was subjected to the same conditions described in FIG. 8 for the bis-azide DNA. The circularization efficiency was monitored on a 15% PAGE/7 M urea gel, run for 45 min at 300 V. The gel was stained for 15 min with EtBr. A band (lane 3) running slower than the N3-DNA appeared, and intensity was decreased after photolysis. Only a 50% decrease in photoloysis was seen, as only one 3EP ligand on RuBEP will exchange upon light exposure. The higher band in lane 2 is likely DNA-RuBEP-DNA.
Figure 10:
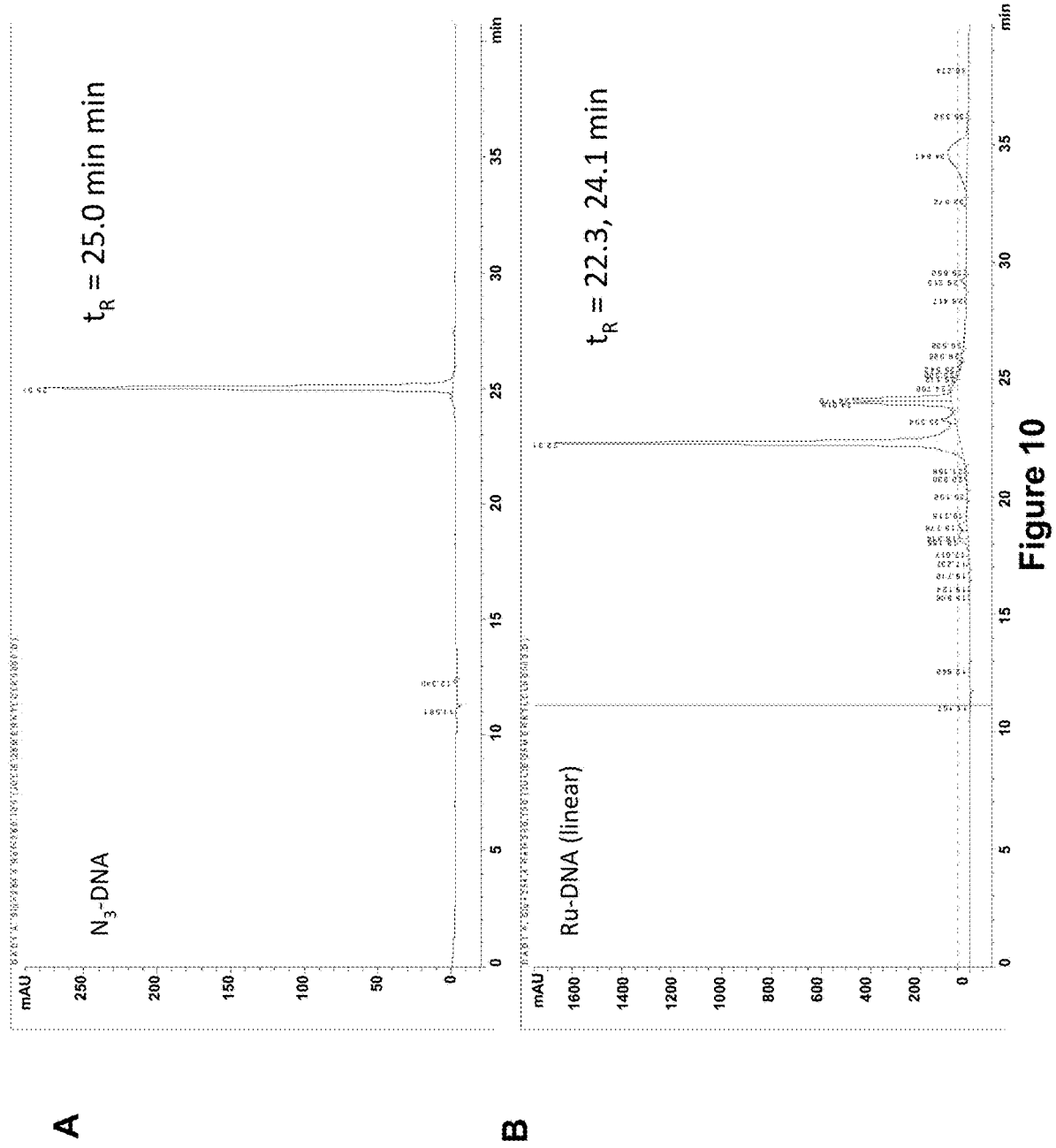
FIG. 10, comprising
Figure 10:
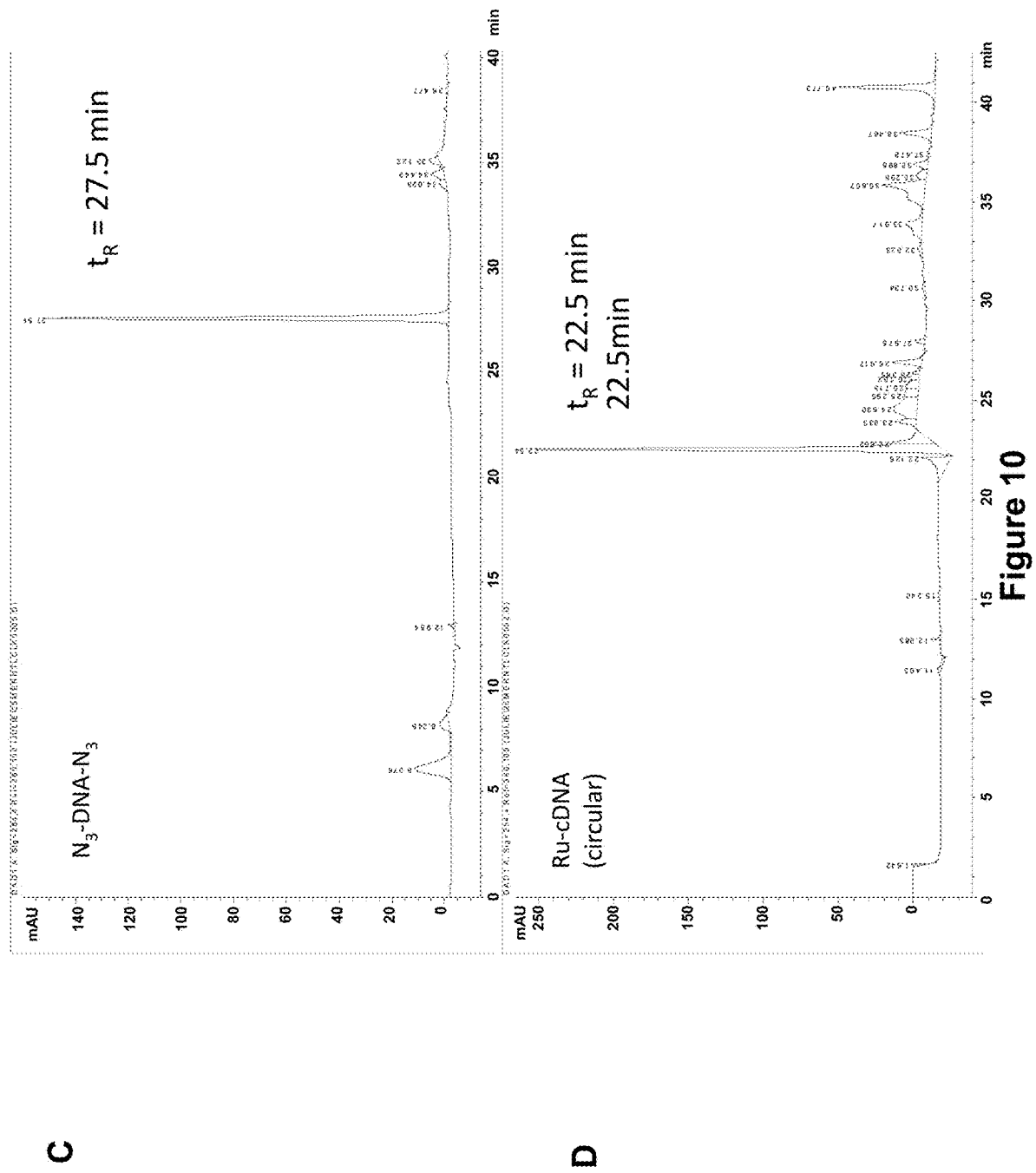
Figure 11:
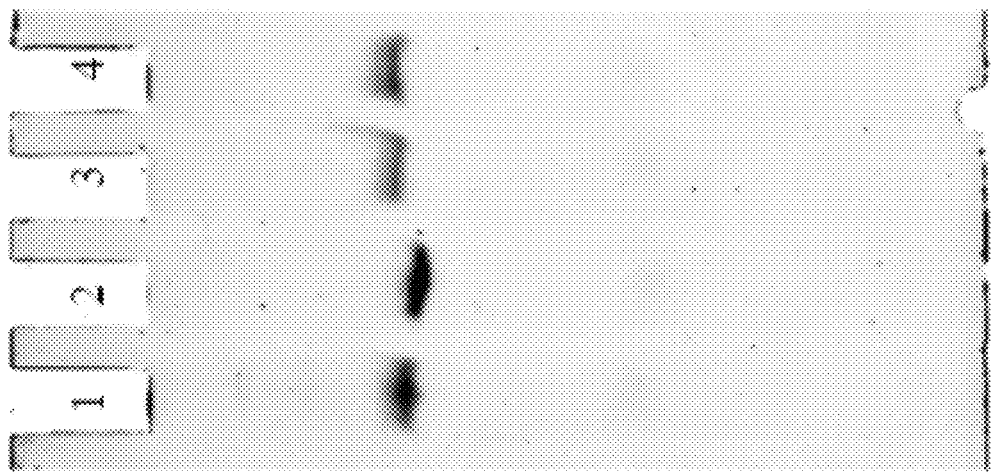
FIG. 11 is an image of a 20%, 7 M urea PAGE analysis of Ru-cDNA after HPLC purification. Lane 1 represents linear DNA (TR=27.5 min). Lane 2 represents Ru-DNA after HPLC purification (TR=22.5 min). Lane 3 represents Ru-DNA+450 nm light (3 min). Lane 4 represents Ru-DNA+450 nm light, after 24 h. Gel (lane 4) shows no recombination after 24 h sitting at room temperature (21° C.). The band corresponding to uncaged, linear DNA (lane 3) shows no difference between immediate irradiation and 24 h post-irradiation (lane 4). Denaturing gel: 15% PAGE/7M urea, 300 V, 45 min.
Figure 22:
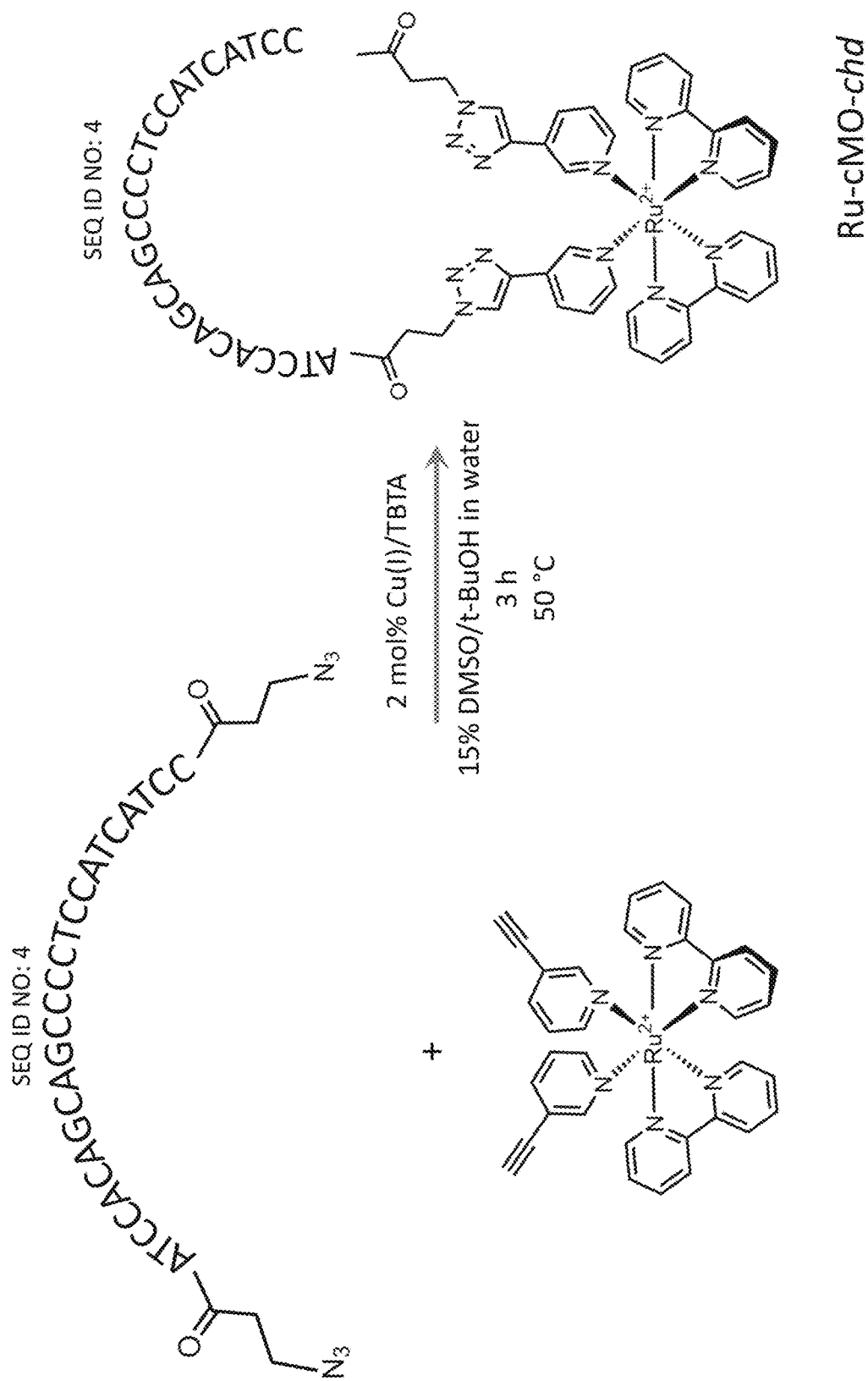
FIG. 22 is a scheme depicting an exemplary synthesis of Ru-cMO-chd using a [3+2] copper-mediated azide-alkyne cycloaddition with a 25-mer morpholino.
Figure 23:
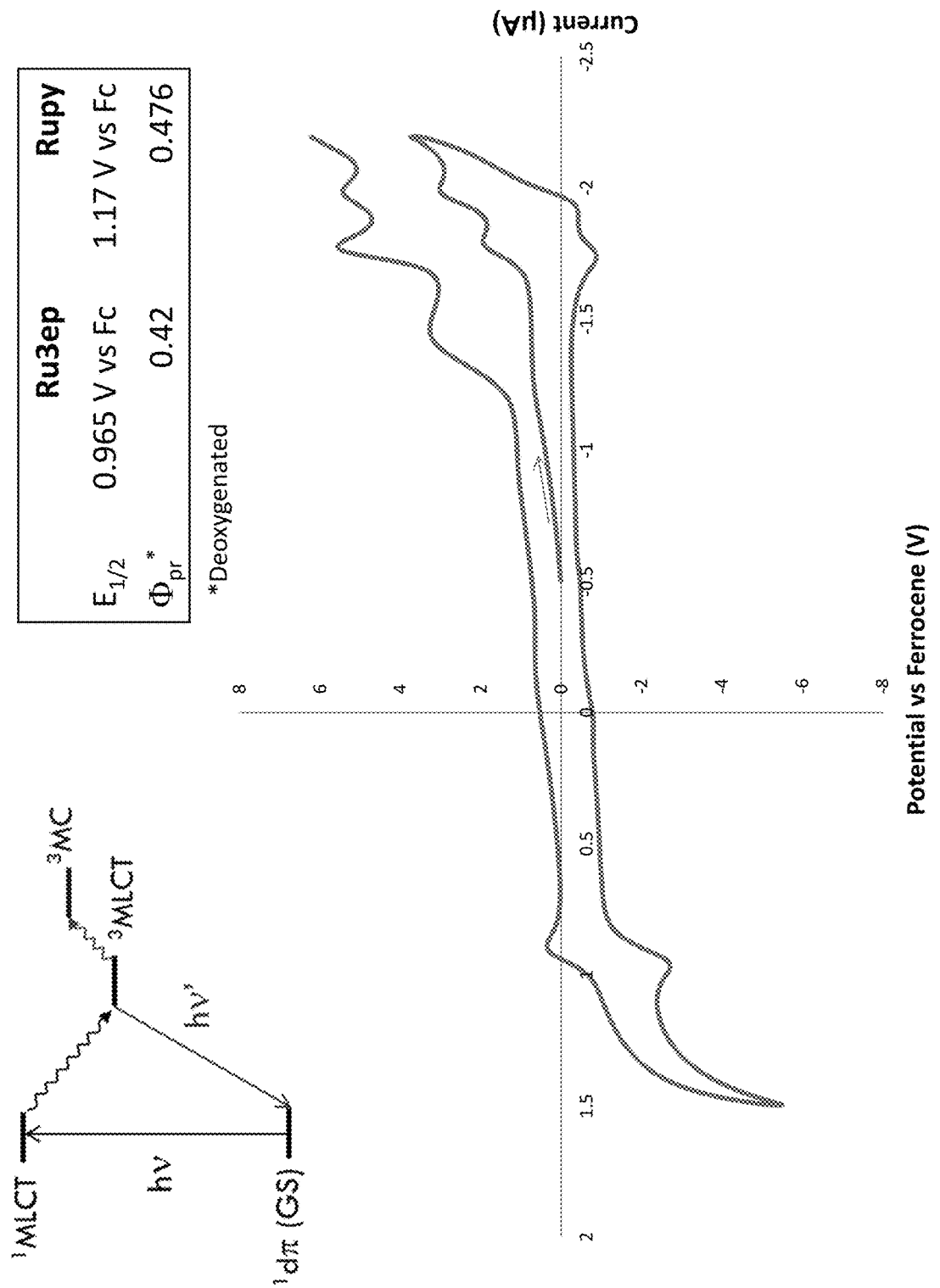
FIG. 23 is a graph depicting the electrochemistry of RuBEP.

Where:
$P_1$=net power of the laser during the trial (mW)
E=energy of 450 nm light (J/photon)
$\varepsilon_s$=extinction coefficient of RuBEP (starting material) at 475 nm=1800 M$^{-1}$cm$^{-1}$
$\varepsilon_p$=extinction coefficient of Rubpy$_2$(3EP)(H$_2$O)(product) at 475 nm=3800 M$^{-1}$cm$^{-1}$ Using RuBEP as photolinker, circularization protocols were initially investigated using a bis-azido 25mer DNA oligonucleotide. The [3+2] Cu(I)-mediated cycloaddition reaction was performed at a stoichiometry of 1.2 DNA:1 RuBEP, in the presence of 10×CuBr and 20× chelator tris(benzyltriazolylmethyl)amine (TBTA) and and monitored by polyacrylamide gel electrophoresis (PAGE). A band migrating faster than the bis-azido DNA appeared within the first 15 min of reaction (FIG. 8) consistent with RuBEP inducing a more compact, circular structure and contributing positive charge. The reaction was complete within 3 h and quenched by NAP-5 desalting column. To confirm that this was the circular DNA (cDNA) and not RuBEP clicked to two linear DNA oligos, a mono-azido DNA was subjected to the same reaction conditions, which resulted in a slower migrating band (FIG. 9). The reaction product was readily isolated by reverse-phase HPLC in 20-25% yield (FIGS. 10-11; Table 9), and confirmed by MALDI-TOF MS (FIG. 30; Table 10). After 3 min irradiation with 450 nm light emitting diode (14 mW cm$^{-2}$, beam area=12.6 cm$^2$) this band migrated at the same rate as the linear DNA, suggesting full conversion to the active, linear species. No changes to the photoproduct (including reversion to the circular Ru-DNA) were observed after 24 h in solution under ambient conditions (FIG. 11). FIG. 22 depicts an exemplary synthesis of Ru-cMO-chd.

TABLE 9

Gradient used for Ru-DNA and Ru-cDNA HPLC purification

| Time (min) | % Acetonitrile | % 0.05M TEAA |
|---|---|---|
| 0.0 | 90 | 10 |
| 40.0 | 40 | 60 |
| 50.0 | 20 | 80 |

Figure 14:
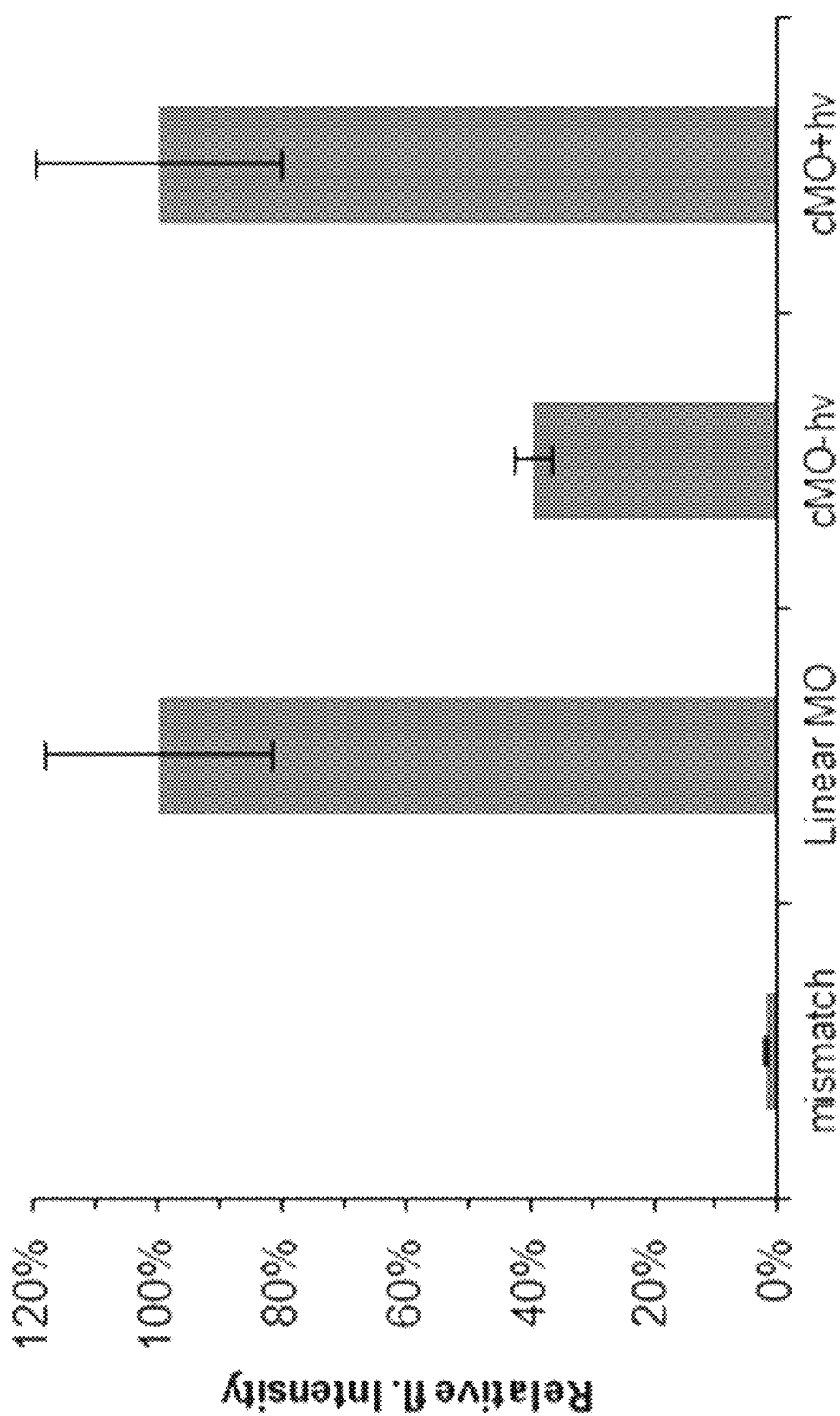
FIG. 14 is a graph demonstrating the results of a molecular beacon fluorescence assay showing relatively little probe hybridization to caged Ru-cMO compared to the linear MO or Ru-cMO after 3-min exposure to 450-nm light.

Caging was confirmed through a molecular beacon assay (FIG. 12), in which a stem-loop, reverse complementary probe with fluorophore-quencher pair was incubated with oligo samples for 20 min at 25° C. The degree of DNA-beacon hybridization, determined by relative fluorescence intensity, was nearly zero for a mismatched sequence, and scaled to 100% for the linear, fully complementary DNA (FIG. 14). Only 5% beacon fluorescence was observed with Ru-DNA vs. fully restored fluorescence after 3 min irradiation with 450 nm light (14 mW cm$^{-2}$), consistent with complete uncaging.

The RuBEP-oligo circularization conditions were subsequently applied to antisense MOs, in order to photoregulate gene expression in living zebrafish embryos (FIG. 1). Two early developmental zebrafish genes were targeted, chordin (chd) and notail (ntl), due to their well characterized and easily recognizable knockdown phenotypes with antisense MOs (Nasevicius and Ekker, 2000, Nat. Genet. 26:216-220). Bis-azido MOs were purchased from Gene Tools (Philomath, Oreg.) and added to RuBEP in a 1.05:1 ratio in the presence of 10× Cu(I)Br and 20× chelator, tris(benzyltriazolylmethyl)amine (TBTA). The reaction proceeded at rt for 18 h. These conditions promoted reaction of one RuBEP per MO, thus favoring intramolecular reaction and circularization. Higher molecular weight Ru-MO polymers precipitated under the reaction conditions and were removed by centrifugation. Excess reagents (RuBEP, Cu, TBTA, and solvents) were removed with NAP-5 column, leaving pure Ru-MO in water (isolated yield=20-30%). Mass confirmation was obtained by MALDI-TOF MS (Table 10)

Figure 12:
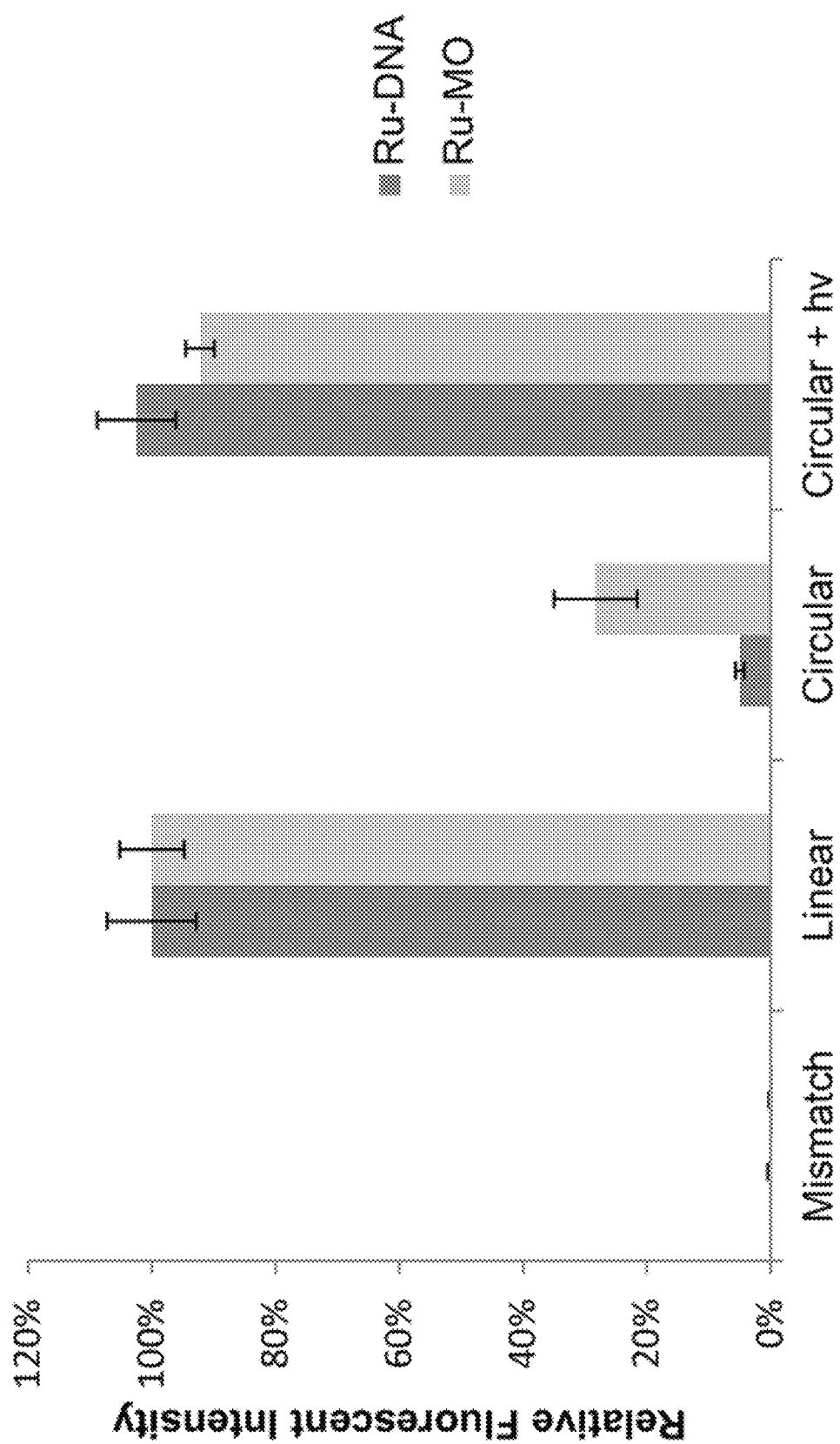
FIG. 12 is a graph depicting experimental data from a molecular beacon assay showing near complete caging of circular Ru-DNA and Ru-MO, with restoration of fluorescence intensity after photoactivation. Molecular beacon hybridization assay for Ru-cDNA. The data demonstrates decreased fluorescence intensity prior to irradiation, indicative of inhibited beacon-DNA duplex formation, and full restoration of fluorescence intensity (comparable to the complementary linear control) after 3-min irradiation (450 nm, 14 mW/cm$^2$). A molecular beacon (Integrated DNA Technologies, Coralville, Iowa), complementary to the zebrafish ntl MO sequence was designed, with fluorophore, 6-FAM on the 5' end and quencher, BHQ1 on the 3' end. Caging, indicative of circularization, was monitored by the opening of the molecular beacon in the presence of oligonucleotide. Ru-cDNA was hybridized to the molecular beacon, and fluorescence intensity at 523 nm was quantified. For comparison, the fully complementary linear bis-azido DNA as well as a DNA mismatch sequence, were also monitored. Circularization and caging of the Ru-cDNA was confirmed by a 2.3-fold lower fluorescence intensity when compared to the linear complementary DNA. The Ru-cDNA was then exposed to 450 nm light for 3 min, and rehybridized to the molecular beacon. After visible light exposure, fluorescence intensity was restored to match the intensity of the bis-azido complementary DNA. This result demonstrates complete uncaging and hybridization restoration upon short exposure to blue light. All solutions were made to 1 pmol/µL with a 50 µL volume. All samples were prehybridized prior to analysis, by heating to 80° C. for 30 min, and immediately incubating on ice for 10 min. Samples were analyzed at 10° C.
Figure 13:
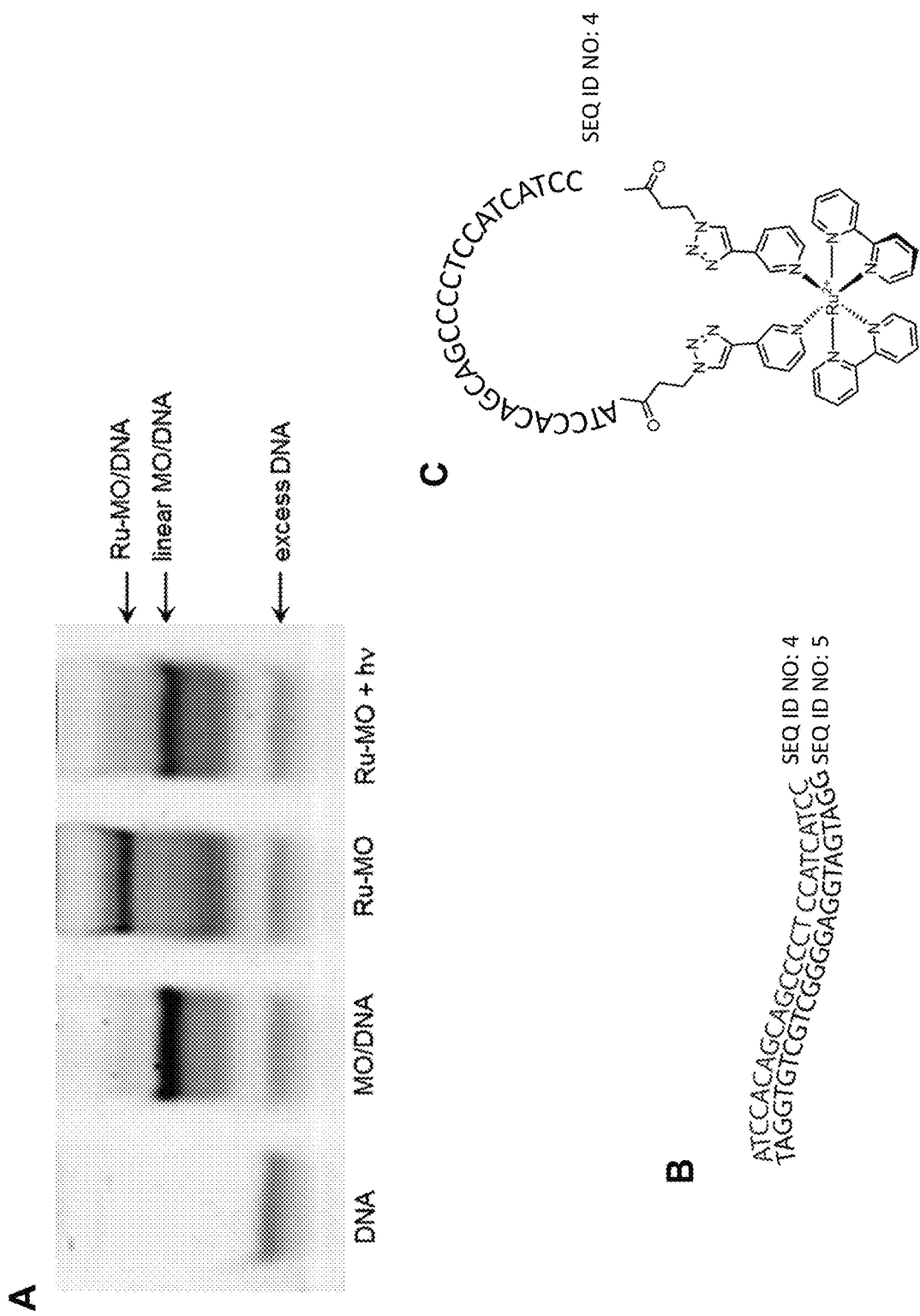
FIG. 13, comprising

Ru-MO formation was assessed by gel-shift assay employing a 25mer complementary DNA strand (FIG. 13). Due to the neutral charge of morpholinos, Ru-MO-chd and Ru-MO-ntl could not be analysed using standard PAGE or HPLC as Ru-DNA was. Thus, a Ru-MO:DNA hybrid was formed by heating to 80° C. and cooling to 4° C., run on a 15% native polyacrylamide gel on ice (100 V, 120 min) and stained with ethidium bromide (FIG. 13A). The complementary DNA (lane 1) ran slower when hybridized to linear MO (lane 2). Upon circularization (lane 3), the u-MO-chd-DNA hybrid migrated even slower, which was due to its secondary structure and reduced affinity for complementary DNA. Photoactivation at 450 nm (14 mW/cm$^2$, 3 min) resulted in complete uncaging, yielding a mono-Ru-functionalized linear MO that was hybridized to DNA (lane 4) and ran comparably to the linear MO:DNA hybrid (lane 2); the pendant Ru$^{2+}$ moiety (in lane 4) had no apparent effect. All lanes contained a slight excess of complementary DNA (lowest band) to promote hybridization. QuantIT band quantification showed less than 5% unreacted bis-azido MO after 18 h RuBEP reaction. A molecular beacon assay was similarly used to confirm caging of the Ru-MO construct, with only 28% fluorescence intensity observed relative to the linear control (FIG. 12). Different beacon designs produced varying levels of background fluorescence for the Ru-MO-chd constructs, but in all cases significant modulation of fluorescent signal was observed, consistent with Ru-oligo caging and uncaging.

MO-chd or Ru-cMO-chd (514 pmol/μL) was microinjected into 1-cell-stage zebrafish embryos, which were incubated at 28° C. in the dark and at 24 hours post-fertilization (hpf), scored for phenotypic response and imaged using a previously reported method (Westerfield, from "The Zebrafish Book. A guide for the Laboratory Use of Zebrafish (Danio rerio)." 4$^{th}$ ed.; University of Oregon Press, 2000). Embryos scored as normal had V-shaped somites, and normal head and tail development. The chordin knockdown phenotype ranged from severe to mild where severe was identified by decreased head size, U-shaped somites, and a large blood island on the tail. The moderate and mild phenotypes were identified by U-shaped somites and a medium or small blood island on the tail.

Figure 15:
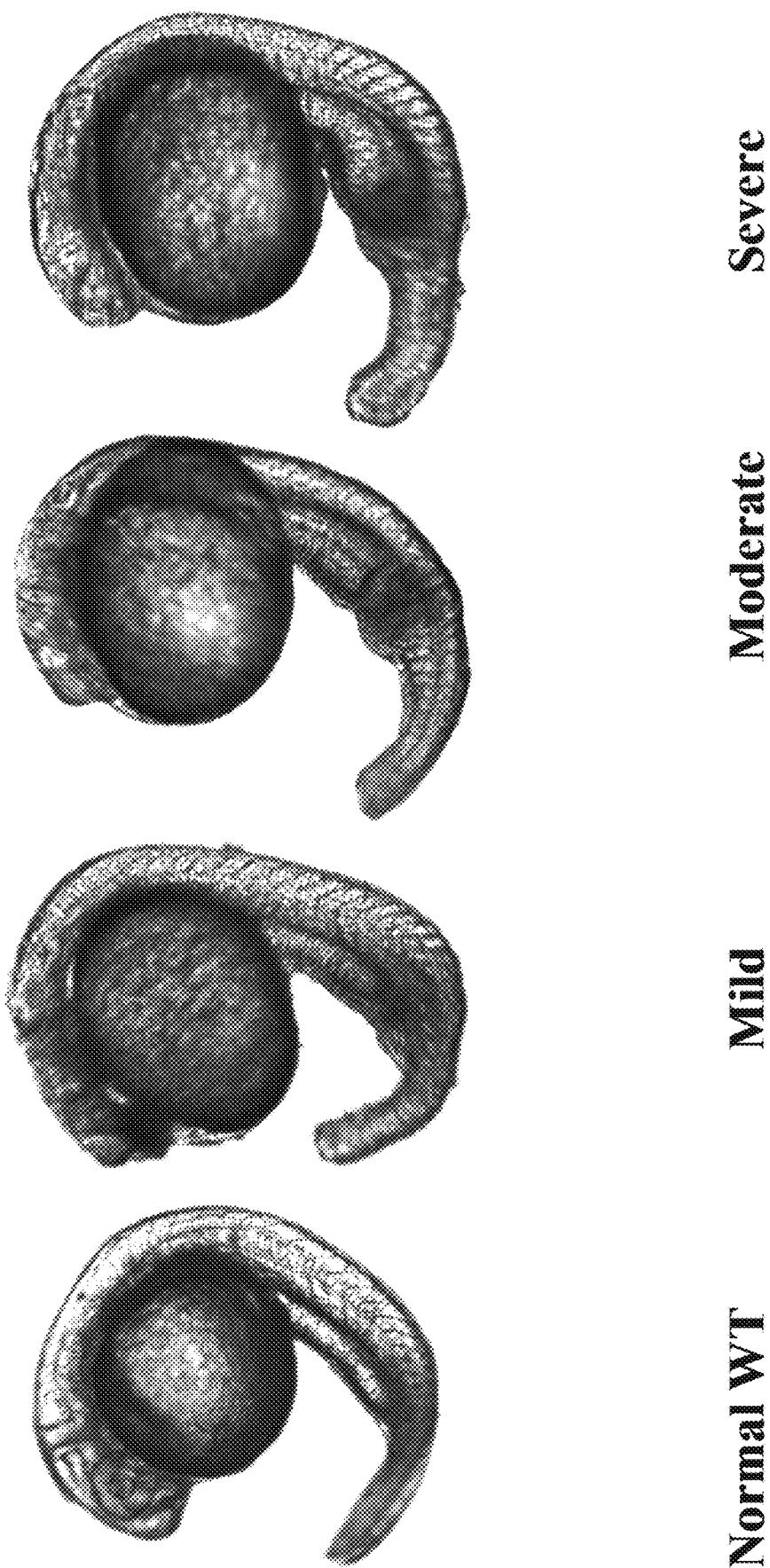
FIG. 15 is a series of images depicting zebrafish, including the chd-MO knockdown phenotype. Zebrafish embryos were injected at the 1-cell stage with 0.51 mM chd-MO and imaged at 24 hpf. The chordin morpholino knockdown phenotype ranged from severe to mild. Embryos scored as normal had V-shaped somites, and normal head and tail development. Severe was identified by decreased head size, U-shaped somites, and a large blood island on the tail. The moderate and mild phenotypes were identified by U-shaped somites and a medium or small blood island on the tail.
Figure 16:
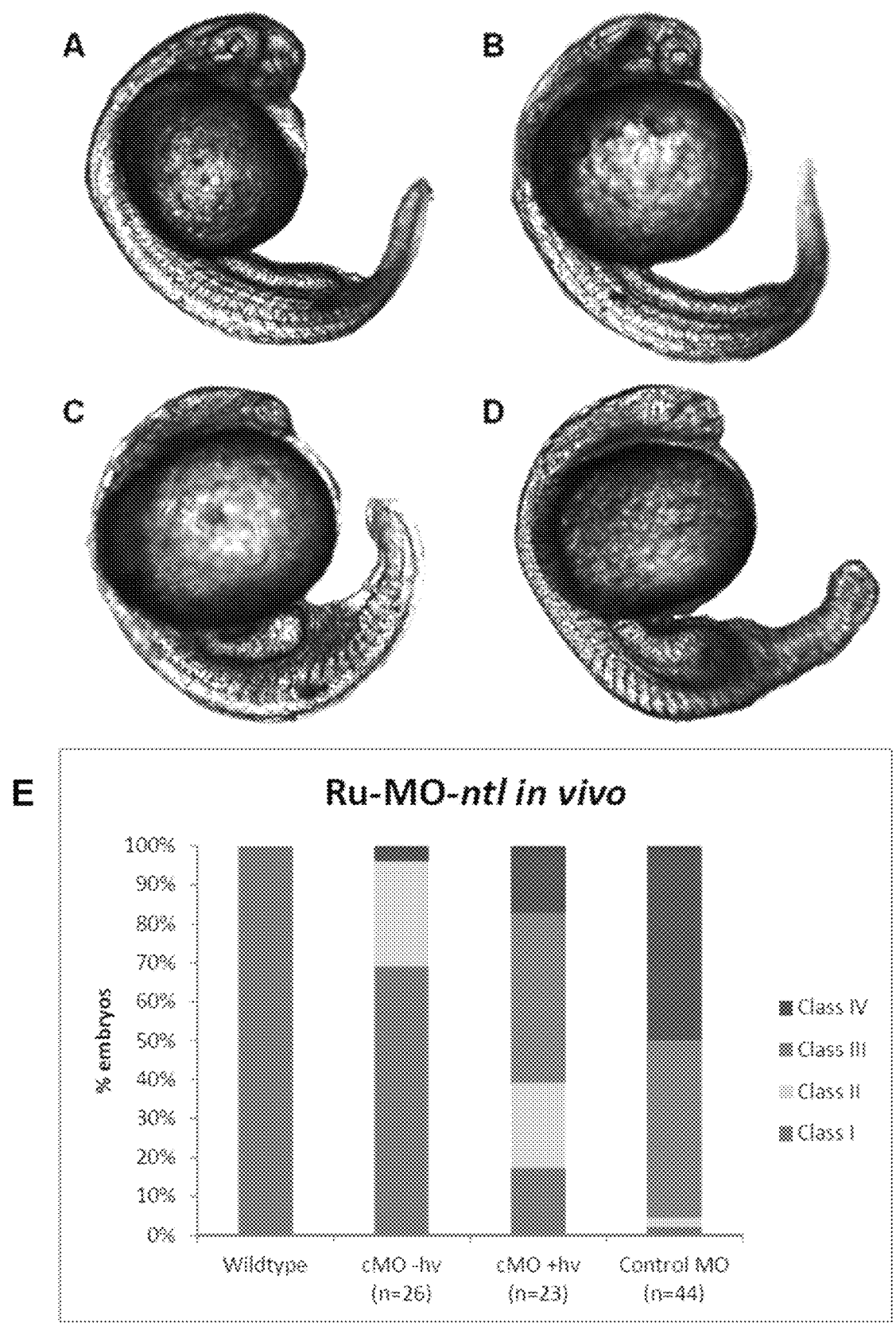
FIG. 16, comprising
Figure 17:
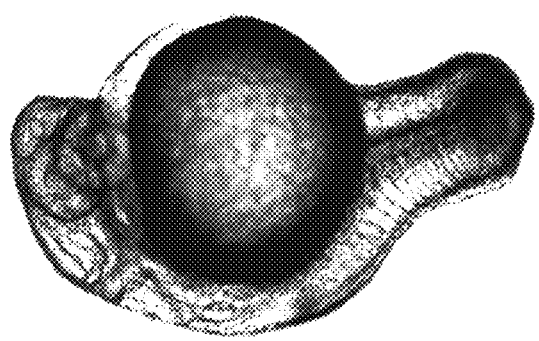
FIG. 17 is a series of images depicting zebrafish, including the ntl-MO knockdown phenotype. Zebrafish embryos were injected at the 1-cell stage with 0.25 mM ntl-MO and imaged at 24 hpf. The notail morpholino knockdown phenotype ranged from severe (class 4) to mild (class 2) where severe was identified by a significantly decreased head size, U-shaped somites, no notochord, and no posterior structures. Class 3 was identified by U-shaped somites, no notochord, and significantly shortened posterior structures. Class 2 was identified by U-shaped somites, a shortened posterior axis, with the notochord still present.
Figure 18:
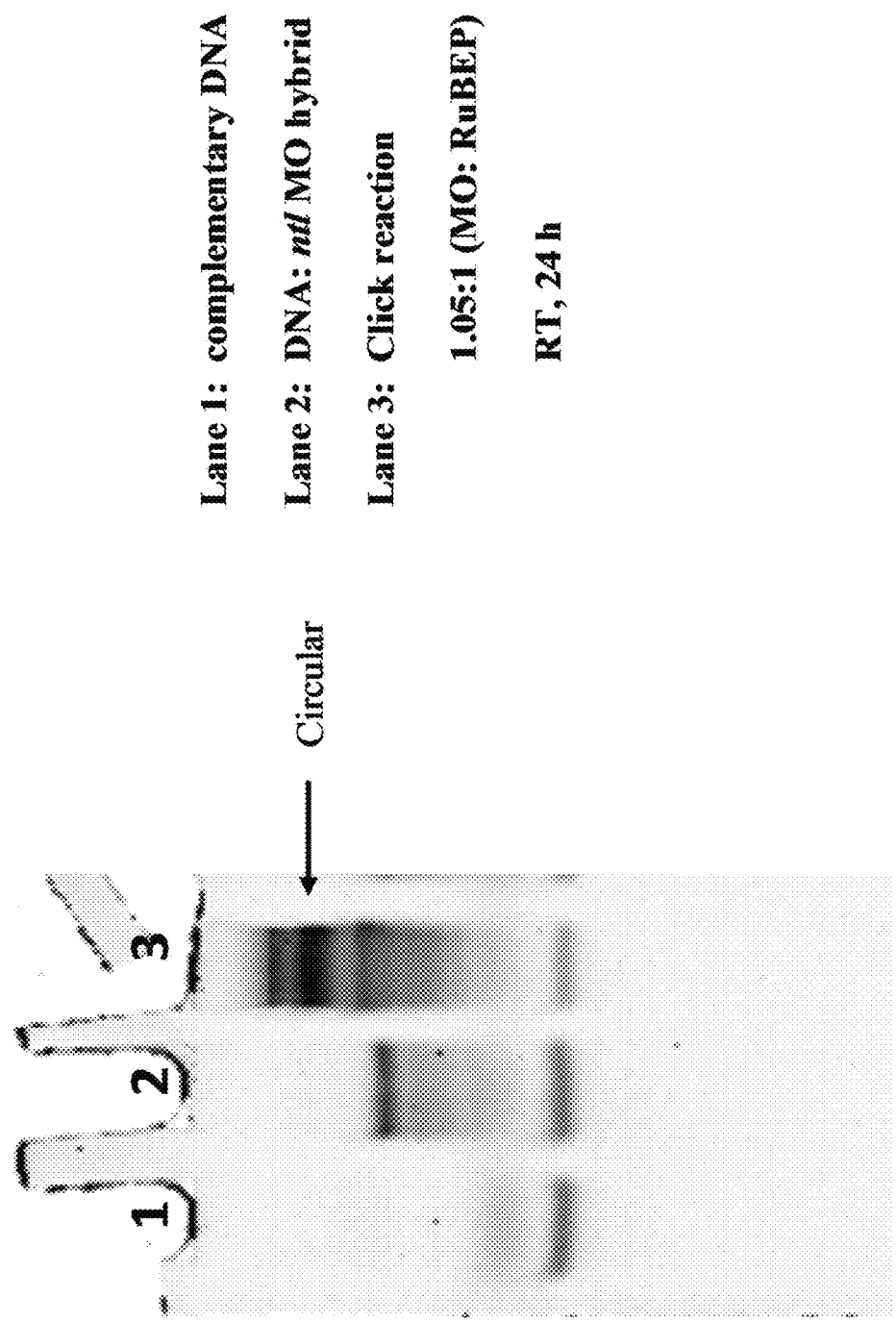
FIG. 18 is an image of a gel demonstrating the results of an experiment observing ntl-MO circularization. Lane 1 depicts complementary DNA. Lane 2 depicts a DNA:ntl MO hybrid. Lane 3 depicts a Click reaction (1.05:1 MO:RuBEP, RT, 24 h). 15% native PAGE gel-shift assay showing controls (lanes 1 and 2) and formation of Ru-cMO-ntl (lane 3). Circular product is indicated by the arrow. No additional purification was performed before in vivo testing. Due to initial impurities of bis-azido-ntl MO, the same circularization efficiency could not be achieved as with bis-azido-chd MO.
Figure 19:
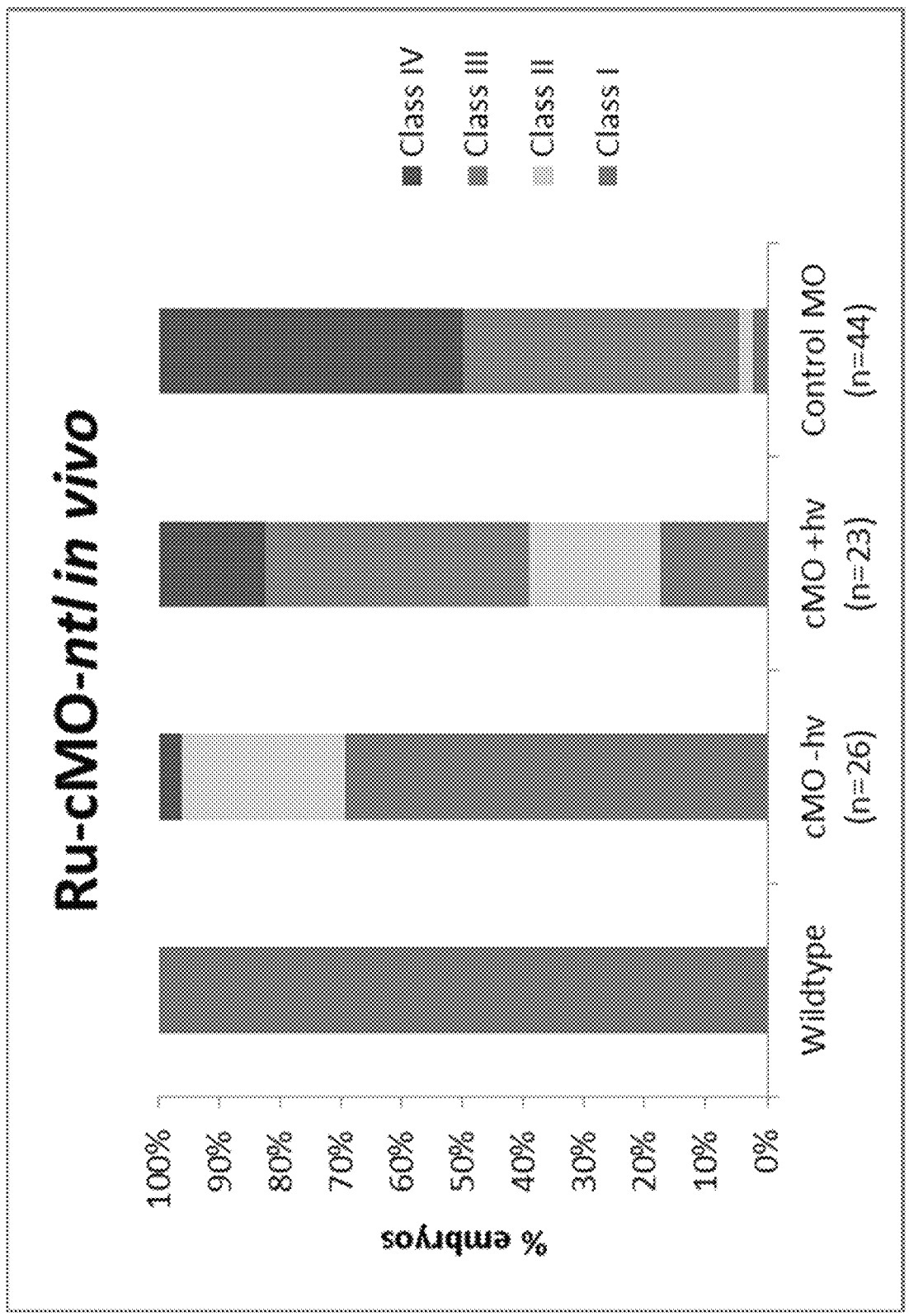
FIG. 19 is a graph depicting Ru-cMO-ntl in vivo data. MO Control:Zebrafish embryos were injected at the 1-cell stage with 0.25 mM ntl-MO and imaged at 24 hpf. Ru-cMO-ntl: Zebrafish embryos were injected at the 1-cell stage with 0.25 mM Ru-cMO-ntl. Half of the embryos were irradiated (450 nm, 14 mW/cm$^2$, 5 min) at 1 hpf, while the other half were incubated in the dark. Embryos were scored for phenotype at 24 hpf and compared to wildtype.

Representative images of the 3 levels of chd knockdown phenotypic response compared to wildtype are shown in FIG. 15. Half of the Ru-cMO-chd embryos were irradiated with 450-nm light (14 mW/cm$^2$, 5 min) at 1 hpf and returned to dark incubation. FIGS. 16A-16D depict representative images of uninjected control (FIG. 16A), Ru-cMO-chd-injected embryos incubated in the dark (FIG. 16B), Ru-cMO-chd-injected embryos irradiated with 450-nm light (FIG. 16C), and positive control embryos injected with MO-chd (FIG. 16D). A graph of phenotypic responses (FIG. 16E) confirms that Ru-cMO-chd was significantly caged in vivo, with only 14% of embryos showing some level of MO-chd activity. After irradiation, 92% of embryos developed with the expected chd knockdown phenotype, showing that the retained Ru moiety did not affect MO activity in vivo. The 8% with normal development can be attributed to injection variability, as this was consistent with the MO-chd control injections (~5% normal phenotype). To confirm sequence specificity, identical experiments were performed with Ru-cMO targeting ntl (Tallafuss et al., 2012, Development (Cambridge, England) 139:1691-1699), and similar caging/uncaging results were obtained (FIGS. 17-19). Ru-MO-ntl showed increased background activity. Although not wishing to be bound by any particular theory, this result is likely due to the slight impurities in the injection sample. The ntl bis-azido MO was received in lower purity than chd bis-azido MO, which decreased the yield and purity of the desired circular product. RuBEP was injected as a control with and without irradiation, and no toxicity or phenotypic response was observed (FIG. 31). Additionally, a scramble morpholino was injected into 1-cell stage embryos and resulted in normal development (FIG. 32 and Table 11).

The results described herein demonstrate the synthesis and characterization of the first ruthenium photolinker, RuBEP, and demonstrate reaction with bis-azide-functionalized oligonucleotides to form circular, caged oligos in good yields and purity. Ru-caged antisense MOs underwent efficient Ru$^{2+}$-ligand exchange upon 450-nm irradiation, to reveal the biologically active, linear structures. The pendant Ru$^{2+}$ moiety did not adversely affect target hybridization (FIGS. 13-14) or biological activity (FIG. 16E). RuBEP may be useful to cage many other azide-functionalized biomolecules, e.g., peptides, lipids, oligosaccharides in addition to in vivo applications for Ru-caged MOs. The 1-P and 2-P inorganic photochemistry of $[Ru(bpy)_2(X)_2]^{2+}$ complexes, and other Ru photolinkers, may be useful to allow multiplexed caging/uncaging for diverse applications in biology and materials science.

Example 2: Synthesis of Exemplary Compounds of the Invention

Figure 25:
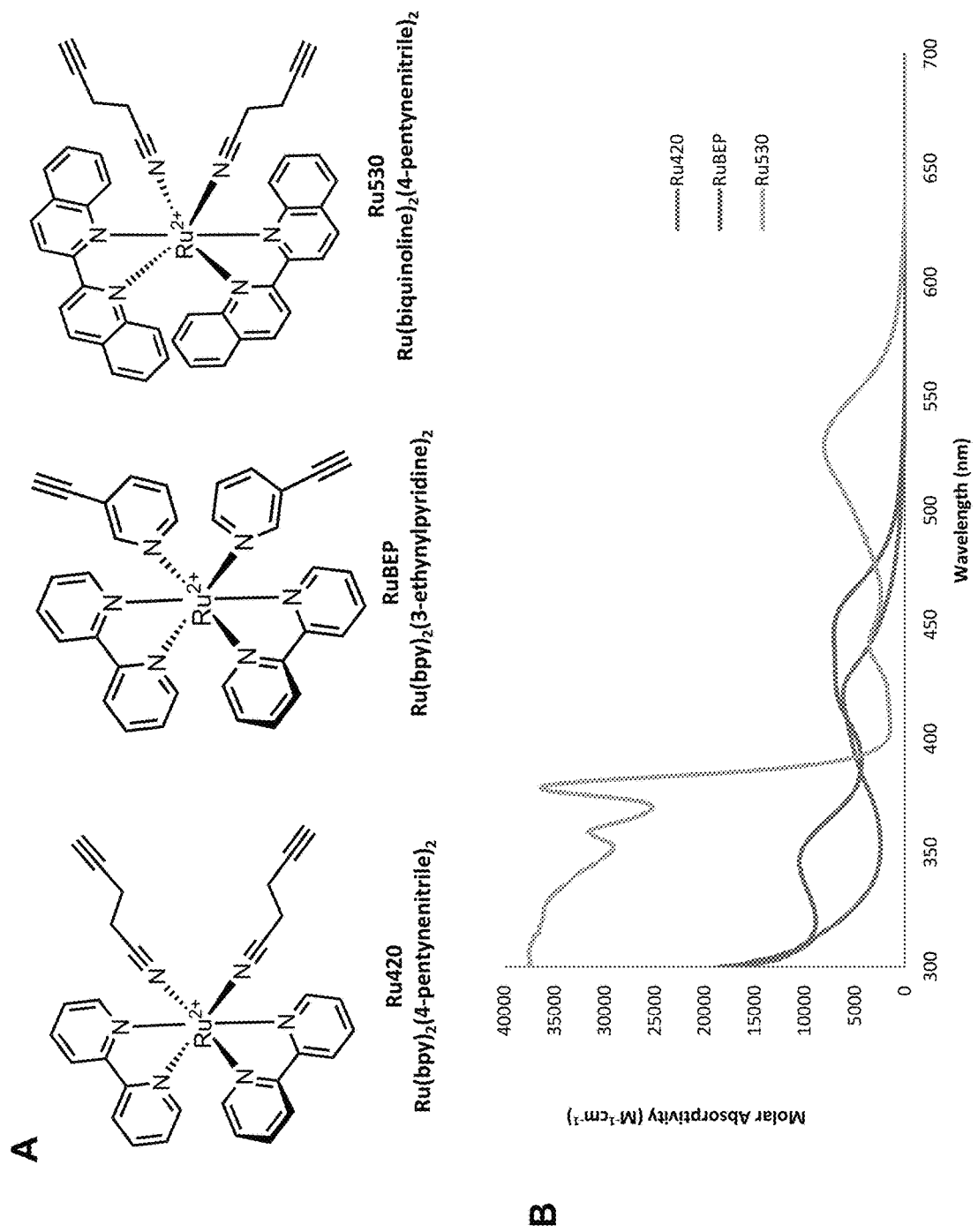
FIG. 25, comprising

Compounds $[Ru(bpy)_2(4\text{-pentynenitrile})_2][Cl]_2$ (Ru420) and $[Ru(biq)_2(4\text{-pentynenitrile})_2][Cl]_2$ (Ru530) are compounds of the invention which are useful for multiplexing of DNA and morpholino oligonucleotides (FIG. 25A). Ru420 and Ru530 can be selectively activated (FIG. 25B), and can be combined with a nitrobenzyl linker for further multiplexing.

Synthesis of $[Ru(bpy)_2(4\text{-pentynenitrile})_2][Cl]_2$ (Ru420)

104.4 mg (0.20 mmol) $Ru(bpy)_2Cl_2$ and 114 mg (0.44 mmol, 2.2 eq) $AgSO_3CF_3$ were dissolved in 10 mL of methanol, and stirred at room temperature for 45 min. Solid AgCl was filtered out, then 87.5 μL (0.1 mmol, 5 eq) 4-pentynenitrile was added. The reaction was heated to 70° C. for 45 min until the color changed from red to yellow. After the reaction was removed from heat, 10 mL DI water was added, and the methanol was removed under reduced pressure. Solid $NH_4PF_6$ (approx. 0.1 g) was added to the solution, and the $PF_6$ salt was extracted by dichloromethane. Product was purified by silica column chromatography with 1:9 acetonitrile:dichloromethane as the eluent. The water-soluble chloride salt was generated using an Amberlite IRA-410 chloride resin with methanol as the eluent. Yield: 56.8 mg, 42%. $^1$H NMR (500 MHz, CD$_3$CN) δ 2.20 (t, 1H, J=2.7, PN—H11), 2.43 (m, 2H, PN—H10), 2.85 (dd, 2H, J=6.0, PN—H9), 7.27 (ddd, 1H, J=5.5, bpy-H7), 7.63 (ddd, 1H, J=5.7, bpy-H8), 7.85 (ddd, 1H, J=5.6, bpy-H2), 7.96 (td, 1H, J=7.9, bpy-H6), 8.27 (td, 1H, J=8.0, bpy-$H_3$), 8.38 (d, 1H, J=8.1, bpy-H5), 8.52 (d, 1H, J=7.3, bpy-$H_4$), 9.34 (ddd, 1H, 3 bpy-H1). Expected Mass: 571.65, HRMS: 571.1173.

Synthesis of [Ru(biq)$_2$(4-pentynenitrile)$_2$][Cl]$_2$ (Ru530)

203 mg (0.98 mmol) RuCl$_3$, 494 mg (1.92 mmol, 1.9 eq) biquinoline, 219 mg (5.2 mmol) LiCl, and 222 mg (2 mmol, 2 eq) hydroquinone were dissolved in 3.3 mL DMF and heated to 135° C. for 45 min. Reaction mixture was cooled slowly to room temperature and added dropwise to 600 mL of water while stirring. Solid was filtered and washed with water, redissolved in dichloromethane, and washed 2× with water. Product was recrystallized by removing % of the solvent and adding dropwise to 250 mL of ether. Ru(biq)$_2$Cl$_2$ was collected by vacuum filtration and used without further purification for the next step.

160 mg (0.27 mmol) Ru(biq)$_2$Cl$_2$ from previous step was dissolved in 35 mL of methanol. 132 mg (0.51 mmol, 2.2 eq) AgSO$_3$CF$_3$ was added, reaction was stirred at room temperature for 30 min 204 μL (2.33 mmol, 10 eq) 4-pentynenitrile was added and the solution was heated to 70° C. for 45 min. Ru(biq)$_2$(4-pentynenitrile)$_2$[PF$_6$]2 was extracted and purified as described for Ru420, final yield 79 mg, 10% overall yield. The water-soluble chloride salt was generated using an Amberlite IRA-410 chloride resin with methanol as the eluent. $^1$H NMR (500 MHz, D$_2$O) δ 1.86 (t, 2H, J=3, PN—H3), 2.39 (m, 4H, PN—H2), 2.98 (m, 4H, PN—H1), 6.72 (d, 2H, J=8, biq-H8), 6.84 (t, 2H, J=8, biq-H9), 7.43 (t, 2H, J=7, biq-H4), 7.68 (m, 2H, biq-H11), 7.82 (d, 4H, J=8, biq-H5,H10), 8.05 (t, 2H, J=7, biq-H3), 8.21 (m, 2H, biq-H12), 8.28 (d, 2H, J=8, biq-H7), 8.32 (m, 2H, biq-H2), 8.59 (d, 2H, J=8, biq-H6), 9.29 (m, 2H, biq-H1). Expected Mass: 771.89, HRMS: 771.1807

Example 3: Synthesis of Circular Ru-DNA

Figure 26:
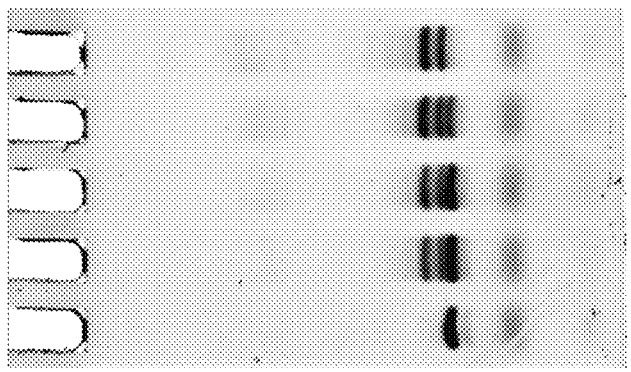
FIG. 26 is an image of a time-course gel showing the progression of the reaction of the synthesis of circular Ru-DNA.

Circular Ru-DNA was synthesized by titrating in the photolinker RuBEP in 0.25 nmol increments over the course of four hours, into a solution containing the DNA and all other reagents. Titration was continued until molar equivalents were reached. This reaction was performed at 32° C. with 2 equivalents of Cu(I) and 10 equivalents of THPTA as a copper-stabilizing ligand. Progression of the reaction was monitored using a time-course gel (FIG. 26).

Example 4: Stem-Loop Design of Exemplary Circular Ru-DNA Molecules

Figure 27:
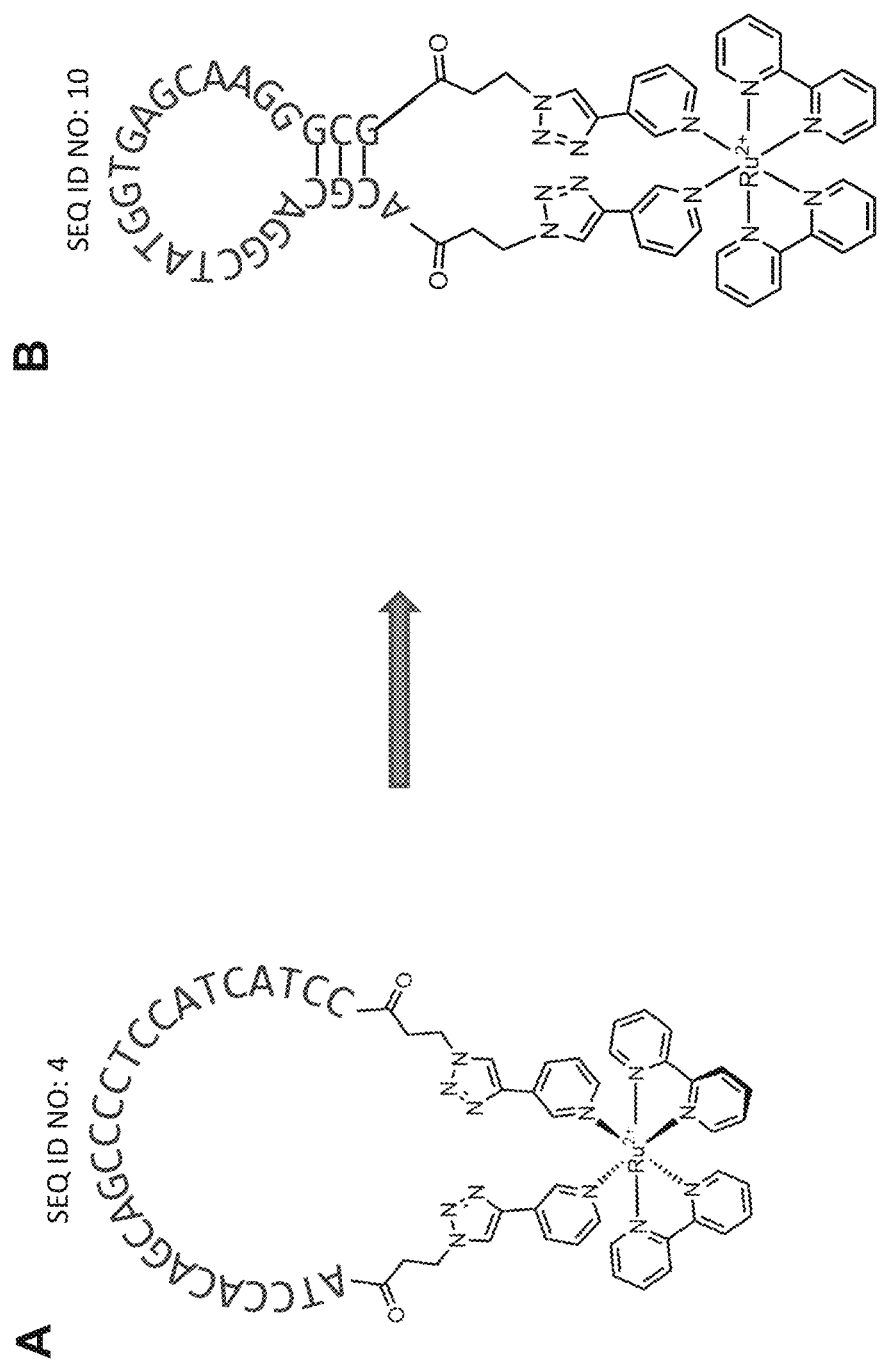
FIG. 27, comprising

An alternative method for preparing circular Ru-DNA molecules of the present invention includes the use of a stem-loop design of the oligonucleotide. The initial design of the caged molecule included the use of dilute conditions and random thermodynamic motion to circularize the oligo via a click reaction (FIG. 27A). However, an alternative embodiment includes intramolecular base pairing in the oligonucleotide, resulting in a stem-loop design that brings the two ends of the oligonucleotide closer together (FIG. 27B), thereby increasing the efficiency of forming a circular structure and thus improving the caging of the molecule.

Figure 28:
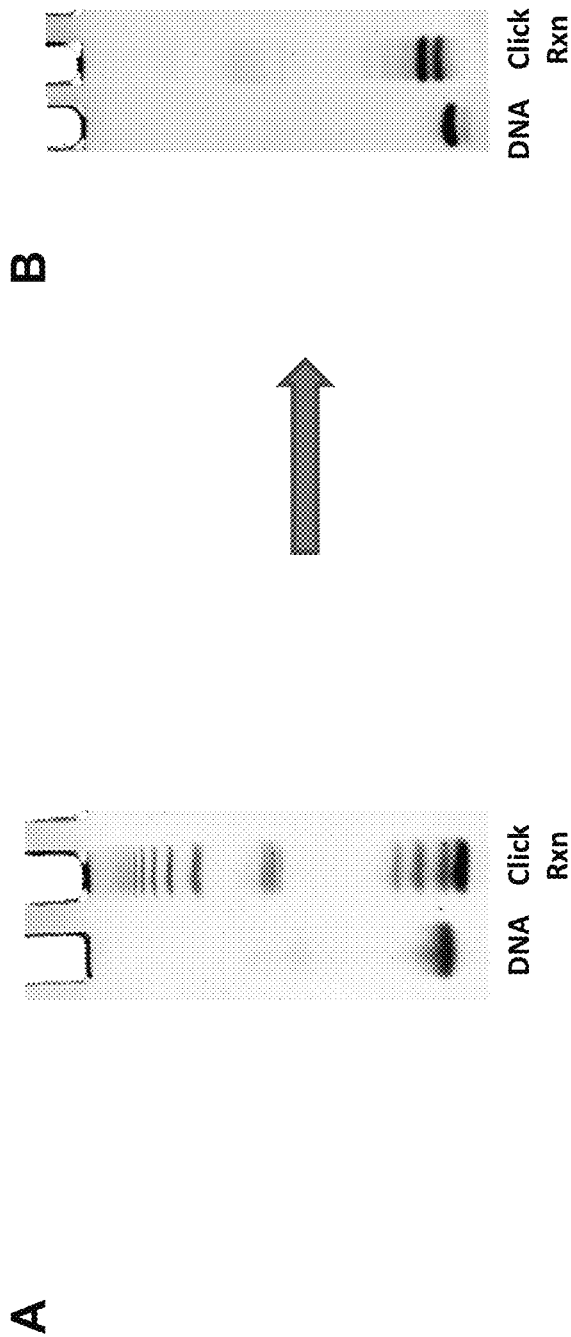
FIG. 28, comprising
Figure 29:
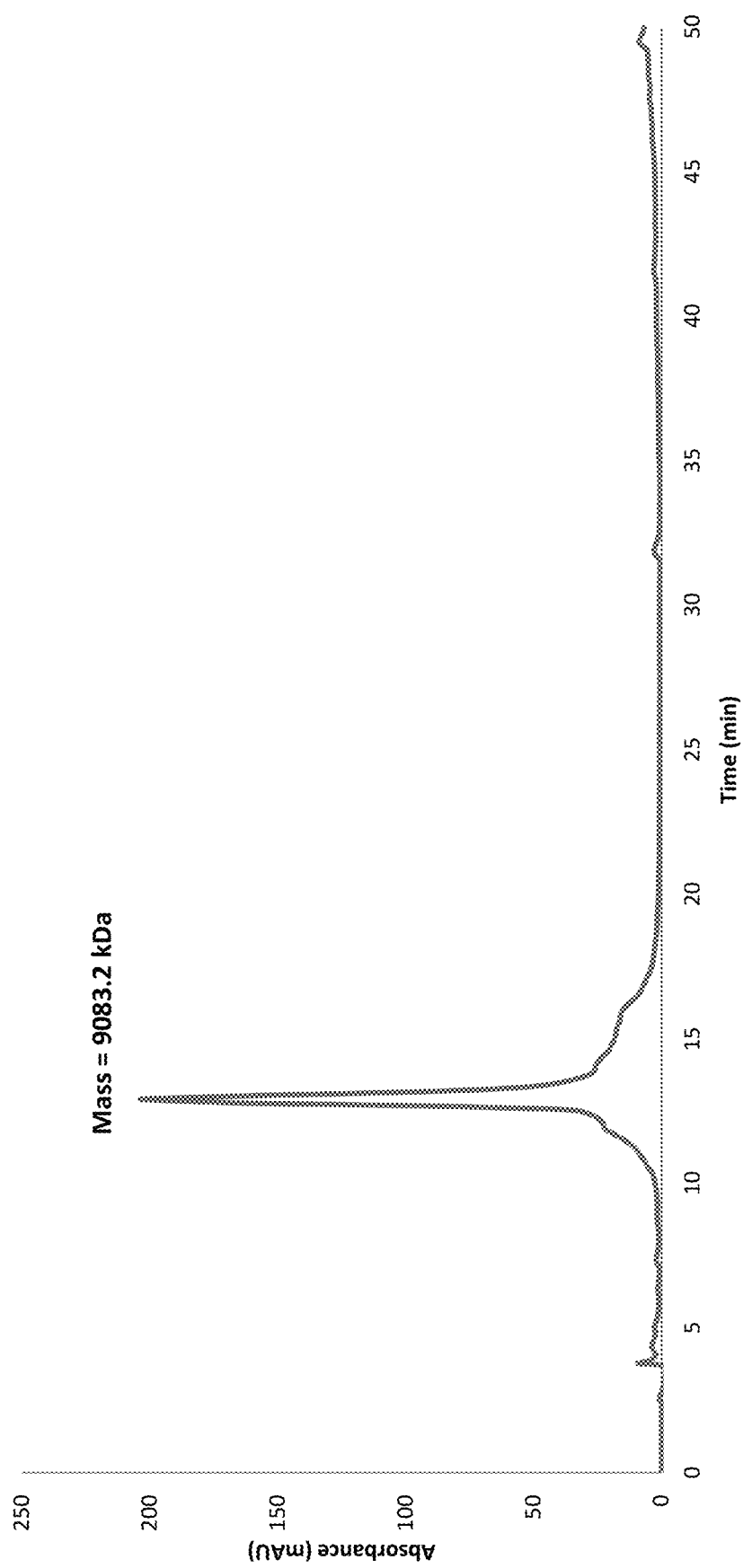
FIG. 29 is a graph of an HPLC trace of purified product from a stem-loop DNA click reaction. The trace identified the presence of only one peak, demonstrating the formation of one product. The many shoulder "lumps" surrounding the peak are side-products or some small polymer. Expected mass for circular Ru=9085.2 kDa.

Performing the click reaction using the stem-loop design of the oligonucleotide was found to reduce contamination of the product and allowed for recovery of unreacted oligonucleotide. As observed by gel electrophoresis (FIG. 28A), when performing the click reaction using a linear oligonucleotide, the main product (the bottom band) is contaminated significantly by extensive polymerization. These polymers may be easily removed by HPLC, however product yield was found to decrease as a result. In contrast, the use of an oligonucleotide comprising a stem-loop design resulted in a lack of polymerization, and 98% of the original oligonucleotide could be recovered through HPLC purification (FIG. 28B). The HPLC trace identified the presence of only one peak, demonstrating the formation of one product (FIG. 29).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations

---

What is claimed is:

1. A composition comprising at least one ruthenium-based photolinker compound of formula (II):

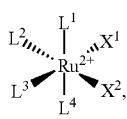

(II)

wherein in formula (II):
$L^1$, $L^2$, $L^3$, and $L^4$ are each independently a ligand; and
$X^1$ and $X^2$ are each independently a monodentate photolabile ligand having a reactive moiety,
wherein the reactive moiety is selected from the group consisting of an alkyne group, azide group, alkyl bromide group, aryl bromide group, a maleimide group, and a carbonyl group.

2. The composition of claim 1, wherein $X^1$ and $X^2$ are each independently selected from the group consisting of 3-ethynylpyridine, 3-(bromomethyl)pyridine, maleimide, nicotinaldehyde, 1-(4-(pyridin-3-yl)-1H-1,2,3-triazol-1-yl) ethanone, 4-pentynenitrile, and 4-aminobutyne.

3. The composition of claim 1, wherein $L^1$ and $L^2$ are joined to form a first bidentate ligand and $L^3$ and $L^4$ are joined to form a second bidentate ligand, further wherein the first bidentate ligand and the second bidentate ligand are selected from the group consisting of 2,2'-bipyridyl (bpy) and biquinoline.

4. The composition of claim 1, wherein $L^1$, $L^2$, and $L^3$ are joined to form a tridentate ligand, further wherein the tridentate ligand is 2,2':6',2"-terpyridine.

5. The composition of claim 4, wherein $L^4$ is a fluorophore.

6. The composition of claim 1, wherein the compound of formula (II) is selected from the group consisting of [Ru (bipyridine)$_2$(3-ethynyl-pyridine)$_2$]$^{2+}$, Ru(bipyridine)$_2$(3-ethynylpyridine)$_2$Cl$_2$, Ru(bipyridine)$_2$(3-ethynylpyridine)$_2$ (PF$_6$)$_2$, [Ru(biquinoline)$_2$(4-pentynenitrile)$_2$]$^{2+}$, Ru(biquinoline)$_2$(4-pentynenitrile)$_2$Cl$_2$, Ru(biquinoline)$_2$(4-pentynenitrile)$_2$(PF$_6$)$_2$, [Ru(bipyridine)$_2$(4-aminobutyne)$_2$]$^{2+}$, [Ru(bipyridine)$_2$(4-pentynenitrile)$_2$]$^{2+}$, [Ru(bipyridine)$_2$(nicotinaldehyde)$_2$]$^{2+}$, [Ru(bipyridine)$_2$(1-(4-(pyridin-3-yl)-1H-1,2,3-triazol-1-yl)ethanone)$_2$]$^{2+}$, [Ru(bipyridine)$_2$(3-(bromomethyl)pyridine)$_2$]$^{2+}$, [Ru(bipyridine)$_2$(maleimide)$_2$]$^{2+}$, a salt thereof, and any combinations thereof.

7. The composition of claim 1, wherein the compound of formula (II) is a compound of formula (III):

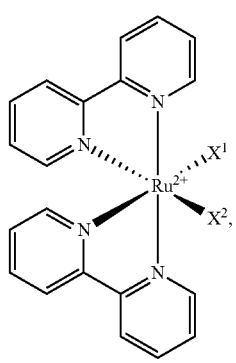

(III)

wherein in formula (III):
$X^1$ and $X^2$ are each independently a monodentate photolabile ligand having a reactive moiety, wherein the reactive moiety is selected from the group consisting of an alkyne group, azide group, alkyl bromide group, aryl bromide group, a maleimide group, and a carbonyl group.

8. A composition comprising at least one ruthenium-based photolinker compound of formula (II):

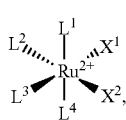

(II)

wherein in formula (II):
$L^1$, $L^2$, $L^3$, and $L^4$ are each independently a ligand; and
$X^1$ and $X^2$ are each independently a monodentate photolabile ligand having a reactive moiety;
wherein the reactive moiety is selected from the group consisting of an alkyne group, azide group, alkyl bromide group, aryl bromide group, a maleimide group, and a carbonyl group; and
wherein the composition comprises a caged molecule, wherein the caged molecule comprises at least one active domain conjugated to the at least one ruthenium-based photolinker compound.

9. The composition of claim 8, wherein the active domain is at least one selected from the group consisting of a peptide, protein, antibody, oligonucleotide, polynucleotide, morpholino, antisense polynucleotide, probe, oligosaccharide, polysaccharide, and a small molecule.

10. The composition of claim 8, wherein the composition comprises a circular caged molecule comprising the at least one ruthenium-based photolinker compound and the active domain, wherein a first end of the active domain is conjugated to a first photolabile ligand of the compound and wherein a second end of the active domain is conjugated elsewhere on the compound.

11. The composition of claim 10, wherein the second end of the active domain is conjugated to a second photolabile ligand of the compound.

12. The composition of claim 9, wherein the active domain is an oligonucleotide comprising a nucleic acid sequence that is substantially complementary to a target molecule.

13. The composition of claim 12, wherein the oligonucleotide comprises at least one intramolecular base pair.

14. The composition of claim 9, wherein the active domain is a morpholino comprising a nucleobase sequence substantially complementary to a target nucleic acid.

15. The composition of claim 8, wherein the caged molecule further comprises a cell penetrating domain.

16. The composition of claim 8, wherein the caged molecule further comprises a label.

17. A method of manipulating the expression of a gene in a cell comprising administering to the cell a composition comprising a caged molecule comprising an active domain conjugated to the at least one ruthenium-based photolinker compound of formula (II)

(II)

wherein in formula (II):
$L^1$, $L^2$, $L^3$, and $L^4$ are each independently a ligand; and
$X^1$ and $X^2$ are each independently a photolabile ligand having a reactive moiety;
wherein the reactive moiety is selected from the group consisting of an alkyne group, azide group, alkyl bromide group, aryl bromide group, a maleimide group, and a carbonyl group;
wherein the active domain manipulates the expression of the gene.

18. The method of claim 17, wherein the method further comprises irradiating the cell thereby cleaving the ruthenium-based photolinker compound and exposing the active domain.

19. The method of claim 17, wherein the active domain is at least one selected from the group consisting of a peptide, protein, antibody, oligonucleotide, polynucleotide, morpholino, antisense polynucleotide, probe, oligosaccharide, polysaccharide, and a small molecule.

20. The method of claim 18, wherein the active domain is an oligonucleotide comprising a nucleic acid sequence that is substantially complementary to a target molecule.

21. The method of claim 19, wherein the oligonucleotide comprises at least one intramolecular base pair.

22. The method of claim 18, wherein the active domain is a morpholino comprising a nucleobase sequence substantially complementary to a target nucleic acid.

23. The composition of claim 1, wherein the $X^1$ reactive moiety binds to a first end of an active domain and the $X^2$ reactive moiety binds to a second end of the active domain to form a circular caged molecule.

24. The method of claim 17, wherein $X^1$ and $X^2$ are each independently selected from the group consisting of 3-ethynylpyridine, 3-(bromomethyl)pyridine, maleimide, nicotinaldehyde, 1-(4-(pyridin-3-yl)-1H-1,2,3-triazol-1-yl)ethanone, 4-pentynenitrile, and 4-aminobutyne.

* * * * *